United States Patent [19]
Ikuno et al.

[11] Patent Number: 4,983,019
[45] Date of Patent: Jan. 8, 1991

[54] ENDOSCOPE LIGHT SOURCE APPARATUS

[75] Inventors: Yuji Ikuni, Oume; Toshiaki Nishikori, Sagamihara; Akihiko Miyazaki; Kazunari Nakamura, both of Hachioji; Fumiyuki Onoda, Futyu; Hiromasa Suzuki, Akishima; Takeaki Nakamura, Hino; Yoshinao Oaki, Hachioji; Atsushi Kidawara, Tachikawa; Masahide Kanno; Hisao Yabe, both of Hachioji; Shinichi Katoh, Oume, all of Japan

[73] Assignee: Olympus Optical Co., Ltd., Tokyo, Japan

[21] Appl. No.: 538,610

[22] Filed: Jun. 13, 1990

Related U.S. Application Data

[63] Continuation of Ser. No. 190,963, Mar. 6, 1988, abandoned.

[30] Foreign Application Priority Data

| May 6, 1987 | [JP] | Japan | 62-110053 |
| May 6, 1987 | [JP] | Japan | 62-110054 |
| Feb. 19, 1988 | [JP] | Japan | 63-37744 |
| Feb. 19, 1988 | [JP] | Japan | 63-37745 |
| Feb. 19, 1988 | [JP] | Japan | 63-37747 |
| Feb. 25, 1988 | [JP] | Japan | 63-24530 |
| Feb. 26, 1988 | [JP] | Japan | 63-44704 |
| Feb. 26, 1988 | [JP] | Japan | 63-44705 |
| Feb. 26, 1988 | [JP] | Japan | 63-44707 |
| Feb. 26, 1988 | [JP] | Japan | 63-44702 |
| Apr. 28, 1988 | [JP] | Japan | 63-105973 |

[51] Int. Cl.[5] .......................... G02B 5/22; A61B 1/06
[52] U.S. Cl. .................................. 350/313; 350/315; 350/316; 350/317; 350/318; 358/98; 358/42; 128/6
[58] Field of Search ............... 350/313, 315, 317, 318, 350/316; 358/98, 42; 128/6; 362/293, 32

[56] References Cited

U.S. PATENT DOCUMENTS

| 4,524,383 | 6/1985 | de Rooij | 358/42 |
| 4,621,284 | 11/1986 | Nishioka et al. | 358/98 |
| 4,625,236 | 11/1986 | Fujimora et al. | 358/42 |
| 4,625,714 | 12/1986 | Toyota et al. | 358/98 |
| 4,631,582 | 12/1986 | Nagasaki et al. | 358/98 |
| 4,713,683 | 12/1987 | Fujimora et al. | 358/98 |
| 4,736,734 | 4/1988 | Matsuura et al. | 128/6 |

FOREIGN PATENT DOCUMENTS 60-76888 5/1985 Japan.
60-243625 12/1985 Japan.
61-82731 4/1986 Japan.

Primary Examiner—Jon W. Henry
Attorney, Agent, or Firm—Armstrong, Nikaido, Marmelstein, Kubovcik & Murray

[57] ABSTRACT

An endoscope light source apparatus which can feed an illuminating light adapted to a scope provided with a frame sequential type imaging device, a scope provided with a color mosaic type imaging device and a fiber scope has a light source lamp which can emit the illuminating light. A filter which can transmit the illuminating light is interposed in the light path connecting the light source lamp with the entrance end surface of a light guide capable of feeding the illuminating light to the scope and is provided within a cassette which is inserted through an inserting aperture provided on a housing containing the light source apparatus.

24 Claims, 51 Drawing Sheets

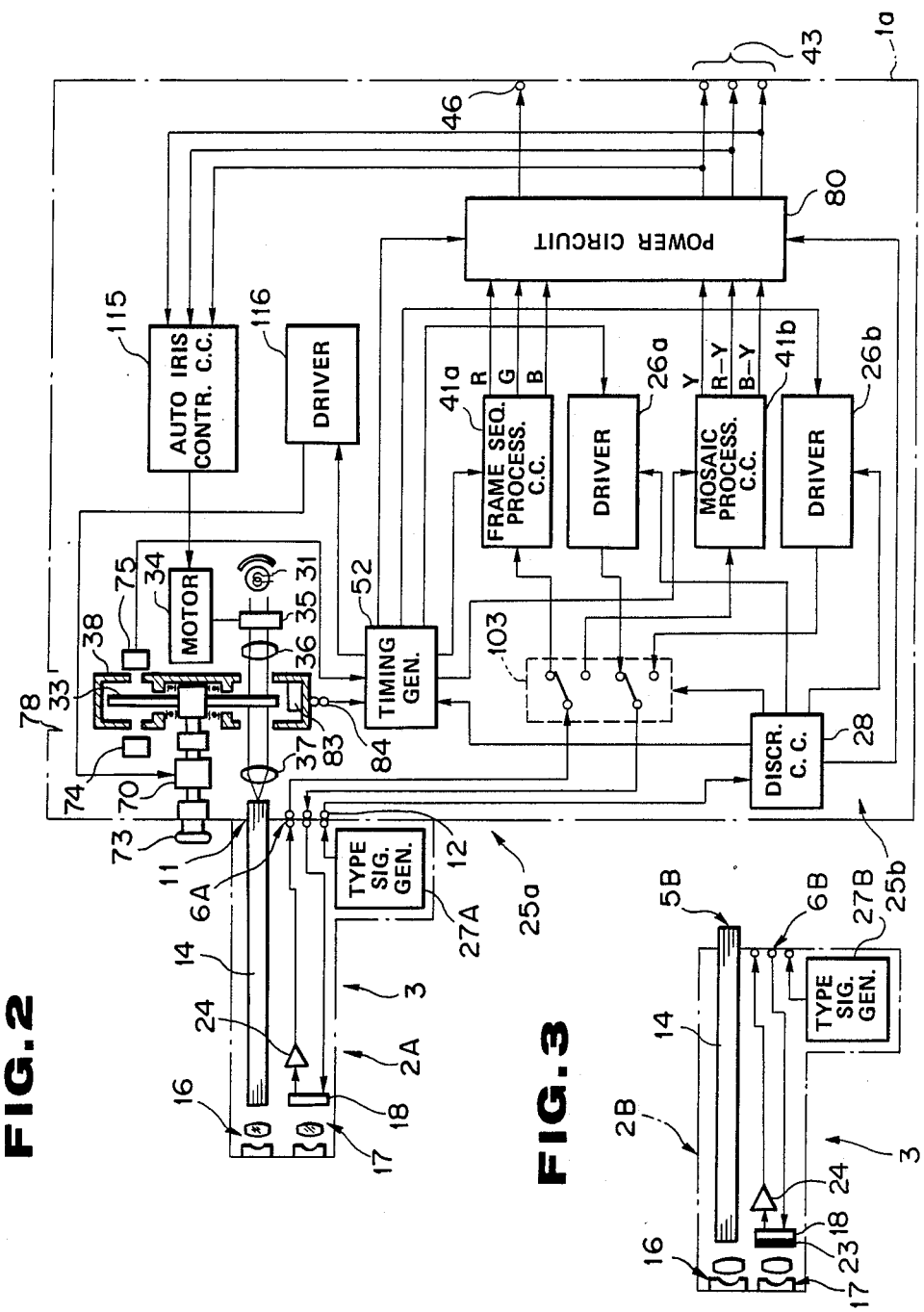

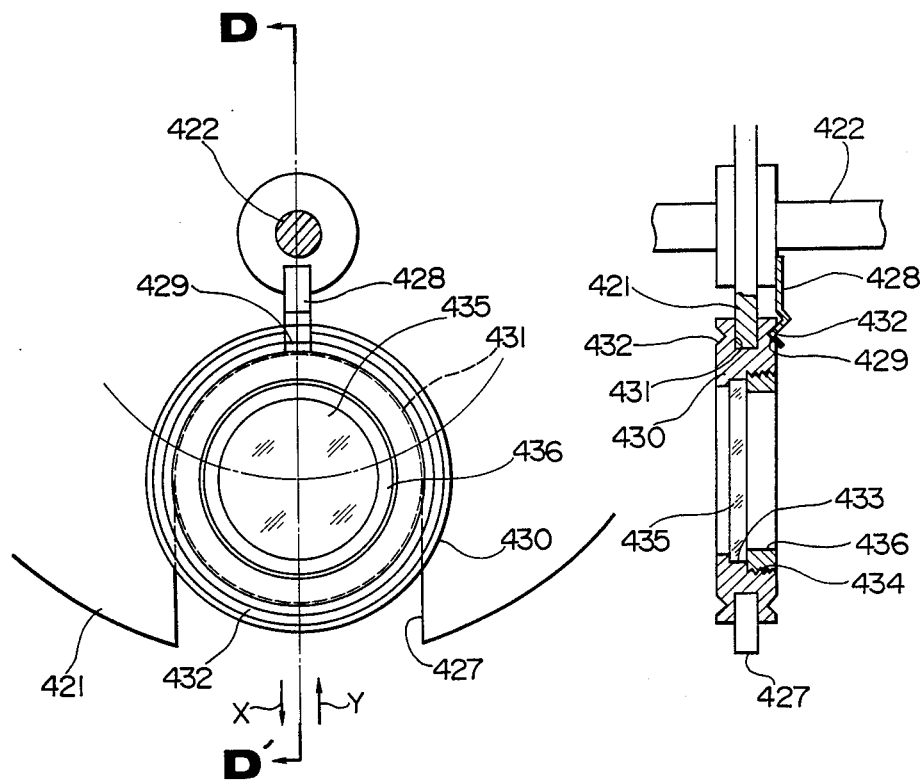

(a)  (b)

FIG.73
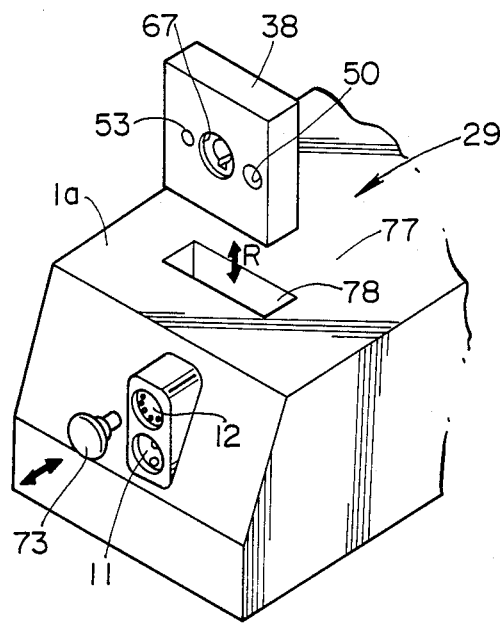
FIG.74
(a)
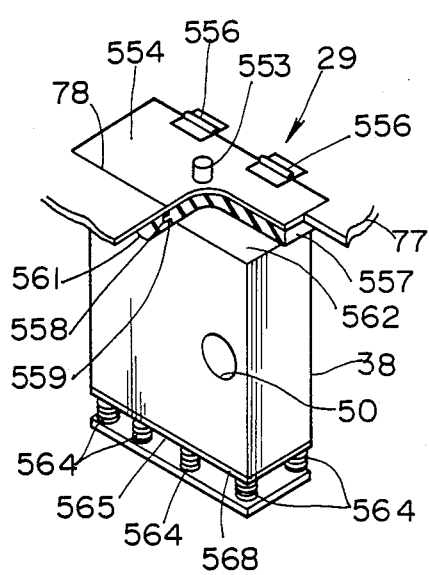
(b)
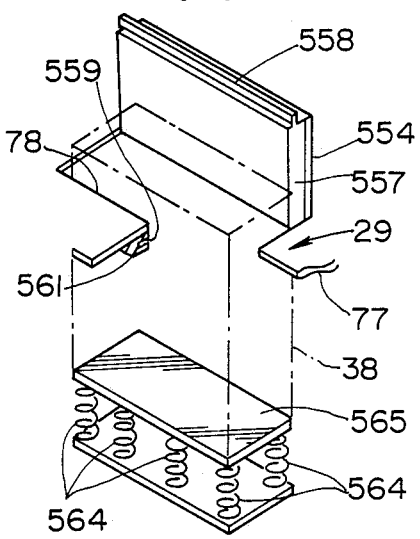

ENDOSCOPE LIGHT SOURCE APPARATUS

This application is a continuation of application Ser. No. 190,963 filed May 6, 1988, now abandoned.

FIELD OF THE INVENTION

This invention relates to an endoscope light source apparatus which can feed an illuminating light adapted to a scope provided with a frame sequential type imaging means, a scope provide with a color mosaic type imaging means and a fiber scope.

BACKGROUND OF THE INVENTION

Recently, there is extensively used an endoscope (called a scope or fiber scope) whereby organs within a body cavity can be observed by inserting a fine diameter insertable part into the body cavity or, as required, various curing treatments can be made by using a treating tool inserted through a treating tool channel.

Also, an electronic scope wherein such solid state imaging device as a charge coupled device (CCD) is used is variously suggested. This electronic scope has such advantages that the resolution is higher than in a fiber scope, it is easy to record and reproduce picture images and such picture image treatments as the magnification of picture images and the comparison of two picture images are easy.

Among the systems of imaging color picture images of the above mentioned electronic scope, there are such frame sequential type wherein the illuminating light is sequentially switched to R (red), G (green) and B (blue) as is shown, for example, in the gazette of a Japanese patent application laid open No. 82731/1986 and such color mosaic type (called also a simultaneous type) wherein a filter array in which color filters transmitting respectively such color lights as of R, G and B are arranged in the form of a mosaic is provided on the front surface of a solid state imaging device as is shown, for example, in the gazette of a Japanese patent application laid open No. 76888/1985. The frame sequential type has an advantage that pixels can be made fewer than in the color mosaic type. On the other hand, the color mosaic type has an advantage that no color displacement is produced for a quickly moving object to be imaged.

There are many kinds of the above mentioned electronic scope depending on the using objects. For example, an insertable part of an outside diameter of about 10 mm is used for an upper or lower digestive organ. On the other hand, an insertable part of an outside diameter less than about 5 mm is usually required, for example, for bronchia. Thus, it is physically and functionally unreasoanble to use the same kind of imaging device and the same kind of imaging system for various electronic scopes in which the outside diameter of the insertable part varies in a wide range. That is to say, for example, in order to realize an electronic scope for bronchia (fine diameter), an imaging device of few pixels can not help being used.

Thus, in case the pixels are few, in order to prevent the reduction of the resolution, the frame sequential type color imaging system wherein an object is illuminated in a frame sequential system with lights of respective wavelengths of R, G and B and frame sequential images are made under this illumination and are combined to color-display the object image is more advantageous than the color masaic type imaging system wherein color mosaic filters are used.

On the other hand, it is advantageous for the improvement of the picture quality to make the imaging system a color mosaic type by increasing pixels for the outside diameter of about 10 mm.

Now, the above mentioned fiber scope or electronic scope is used generally as connected to a light source apparatus feeding illuminating lights adapted to the respective scopes.

The illuminating method is different among the above mentioned fiber scope, frame sequential type electronic scope and color mosaic type electronic scope. That is to say, a white color light is required for the fiber scope and color mosaic type electronic scope. A light which is sequentially switched to R, G and B is required for the frame sequential type electronic scope. Further, even in the same frame sequential type imaging system, the spectral intensity and blanking period of the illuminating light must be varied in response to the kind of the solid state imaging device and the use of the endoscope. Therefore, the user must prepare respectively different light source apparatus depending on the kinds of the scopes and must make different operations. Thus, the economy and efficiency have been low.

By the way, a system wherein a fiber scope provided with an optical fiber bundle for transmitting images is connected to a controlling apparatus for an electronic scope provided with a frame sequential type light source apparatus so that the image may be observed on such displaying picture surface as of a monitor television is disclosed in the gazette of a Japanese patent application laid open No. 243625/1985. However, with this system, no electronic scope of a color mosaic type can be used and no naked eye observation can be made by using a fiber scope.

OBJECT AND SUMMARY OF THE INVENTION

An object of the present invention is to provide an endoscope light source apparatus which can feed an illuminating light adapted to the imaging system of the scope and the characteristic of the solid state imaging device.

In this invention, filters sequentially transmitting respective respective color lights in frame sequence are removably provided on a light path connecting a light source lamp emitting a white color light as an illuminating light with the entrance end surface of a light guide feeding the illuminating light to the scope.

The other features and advantages of the present invention will become apparent enough with the following explanation.

BRIEF DESCRIPTION OF THE DRAWINGS

FIGS. 1 to 12 relate to the first embodiment of the present invention.

FIG. 1 is an explanatory view showing the formation of an entire endoscope apparatus.

FIG. 2 is a block diagram showing the formation of the endoscope apparatus.

FIG. 3 is an explanatory view showing the formation of a color mosaic type electronic scope.

FIG. 4 is an explanatory view showing the formation of a fiber scope externally fitted with a cameral of a frame sequential type.

FIG. 5 is an explanatory view showing the formation of a fiber scope externally fitted with a camera of a mosaic type.

FIG. 6 is an explanatory view showing the formation of the fiber scope.

FIG. 7 is a sectioned view showing the formation of a light source part.

FIG. 8 is a sectioned view in the direction A—A' in FIG. 6.

FIG. 9 is a perspective view showing a rotary filter containing method.

FIG. 10 is an explanatory view showing the formation of a frame sequential type process circuit.

FIG. 11 is a block diagram showing the formation of a mosaic type process circuit.

FIG. 12 is a block diagram showing the formation of an output circuit.

FIG. 15 is a perspective view showing the formation of a rotary filter.

FIG. 16 is an explanatory view showing a method of fitting a filter part.

FIG. 17 is a perspective view of a light source apparatus.

FIG. 18 is a block diagram showing the formation of an endoscope apparatus.

FIG. 21 is an explanatory view showing the formation of a light source apparatus.

FIG. 22 is a side view showing an entire endoscope apparatus.

FIG. 23 is a perspective view of a video processor.

FIG. 24 is a block diagram showing the formation of the endoscope apparatus.

FIG. 25 is an explanatory view showing the first rotary filter for ordinary observation.

FIG. 26 is an explanatory view showing the second rotary filter for special picture images.

FIG. 27 is an explanatory view showing the transmitting characteristics of the respective filters of the first rotary filter.

FIG. 28 is an explanatory view showing the transmitting characteristics of the respective filters of the second rotary filter for special picture images.

FIG. 29 is an explanatory view showing the variation of the light absorbance of blood by the variation of the oxygen saturated degree of hemoglobin.

FIG. 32 is a block diagram showing the formation of an endoscope apparatus.

FIG. 33 is a sectioned view of a filter cassette for showing a rotary filter.

FIG. 34 is a sectioned view on line B—B' in FIG. 3.

FIG. 35 is a perspective view of a filter cassette changer.

FIG. 36 is a plan view of the filter cassette changer.

FIG. 37 is a perspective view showing the back side of the filter cassette changer.

FIG. 38 is a sectioned view on line C—C' in FIG. 36.

FIGS. 39 and 40 are explanatory views showing the transmitting characteristics of the respective filters of the rotary filter for special picture images.

FIG. 41 is an explanatory view showing the variation of the light absorbance of blood by the variation of the oxygen saturated degree of hemoglobin.

FIG. 42 is a sectioned view of a filter cassette for showing another example of the rotary filter for ordinary observation.

FIG. 43 is a sectioned view of a filter cassette for showing the rotary filter in a modification of this embodiment.

FIG. 44 is a perspective view showing the formation of a light source part.

FIG. 45 is a persepctive view of an endoscope controlling apparatus.

FIG. 46 is a block diagram showing the formation of the endoscope apparatus.

FIGS. 48 to 50 relate to the 12th embodiment of the present invention.

FIG. 48 is a perspective view showing the formation of a light source part.

FIG. 49 is an elevation showing a part of a turret disc.

FIG. 50 is a sectioned view in the direction D—D' in FIG. 49.

FIG. 51 is an elevation of a turret disc.

FIG. 52 is an elevation of a turret disc having a concentric net.

FIG. 53 is an elevation of a turret disc coated concentrically with a coating different in the transmittivity.

FIG. 54 is a schematic perspective view showing the formation of a filter cassette and light source part.

FIG. 55 is a perspective view showing the filter cassette and endoscope controlling apparatus.

FIG. 56 is an elevation of the interior of the filter cassette.

FIG. 57 is a sectioned view showing the formation of a light source part.

FIG. 58 is a perspective view showing a rotary filter containing method.

FIG. 59 is a block diagram showing the formation of an endoscope apparatus.

FIG. 60 is a perspective view of a filter cassette misinsertion preventing apparatus.

FIG. 61 is an explanatory view of a pull-out preventing apparatus formed so that the filter cassette may not be pulled out in case the rotary filter is rotating.

FIG. 62 is an explanatory view of a filter cassette illumianting light window lid apparatus.

FIG. 63 is an explanatory view of a filter cassette provided with shutter blades.

FIG. 64(a) is a sectioned view on line F—F' in FIG. 65.

FIG. 64(b) is a sectioned view on line E—E' in FIG. 64(a).

FIG. 65 is a sectioned view showing the formation of a light source part.

FIG. 66 is a sectioned view of a filter cassette.

FIG. 67 is a sectioned view on line G—G' in FIG. 66.

FIG. 68 is a perspective view of an endoscope controlling apparatus.

FIG. 69 is a sectioned view showing the formation of a light source part.

FIG. 70 is a block diagram showing the formation of an endoscope apparatus.

FIG. 71 is a block diagram showing the formation of an endoscope apparatus to which a scope provided with no type signal generating circuit can be connected and in which a frame sequential type or color mosaic type can be selected by an output circuit.

FIG. 72 is a block diagram showing the formation of an endoscope apparatus to which a scope provided with no type signal generating circuit can be connected and in which a frame sequential type or color mosaic type can be selected by removably inserting a filter cassette.

FIGS. 73 to 76 relate to the 19th embodiment of the present invention.

FIG. 73 is a perspective view of an endoscope controlling apparatus.

FIG. 74 is a perspective view explaining a filter cassette removably inserting apparatus energizing an energizing member with a lid.

FIG. 75 is an explanatory view of a filter cassette removably inserting apparatus energizing an energizing member with a push rod.

FIG. 76 is an explanatory view of a filter cassette provided with a handle.

FIG. 78 is an explanatory view showing the formation of a light source apparatus.

FIG. 79 is a perspective view showing the formation of a cassette filter.

FIG. 80 is a perspective view showing the light source apparatus.

DETAILED DESCRIPTION OF PREFERRED EMBODIMENTS

Figure 1:
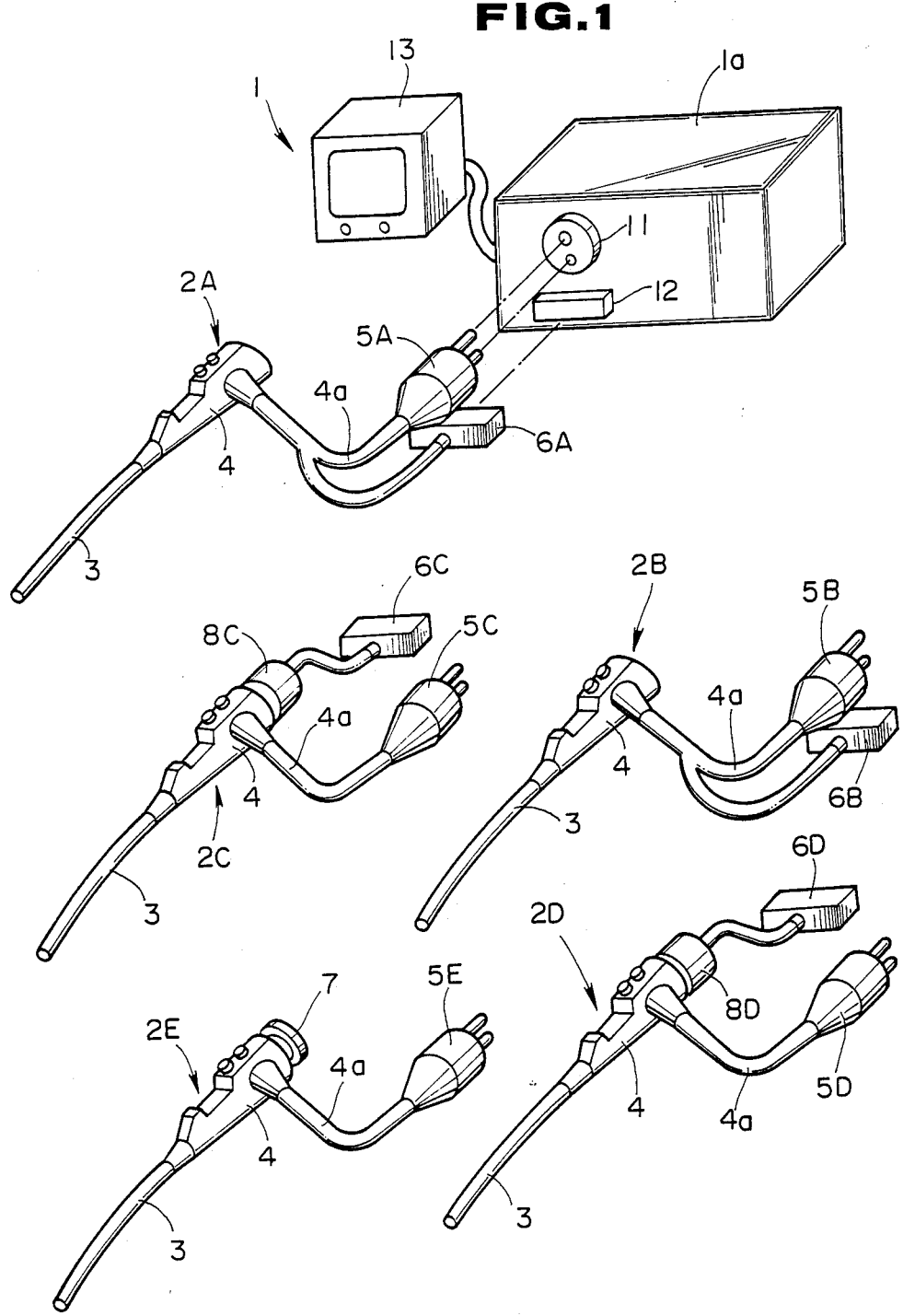
Figure 4:
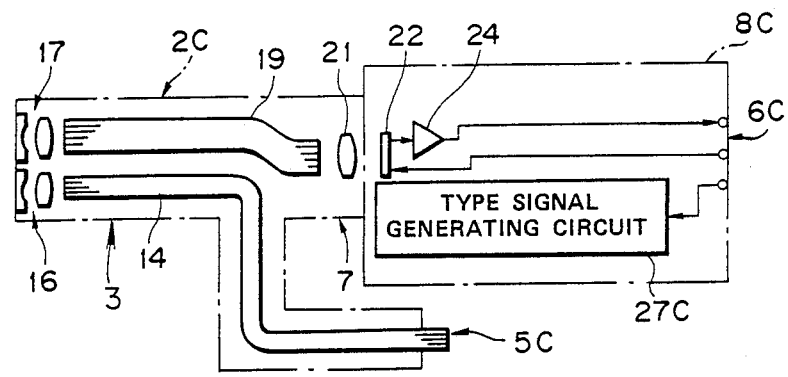
Figure 5:
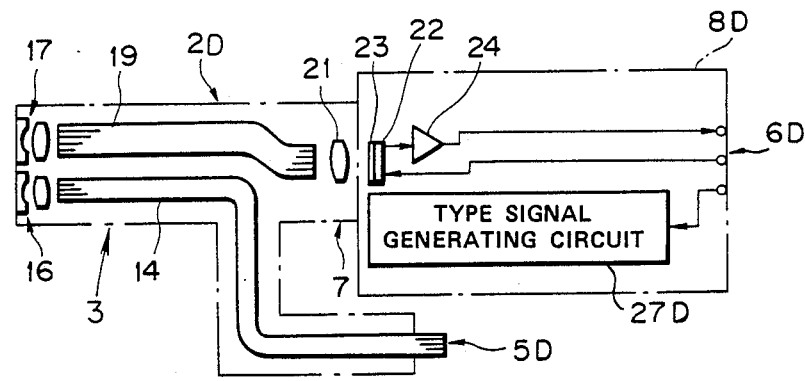

The embodiments of the present invention shall be explained in the following with reference to the drawings.

As shown in FIGS. 1 to 5, an endoscope apparatus 1 is provided with a control apparatus 1a containing a light source apparatus and video processor processing video signals of this embodiment and connectable with any of various scopes (endoscopes) 2A, 2B, 2C, 2D and 2E. The scopes are of such five kinds as are shown in the drawing, namely, a frame sequential type electronic scope 2A, a color mosaic type electronic scope 2B using a color mosaic filter, a fiber scope externally fitted with a frame sequential type television camera (mentioned as a fiber scope fitted with a frame sequential type television camera hereinafter) 2C, a fiber scope externally fitted with a color mosaic type television camera (mentioned as a fiber scope fitted with a color mosaic type television camera hereinafter) 2D and a fiber scope 2E.

Each of the above mentioned respective scopes 2A, 2B, 2C, 2D and 2E has a elongate insertable part 3 and an operating part 4 connected to the rear end side of this insertable part 3. A universal cord not illustrated is extended out of this operating part 4 and is provided at the tip with a light source connector 5A, 5B, 5C, 5D or 5E. In the frame sequential type electronic scope 2A and color mosaic type electronic scope 2B, not only the light source connectors 5A and 5B but also signal connectors 6A and 6B are provided respectively on the tip sides of the above mentioned universal cords 4a. In the fiber scope 2C fitted with the frame sequential type television camera and fiber scope 2D fitted with the color mosaic type television camera, a frame sequential type television camera 8C and color mosaic type television camera 8D are fitted respectively to the eyepiece parts of the fiber scopes 2E and signal cables extended out of the respective television cameras 8C and 8D are provided respectively with signal connectors 6C and 6D at the tips of the signal cables.

A set of connector receptacles is provided, for example, on the front surface of the control apparatus 1a so that the respective scopes 2 may be set to be in a usable state by connecting the connectors 5A, 6A; 5B, 6B;, 5C, 6C; 5D, 6D; 5E of the above mentioned respective scopes 2A, 2B, 2C, 2D and 2E (the reference numeral shall be represented by 2 hereinafter in case it is common to all these scopes). These connector receptacles consist of a light source connector receptacle 11 and signal connector receptacle 12. The above mentioned light source connector receptacle 11 is in the form connectable with the light source connectors 5A, 5B, 5C, 5D and 5E of the same shape of the above mentioned respective scopes 2. Also, the above mentioned signal connector receptacle 12 adjacent to the lower side of the light source connector receptacle 11 is in the form connectable with the signal connectors 6A, 6B, 6C and 6D of the same shape of the above mentioned respective scopes 2.

In case the above mentioned fiber scope 2E is connected, it will be able to be used for a naked eye observation but, in case the other scopes 2A, 2B, 2C and 2D are connected and used, imaged images will be able to be color-displayed by a color monitor 13 connected to the signal output end of the control apparatus 1a.

By the way, in this embodiment, each of the light source connectors 5A, 5B, 5C, 5D and 5E is provided with an air and water feeding connector not illustrated together with the light guide connector and the connector receptacle 11 can be connected with them. Further, a scope length discriminating resistance and antistatic protective resistance not illustrated are provided within each of the signal connectors 6A, 6B, 6C and 6D and the signal connector receptacle 12 can be connected with them.

A light guide 14 transmitting an illuminating light is inserted through each scope 2 so that the illuminating light fed to the entrance end surface of the light guide 14 from a light source part 15 of the light source apparatus 15 within the control apparatus 1a may be transmitted to the exit end surface side and may illuminate the forward object side through a light distributing lens 16 arranged forward of this exit end surface.

Each of the above mentioned scopes 2 has an image forming objective lens 17 arranged in the tip part of the insertable part 3. In the image forming position of this objective lens 17, in the frame sequential or color mosaic type electronic scope 2A or 2D, such solid state imaging device 18 as a CCD is arranged, on the other hand, in the fiber scope 2E or fiber scope 2C or 2D fitted with the television camera 8C or 8D, the entrance end surface of an image guide 19 is arranged to be present and, in the fiber scope 2E, an observation can be made with a naked eye brought close to the eyepiece part 7.

On the other hand, in the fiber scope 2E fitted with the frame sequential type television camera 8C or color mosaic type television camera 8D in the eyepiece part 7, a solid state imaging device 22 is arranged through an image forming lens not illustrated as opposed to an eyepiece lens 21.

An optical image formed on the image forming surface will be photoelectrically converted by the solid state imaging device 18 or 22 forming an imaging means, will be amplified by a pre-amplifier 24, will then be transmitted to the signal connector 6 (representing 6A, 6B, 6C or 6D) side through a signal transmitting line and will be input into a video processor 25a or 25b through the signal connector receptacle 12 connected with this signal connector 6. A solid state imaging device driving clock will be applied to the solid state imaging device 18 or 22 from a driver 26a or 26b of the above mentioned video processor 25a or 25b.

The other scopes than the fiber scope 2E are provided with type signal generating circuits 27A, 27B, 27C and 27D outputting scope discriminating type signals so that the scope may be discriminated by a discriminating circuit 28 within the control apparatus 1a through the signal connector 6.

Now, as shown in FIG. 2, a light source apparatus 15 consisting of a light source part 15a and two sets of video processors 25a and 25b are contained within the control apparatus 1a connectable with any of the above mentioned scopes 2.

Figure 7:
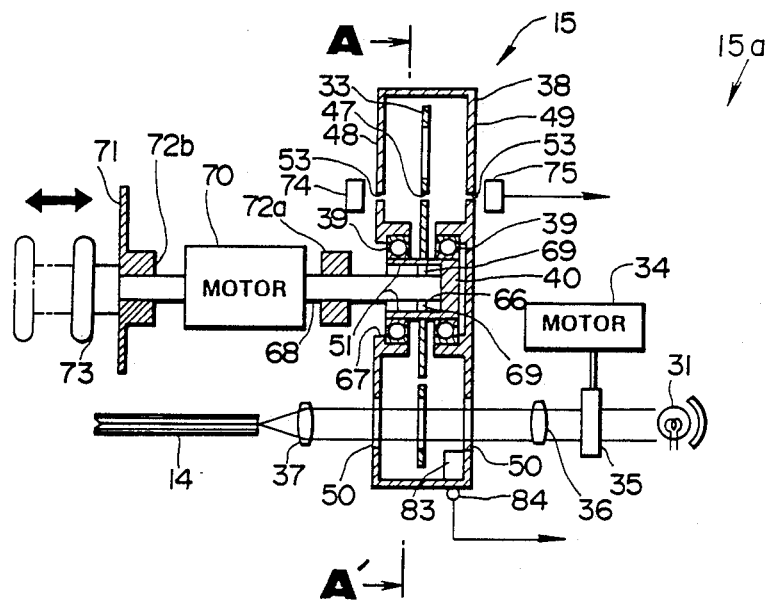
Figure 8:
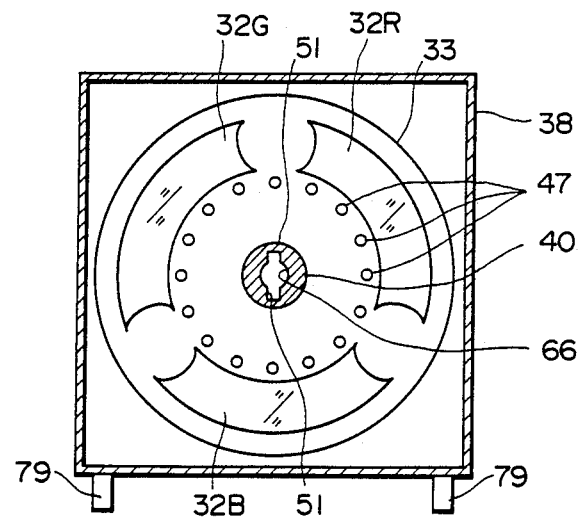
Figure 9:
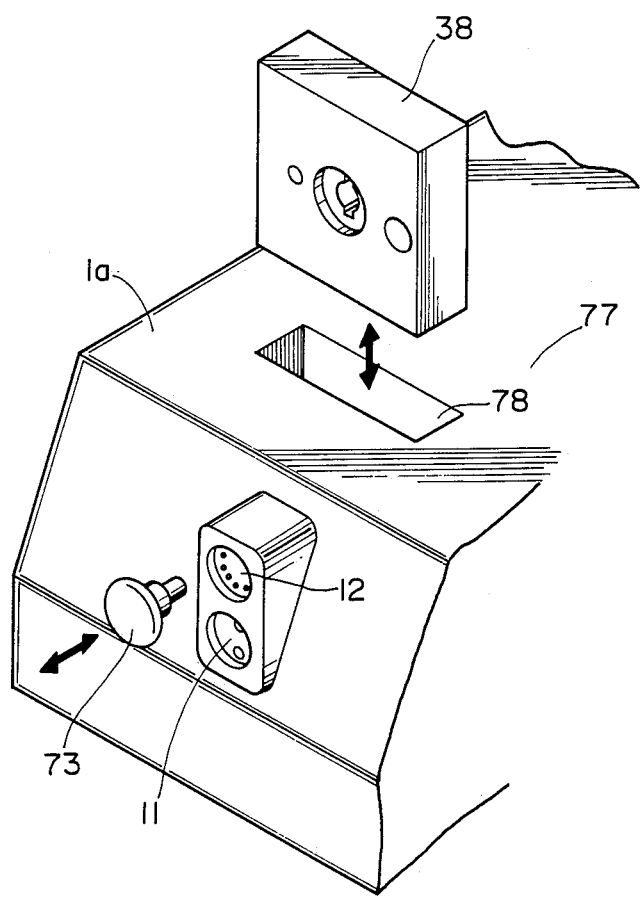

In the light source part 15a of the above mentioned light source apparatus 15, in FIGS. 7 and 8,. on the light path connecting a light source lamp 31 emitting a white color light with the entrance end surface of a light guide 14, there are arranged a diaphragm 35 driven by a diaphragm motor 34 to adjust the light amount, a condenser lens 36 condensing the white color light entering a rotary filter 33 and a condenser lens 37 making focused and defocused states on the entrance end surface of the light guide 14.

The above mentioned rotary filter 33 is disc-like, has filters 32R, 32G and 32B transmitting three primary colors of red (R), green (G) and blue (B) in the peripheral direction of the disc surface and has a plurality of holes 47 for detecting the timing of reading out the solid state imaging device signal provided in the peripheral direction on the inside diameter side of the color transmitting filters 32R, 32G and 32B.

The above mentioned rotary filter 33 is contained in a filter cassette 38 and is provided in the rotation center with a rotary shaft 40 borne by ball bearings 39 provided in the center part of a filter cassette 38.

The front surface plate 48 and back surface plate 49 of the above mentioned filter cassette 38 are provided with windows 5o so that the white color light emitted from the light source lamp 31 may pass through the color transmitting filters 32R, 32G and 32B. Further, the front surface plate 48 and back surface plate 49 are provided with windows 53 so as to see the above mentioned detecting holes 47. For example, a light emitting device 74 is arranged so as to see the holes 47 through one window 53 and, for example, a photosensor 75 is provided so as to see the holes 47 through the other window 53.

A den 66 having grooves 51 provided in the lengthwise direction are provided on the front surface side end surface of the above mentioned rotary shaft 40 and a window 67 is provided in the central part of the front surface place 48 so as to the above mentioned den 66.

A rotary filter driving motor 70 driving shaft 68 provided with pins 69 projected in the diametral direction so as to coincide with the above mentioned grooves 51 and borne by a sliding bearing 72a is inserted in the above mentioned den 66.

A substantially cylindrical removable knob 73 passing, for example, through the front surface plate 71 of the control apparatus 1a and borne by a sliding bearing 72b is provided forward of the above mentioned rotary filter driving motor 70.

A filter kind recording part 83 in which such information as of the spectral intensity and blanking period of the illuminating light passing through the rotary filter 33 is memorized, for example, by the combination or the like of a ROM (read only memory) and contact to discriminate the kind of the filter is provided within the above mentioned filter cassette 38 and is connected to a contact 84 provided on the side surface of the fiber cassette 38.

As in FIG. 3, the above mentioned filter cassette 38 is inserted through an opening 78 provided, for example, in the top plate 77 of the control apparatus 1a and is positioned by positioning pins 79 provided on the bottom surface of the filter cassette 38. After the filter cassette is positioned, when the removable knob 73 is pushed toward the control apparatus 1a, the driving shaft 68 of the rotary filter driving motor 70 will be inserted into a den 66 provided in the rotary shaft 40 supporting the rotary filter 33 so as to be able to transmit the rotation.

By the way, a contact 84 of a filter kind recording part 83 will be connected with a timing generator simultaneously with the positioning of the filter cassette 38, the kind and characteristic of the inserted rotary fiber 33 will be transmitted to the timing generator 52 and the signal adapted to them will be able to be output to the frame sequential type process circuit 41a, mosaic type process circuit 41b, drivers 26a and 26b, output circuit 80 and driver 116.

The above mentioned driver 116 will drive a rotary filter driving motor 70 by a synchronous signal adapted to the rotary filter 33 from the timing generator 52.

By the way, the above mentioned photosensor 75 will synchronize the timing of the clock of the timing generator 52 with the rotation of the rotary filter 33 and the output of this timing generator 52 will control the timing of the frame sequential type process circuit 41a.

Now, one video processor 25a is for processing frame sequential type signals. The signal input into the signal inputting terminal of the frame sequential type signal connector receptacle 12 will be input into the frame sequential type process circuit 41a and the signals imaged respectively under the illuminating lights of the respective wavelengths of R, G and B will be output as color signals R, G and B. These respective color signals R, G and B will be output as three primary color signals RGB from three primary color output ends 43 by an output circuit 80. The above mentioned color signals R, G and B will be converted to a compound video signal of an NTSC system and will be output from an NTSC output end 46.

Figure 10:
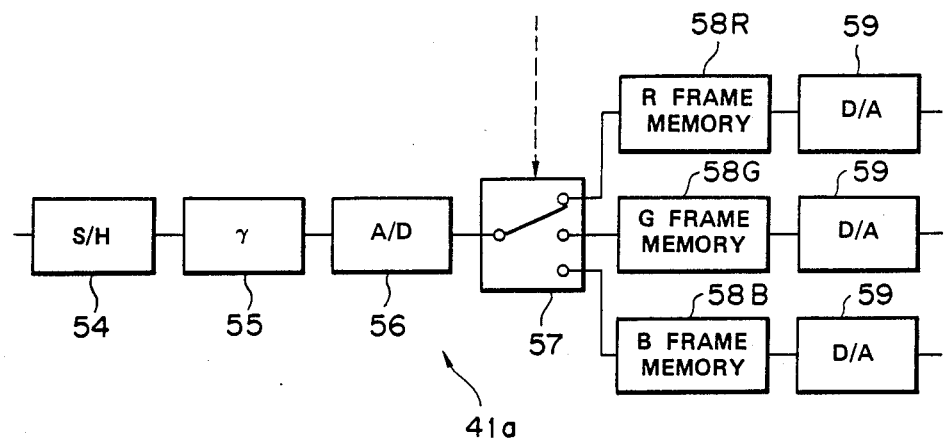

The above mentioned frame sequential type process circuit 41a is formed as shown, for example, in FIG. 10.

That is to say, the signal input through the preamplifier will be input into a sample holding circuit 54, will be sample-held, will be then γ-corrected in a γ-correcting circuit 55 and will be converted to a digital signal by an A/D converter 56. The signal imaged under the frame sequential illuminating lights of R, G and B through a multiplexer 57 switched by the signal of the above mentioned timing generator 52 will be written into an R frame memory 58R, G frame memory 58G and B frame memory 58B. The signal data written into these respective frame memories 58R, 58G and 58B will be simultaneously read out, will be converted respectively to analogue color signals R, G and B by a D/A converter 59 and will be output to an output circuit 80.

On the other hand, the signal imaged by the solid state imaging device 18 or 22 of the color mosaic type electronic scope 2B or fiber scope 2E externally fitted with the mosaic type camera will be input into the color mosaic type process circuit 41b and a luminance signal Y and color difference signals R-Y and B-Y will be output. This signal will be input into the output circuit 80, will be converted to a compound video signal of the NTSC system and will be output from the NTSC output end 46. The above mentioned luminance signal Y and color difference signals R-Y and B-Y will be converted to color signals R, G and B by the above mentioned output circuit 80 and three primary color signals RGB will be output from the three primary color signal output ends 43.

Figure 11:
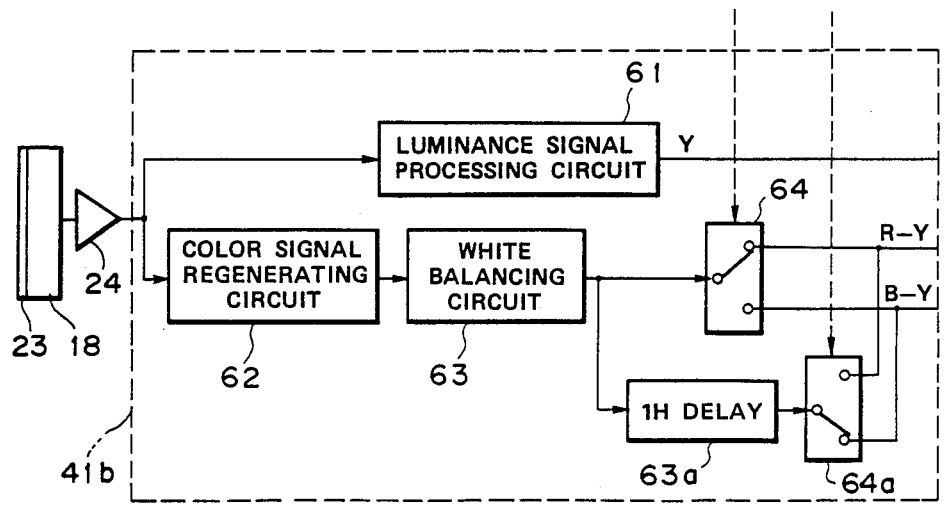
Figure 12:
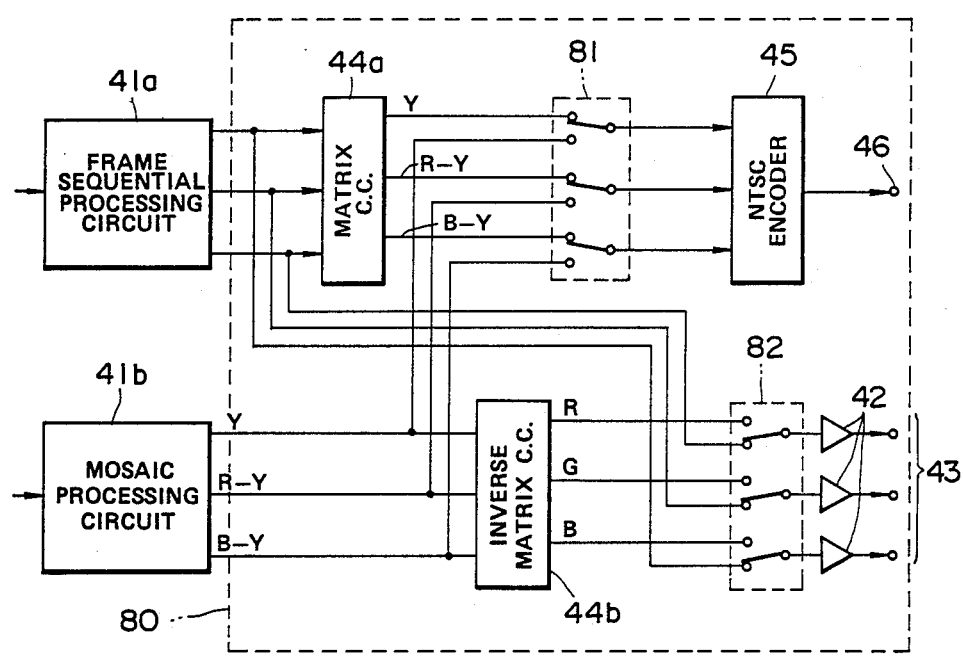

By the way, the above mentioned color mosaic type process circuit 41b is formed as shown, for example, in FIG. 11.

That is to say, the signal from the solid state imaging device 18 or 22 amplified by the pre-amplifier 24 will be passed through luminance signal processing circuit to produce a luminance signal Y. Also, the signal will be input into a color signal demodulating circuit 62 color difference signals R-Y and B-Y will be produced in each horizontal line in time series and will be white balance-compensated in a white balance circuit 63, one side will be input directly into an analogue switch 64, the other side will be delayed by one horizontal line in a 1H delay line 63a and will be input into an analogue switch 64a and color difference signals R-Y and B-Y will be obtained by a switching signal of a timing generator 62.

By the way, the timing generator 52 will apply signals respectively to the drivers 26a and 26b and NTSC encoder not illustrated and will control to process signals synchronized with driving pulses used to read signals out of the solid state imaging device 18 or 22. In this case, in the frame sequential type video processor 25a, a described above, the above mentioned timing generator 52 is synchronized with the rotary filter 33 by the output of a photosensor 75.

Now, the type signal generating circuits 27A, 27B, 27C and 27D are formed by connecting resistances or the like of respectively different resistance values, for example, between two terminals. On the other hand, the discriminating circuit 28 can discriminate the resistance value between two terminals of the connected scope by using a comparator or the like.

The above mentioned discriminating circuit 28 controls not only both drivers 26a and 26b but also the switching of a switching switch 103. For example, when the frame sequential type scope 2A or 2C is connected, the switch will be switched to the frame sequential side, the driving pulses of the driver 26a will be applied to the solid state imaging device 18 through the connector and the signal read out of the solid state imaging device 18 will be input into the frame sequential type process circuit 41a.

On the other hand, when the frame sequential type scopes 2A and 2C are not connected, the mosaic type process circuit side will be selected. By the way, by detecting the case of the mosaic type scope 2B or 2D, the switching switch 103 may be switched to the mosaic type side.

The above mentioned discriminating circuit 28 can cope with any system by transmitting a control signal also to the timing generator 52.

As shown in FIG. 10, the output circuit 80 is provided with a switching switch 81 of three circuits and two contacts between the output end of a matrix circuit 44a and an NTSC encoder 45 and with a switching switch 82 of three circuits and two contacts between the output end of an inverse matrix circuit 44b and a buffer 42 forming a driver.

In the above mentioned switching switch 81, when one contact side is switched on, the signal of the matrix circuit 44a will be led to the common NTSC encoder 45, will be made a video signal of the NTSC system and will be output from a common NTSC output end 46. When the other contact is selected, the signal of the mosaic type process circuit 41b will be led to the NTSC encoder 45 and will be output from the common NTSC output end 46.

On the other hand, in the other switching switch 82, when the frame sequential type side is selected, the output signal of the frame sequential type process circuit 41a will pass through the common buffer 42 forming the driver and will be output on one side to an automatic light adjusting circuit 115 and on the other side as three primary color signals from the common RGB output end 43. When the mosaic type process circuit side is selected, the three primary color signals R, G and B having passed through the inverse matrix circuit 44b will be output on the side to the automatic light adjusting circuit 115 and on the other side from the common RGB output end 43.

The above mentioned switching switches 81 and 82 can be respectively switched manually or as operatively connected.

The above mentioned automatic light adjusting circuit 115 drives the diaphragm motor 34 to adjust the diaphragm 35 so that the size of the video signal of an object may be constant.

By the way, the color transmitting filter may be a filter for such special observation as an infrared observation. In case a scope or fiber scope provided with a color mosaic type imaging means is to be used as connected, it will not be necessary to insert the rotary filter and the white light entering the entrance end surface of the light guide may be defocused by a condenser lens.

In this embodiment, the rotary filter is borne by the ball bearings fitted in the central part of the filter cassette but the ball bearings may not be fixed and such resilient member as, for example, a spring may be fixed to the outer race of the ball bearing to support the rotary filter. When the rotary filter is thus supported by the resilient member, even in case the axes of the rotary filter driving motor and rotary filter are somewhat different, the difference will be able to be absorbed by the resilient member.

Figure 13:
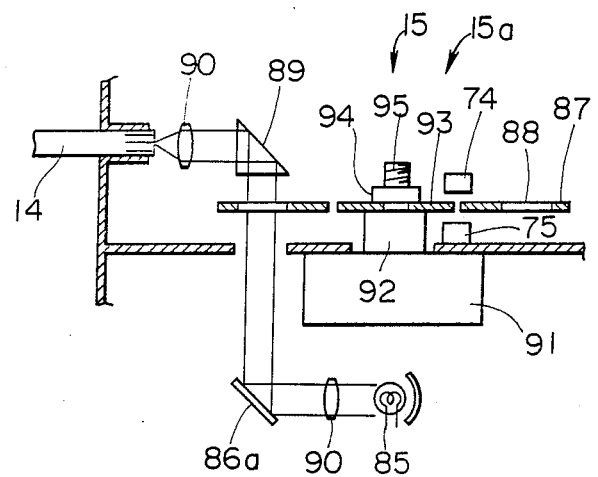
FIG. 13 relates to the second embodiment of the present invention and is a sectioned view showing the formation of a light source part.

FIG. 13 is a sectioned view showing the formation of a light source part showing the second embodiment.

A white color light emitted from a light source lamp 85 will pass through a condenser lens 90, will have the light path changed at right angles by a reflector 86a, will pass through filters 88 transmitting three primary colors of red (R), blue (B) and green (G) and provided in the rotary filter 87 to be made illuminating lights of the respective wavelength, will then have the light path changed again at right angles by a rectangular prism 89, will pass through a condenser lens 90 and will enter the entrance end surface of the light guide 14.

The rotary filter 87 is provided horizontally and a driving shaft 92 of a rotary filter driving motor 91 passes through the rotation center of the rotary filter 87.

The above above mentioned rotary filter 87 contacts a step part 93 of the above mentioned driving shaft 92 and is fixed to the driving shaft 92 and is fixed to the driving shaft 92 by a fixing nut 94 screwed to a male screw 95 provided in the tip part of the driving shaft 92.

By the way, the rotary filter 87 may be contained for protection within the cassette.

When the light source and filter driving part are provided as overlapped, the depth of the contour of the light source apparatus can be made smaller than in the first embodiment.

The other formations and operations are the same as in the first embodiment.

Figure 14:
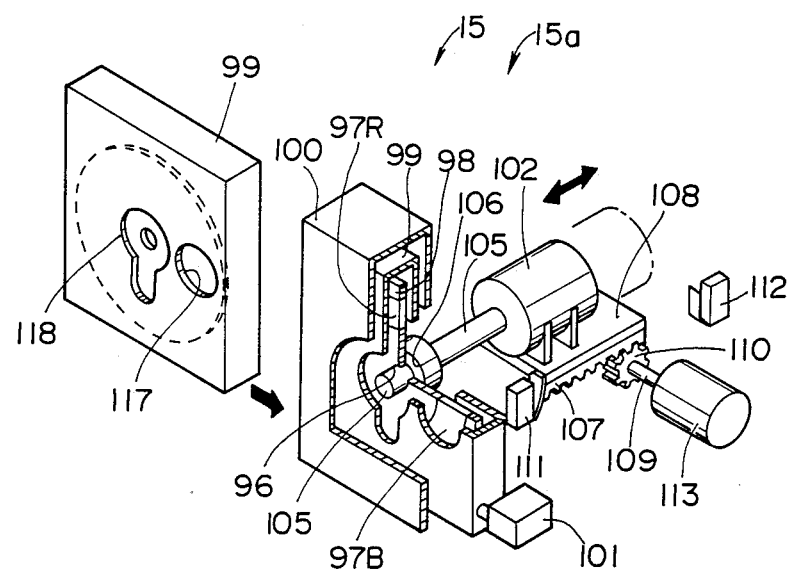
FIG. 14 is relates to the third embodiment of the present invention and is a perspective view of a light source part.
Figure 15:
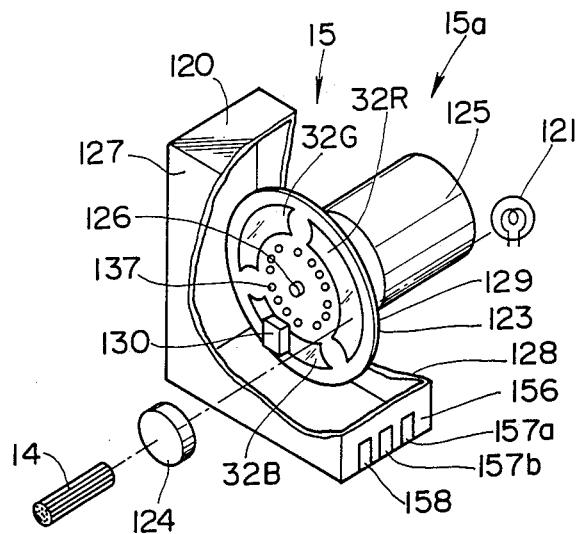
FIGS. 15 to 18 relate to the fourth embodiment.
Figure 16:
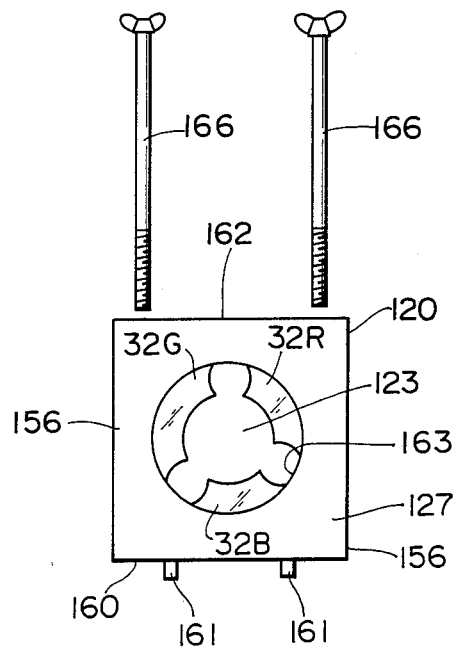

FIG. 14 is a perspective view of a light source part showing the third embodiment.

A rotary filter 98 like a disc, having a hole 96 in the rotation center and provided with filters 97R, 97G and 97B transmitting three primary colors of red (R), blue (B) and green (G) is contained within a filter cassette 99 so as to be insertable into a cassette case 100 provided within the light source apparatus 1a from the side surface of the filter cassette 99.

Windows 117 are provided respectively on the front surface and back surface of the above mentioned cassette filter 99 s that the white color light emitted from a light source lamp not illustrated may pass through the color transmitting filters 97R, 97G and 97B and further windows 118 are provided in the central parts of the front and back surfaces so as to be able to see a hole 96 provided in the central part of the rotary filter 98.

A switch 101 is provided as opposed to the above mentioned filter cassette 99 inserting direction so as to be on in the position of the end of the insertion.

A rotary filter driving motor 102 is provided on the back surface of the above mentioned cassette case 100. A small diameter part 105 in the tip part of a driving shaft 104 formed of a magnetic material of the above mentioned rotary filter driving motor 102 passes through the hole 96 of the above mentioned rotary filter 98. The plate surface of the rotary filter 98 contacts a step part 106 provided in the rear of the above mentioned small diameter part 105.

The above mentioned rotary filter driving motor 102 is fitted on a moving plate 108 provided with a rack 107 on the lower surface so as to be movable in the axial direction of the motor 102 by a pinion 110 meshing with the above mentioned rack 107 and provided on a driving shaft 109 of a moving motor 113.

Switches 111 and 112 are provided in the moving direction of the above mentioned moving plate 108. The switch 111 on the rotary filter side contacts the end surface of the moving plate 108 and the switch 112 in the back surface direction is separated from the end surface.

Now, when the filter cassette 99 is inserted into the cassette case 100, the filter cassette 99 will contact on the side surface with the switch 101 to drive the moving motor 113. When the moving motor 113 passes the small diameter part 105 of the driving shaft 104 through the hole 96 of the rotary filter 98 and the step part 106 contacts the plate surface of the rotary filter 98, the switch 111 will contact the end surface of the moving plate 108 to stop the moving motor 113.

By the way, when the filter cassette 99 is to be pulled out, the switch 111 is manually electrically released, the moving motor 113 is reversely rotated and the moving motor 113 is stopped by the switch 112.

By thus forming this embodiment, the rotary filter and driving motor can be automatically removably fitted to each other.

The other formations and operations are the same as in the first embodiment.

FIGS. 15 to 18 show the fourth embodiment of the present invention.

A light source part 15a of a light source apparatus 15 is formed of a light source lamp 121 emitting a white color light, a housing 120 containing a rotary filter 123 having filters 32R, 32G and 32B transmitting three primary colors of red (R), blue (B) and green (G) and fitted with a motor 125 rotating and driving the above mentioned rotary filter 123 and a condenser lens 124.

Figure 17:
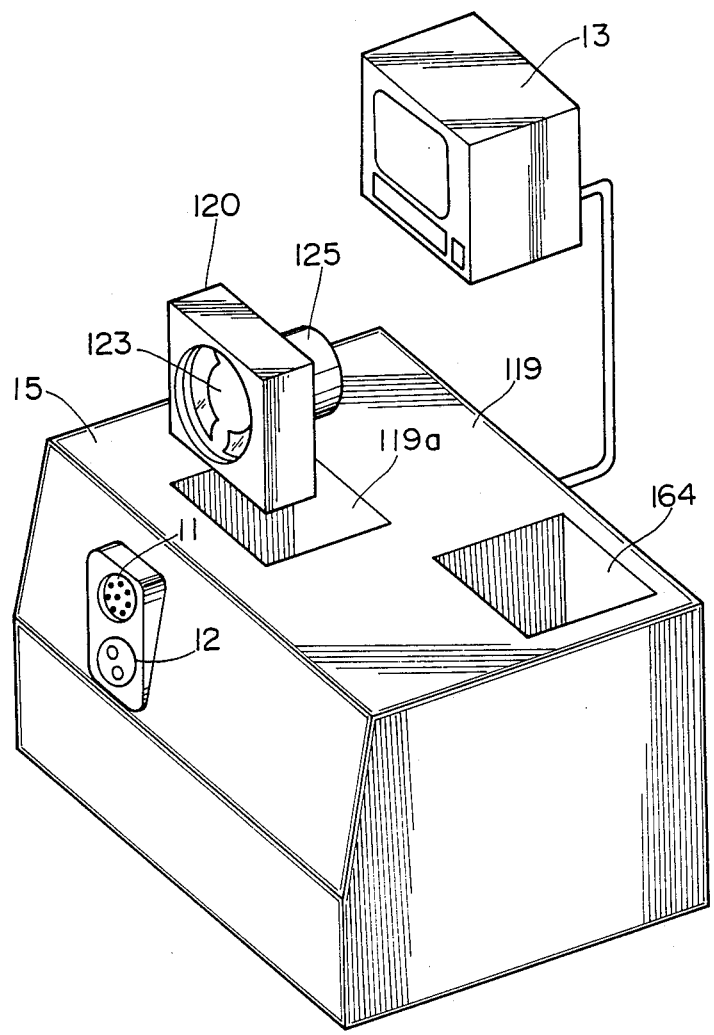
Figure 18:
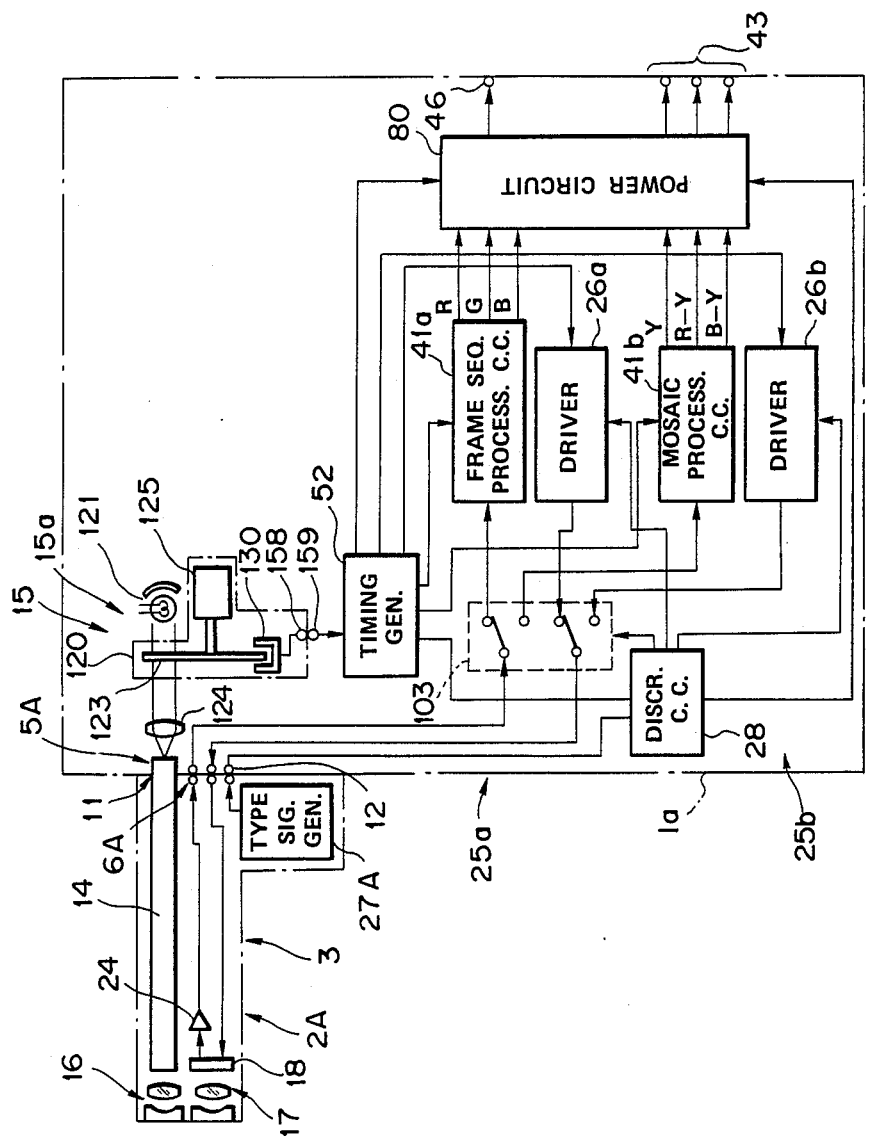

As shown in FIG. 17, the above mentioned housing 120 can be removably fitted into the light source apparatus 15 through an opening 119a on the upper surface plate 119 of the control apparatus 1a.

In the above mentioned housing 120, a window 163 through which illuminating lights of respective wavelengths can pass is provided on the front surface plate 127. On the back surface plate 128, a driving shaft 1261 is fitted to be projected into the housing 120 and to be fixed in the rotation center of the rotary filter 123 so that the contained rotary filter 123 may be rotated and driven. Further, on the back surface plate 128, a window not illustrated is provided so that the white color light from the light source lamp 121 may pass through the color transmitting filters 32R, 32G and 32B.

On the filter frame 129 of the rotary filter 123, a plurality of holes 137 for the detection of the timing of reading out solid state imaging device signals in the case of a frame sequence are provided in the peripheral direction and, on both sides of the plate surface of the filter frame 129, such position detecting sensors 130 as, for example, light emitting devices or photosensors are arranged to form a position detecting rotary encoder.

Current source contacts 157a and 157b of the motor 125 fitted to the housing 120 and a position detecting contact 158 are provided on the side surface plate 156 of the above mentioned housing 120 so that, at the same time as the housing 120 is housed within the light source apparatus 15, the position detecting contact 155 may be connected with a light source side position detecting contact 159.

On the lower surface of the bottom plate 160 of the above mentioned housing 120, positioning pins 161 are provided so that, when the housing 120 is housed within the light source apparatus 15, the color transmitting filters 32R, 32G and 32B may be positioned on the light path connecting the light source lamp 121 with the entrance end surface of the light guide 14 and can be fitted in recesses not illustrated provided on the light source apparatus side.

On the top plate 162 and the above mentioned bottom plate 160 of the above mentioned housing 120, holes not illustrated are provided so that winged bolts 166 may be passed and may be fixed by screwing with the light source apparatus side.

Now, in case the scope to be used is of a color mosaic type, as shown in FIG. 17, the housing 121 having the motor 125 is taken out of the light source apparatus 15, is contained in an opening 164 provided in the rear part of the control apparatus 1a and can be stored.

By the way, the above mentioned position detecting sensor 130 will synchronize the timing of the clock of the timing generator 52 with the rotation of the rotary filter 123 and the output of this timing generator 52 will control the timing of the frame sequential type process circuit 41a.

By the way, the color transmitting filter may be a filter for such special observation as an infrared observation. Further, the position detecting sensor may not be provided within the housing but may be provided on the light source apparatus side.

In case a scope provided with a color mosaic type imaging means or a fiber scope is to be used, it is not necessary to insert the rotary filter and the white color light entering the entrance end surface of the light guide may be defocused with a condenser lens.

Figure 19:
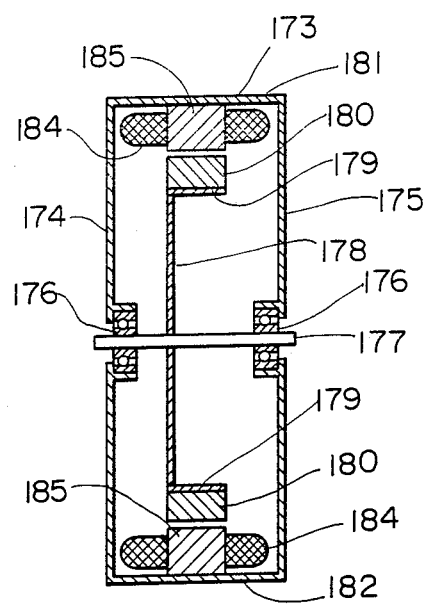
FIG. 19 is a sectioned view showing the formation of a rotary filter relating to the fifth embodiment.

FIG. 19 is a sectioned view showing the formation of a rotary filter showing the fifth embodiment.

A rotary shaft 177 borne by ball bearings provided in the middle of the front surface plate 174 and back surface plate 175 of a housing 173 is fixed in the rotation center of a rotary filter 178.

The above mentioned rotary filter 178 is disc-like and is provided with color transmitting filters 32R, 32G and 32B in the peripheral direction and further with a flange part 179 on the outer periphery. Even numbers of permanent magnets 180 are secured on the outer peripheral side of the above mentioned flange part 179.

On the top plate 181, bottom plate 182 and side plates not illustrated, hollow gaps are provided respectively in the positions corresponding to the above mentioned permanent magnets and iron cores 185 wound with coils 184 are provided in the gaps.

By such formation, a motor in which the rotary filter 178 having the above mentioned permanent magnets 180 is made a rotor and the iron cores 185 wound with the coils 184 are made stators can be formed.

According to this embodiment, as the motor projecting rearward of the housing 173 can be provided within the housing 173, the filter part can be made smaller than in the fourth embodiment.

The other formations and operations are the same as in the fourth embodiment.

Figure 20:
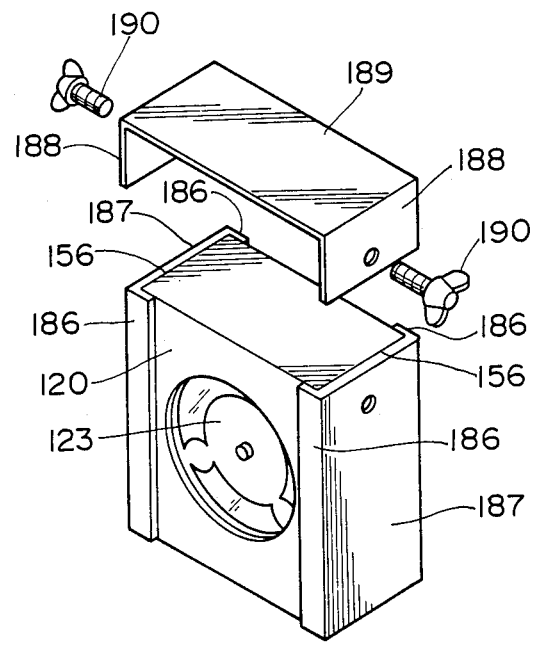
FIG. 20 is an explanatory view showing a modification of a fitting method of the fourth embodiment.

FIG. 20 is an explanatory view showing a modification of the fitting method of the fourth embodiment.

In an aperture 119a provided on the control apparatus 1a, frame members 187 having flange parts 186 at both side ends as corresponding to the side plates 156 of the housing 120 are provided so that the housing 120 may be fitted in from above.

Above the above mentioned frame members 187, a fixing member 189 having flange parts 188 at both ends and formed so that the above mentioned frame members 187 and the housing 120 inserted in the frame members 187 may be positioned in the space between the flange parts 188 can be screwed and fixed to the housing 120 by winged bolts 190 passing through the flange parts 188 and frame members 187.

According to this modification, when the housing 120 is to be inserted, the frame members 187 will become guide member so that the housing 120 may be smoothly inserted.

FIGS. 21 to 29 show the sixth embodiment of the present invention.

Figure 22:
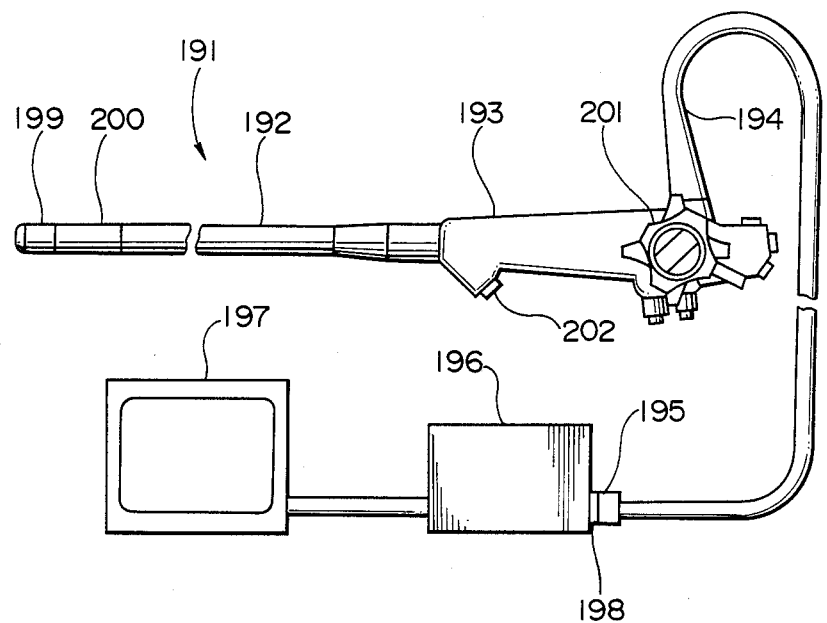

As shown in FIG. 22, an electronic endoscope 191 to be connected to the light source apparatus of this embodiment has an elongate, for example, flexible insertable part 192 to the rear end of which a thick operating part 193 is connected. A flexible cable 194 is extended sidewise from the rear end part of the above mentioned operating part 193 and is provided at the tip with a connector 195 which is to be connected with a connector receptacle 198 of a video processor 196 containing a light source apparatus and signal processing circuit and connectable with a monitor 197.

On the tip side of the above mentioned insertable part 192, a rigid tip part 199 and a curvable part 200 adjacent to this tip part 199 and curvable to the rearward side are provided in turn. By rotating and operating a curving operation knob 201 provided on the above mentioned operating part, the above mentioned curvable part 200 can be curved horizontally or vertically. The above mentioned operating part 193 is provided with an inserting part 202 communicating with a treating tool channel provided within the above mentioned insertable part 192.

Figure 24:
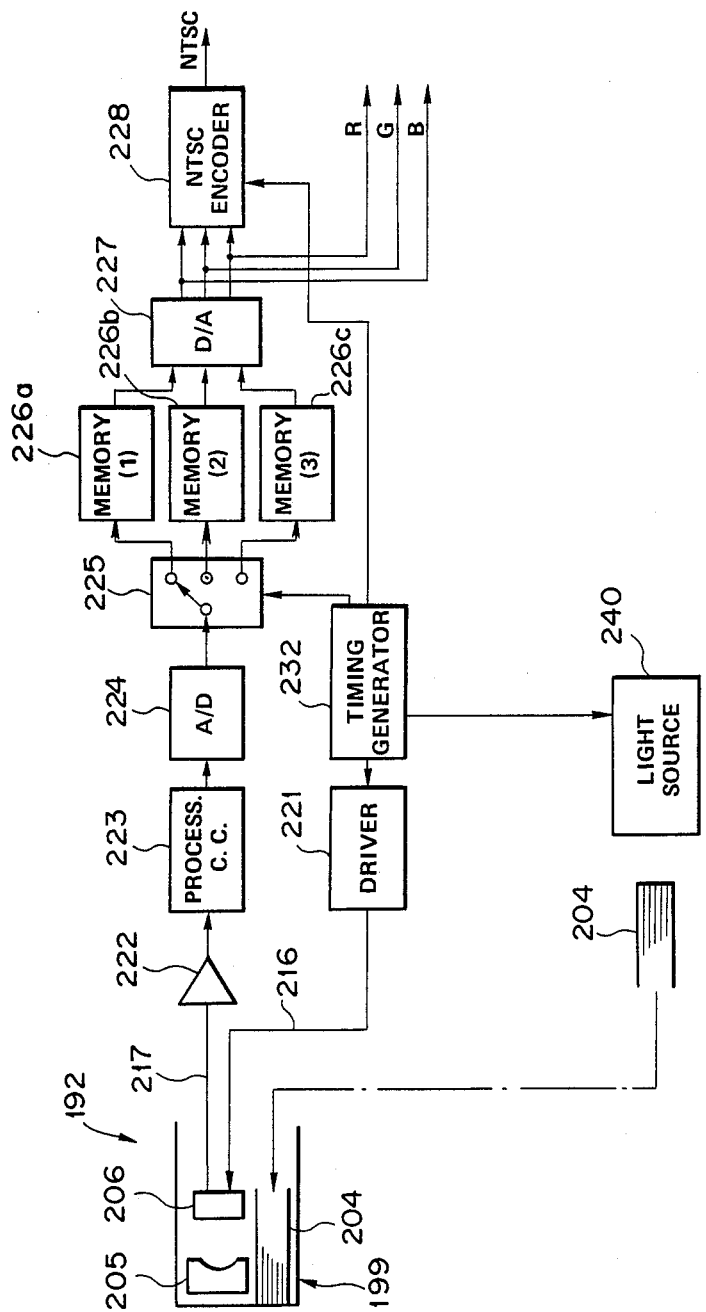

As shown in FIG. 24, a light guide 204 transmitting an illuminating light is inserted through the insertable part 192 of the electronic endoscope 191. The tip surface of this light guide 204 is arranged in the tip part 199 of the insertable part 192 so that the illuminating light may be emitted from this tip part 199. The above mentioned light guide 204 is inserted on the entrance end side through the universal cord 194 and is connected to the connector 195. An objective lens system 205 is provided in the above mentioned tip part 199 and a solid state imaging device 206 is arranged in the image forming position of this objective lens system 205. Signal lines 216 and 217 are connected to the above mentioned solid state imaging device 206, are inserted through the above mentioned insertable part 192 and universal cord 194 and are connected to the above mentioned connector 195.

On the other hand, a light source apparatus 240 is provided within the video processor 196 so that the light emitted from this light source apparatus 240 will enter the entrance end of the light guide 204, will be led to the tip part 199 through this light guide 204 and will be emitted from this tip part 199 to illuminate a position to be observed.

The light returning from the observed position by this illuminating light will be made to form an image on the solid state imaging device 206 by the the objective lens system 205 and will be photoelectrically converted. A driving pulse from a driver circuit 221 within the above mentioned video processor 196 will be applied to this solid state imaging device 206 through the above mentioned signal line 216 and signals will be read out and transferred by this driving pulse. The video signal read out of this solid state imaging device 206 will be input into a pre-amplifier 222 provided within the the above mentioned video processor 196 or electronic endoscope 191. The video signal amplified by this pre-amplifier 222 will be input into the process circuit 223, will be subjected to such signal processes as a γ-correction and white balance and will be converted to a digital signal. This digital video signal will be selectively memorized in three memories (1) 226a, (2) 226b and (3) 226c corresponding to respective colors, for example, of red (R), green (G) and blue (B). The above mentioned memories (1) 226a, (2) 226b and (3) 226c will be simultaneously read out, will be converted to analogue signals, will be output as R, G and B color signals, will be input into an encoder 228 and will be output as an NTSC composite signal from this encoder 228.

The above mentioned R, G and B color signals or NTSC composite signal will be input into the color monitor 197 and the observed position will be color-displayed.

By various synchronous signals from a synchronous signal generating circuit 232, the respective circuits of the motor driver 215, driver circuit 221, selecting circuit 225 and encoder 228 will be synchronized.

Figure 21:
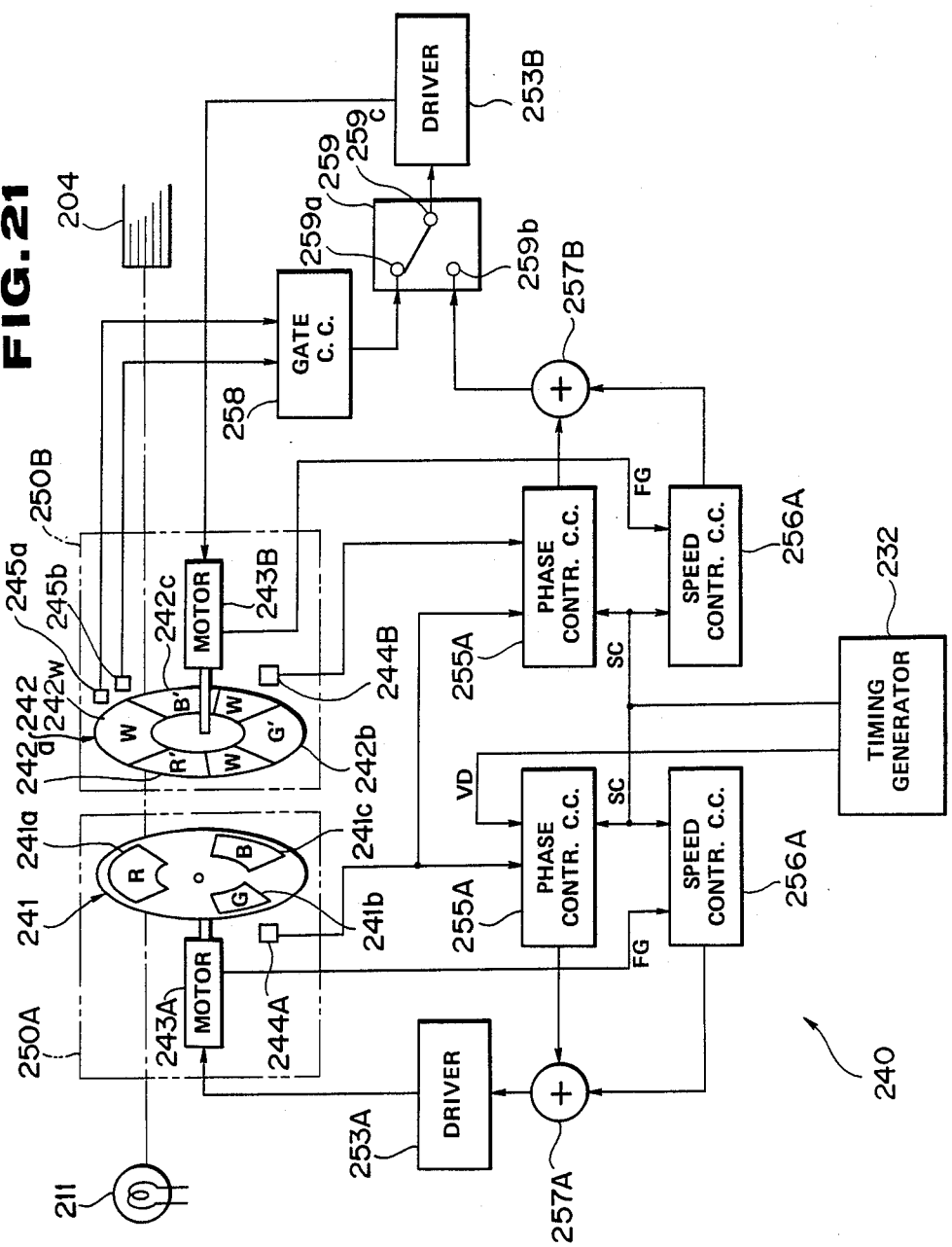
FIGS. 21 to 29 relate to the sixth embodiment of the present invention.

The above mentioned light source apparatus 240 is formed as shown in FIG. 21.

The above mentioned light source apparatus 240 is provided with a lamp 211 emitting a white color light. In the illuminating light path between this lamp 211 and the entrance end of the above mentioned light guide 204, there are arranged in the order from the lamp 211 side a first rotary filter 241 for ordinary observations and a second rotary filter 242 for special picture images. The respective rotary filters 241 and 242 are rotated respectively by motors 243A and 243B. Rotating position detecting photosensors 244A and 244B are arranged as opposed to the respective filters 241 and 242. Also, on the above mentioned second rotary filter 242 side, stopping position detecting photosensors 245a and 245b are arranged as opposed to this rotary filter 242.

Figure 25:
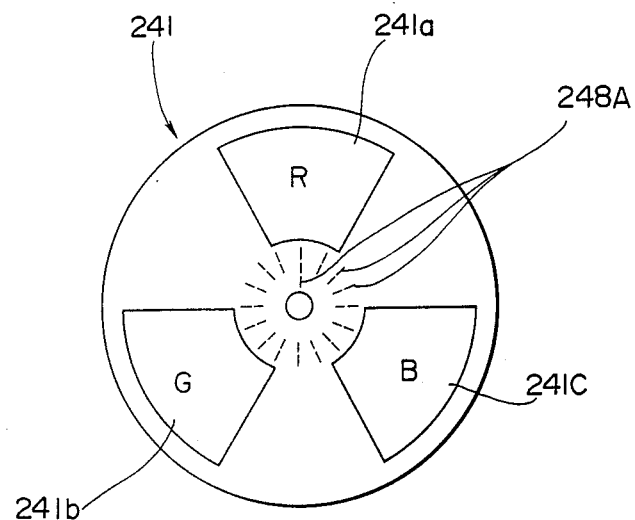
Figure 26:
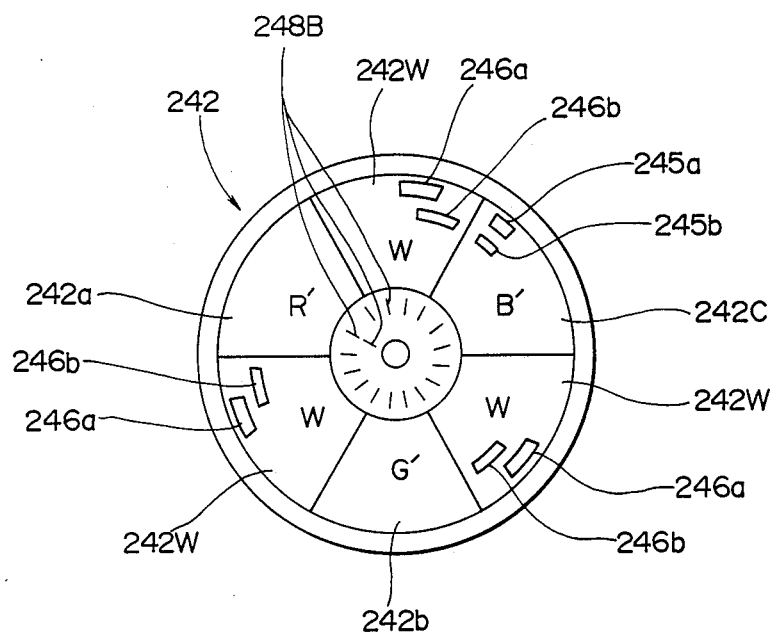

The above mentioned first rotary filter 241 and second rotary filter 242 are formed as shown respectively in FIGS. 25 and 26 which are views of the rotary filters as seen from the exit side.

Figure 27:
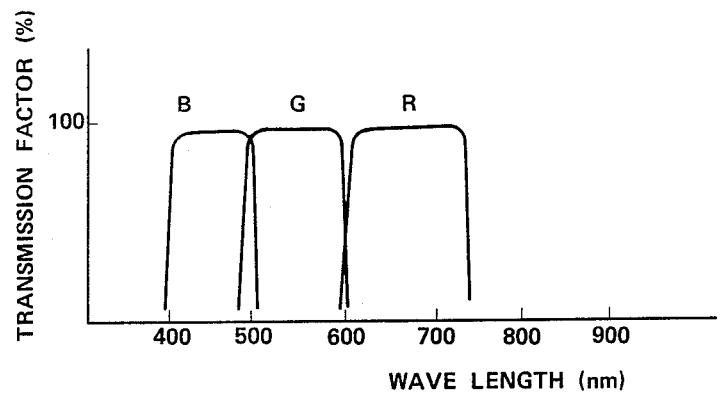

As shown in FIG. 25, in the first rotary filter 241, filters 241a, 241b and 241c transmitting the lights of the respective wavelength regions of red (R), green (G) and blue (B) are arranged in the peripheral direction. By the way, the respective wavelength regions of R, G and B are shown in FIG. 27. Rotating position detecting marks 248A are formed on the inner peripheral sides of the above mentioned respective filters 241a, 241b and 241c. The above mentioned photosensor 244A is to detect these marks 248A.

Figure 28:
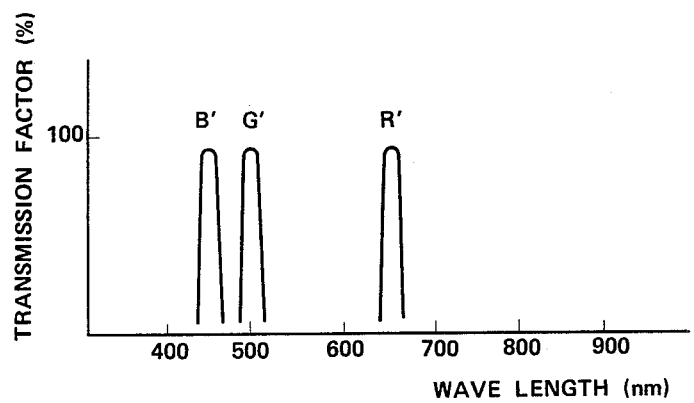

On the other hand, as shown in FIG. 26, in the second rotary filter 242, filters 242a, 242b and 242c transmitting the respective wavelength regions of narrow bands R', G' and B' are arranged in the peripheral direction and a white color light transmitting part 242W transmitting a white color light (W) is provided between the respective filters 242a, 242b and 242c. By the way, for example, as shown in FIG. 28, the respective wavelength regions of R', G' and B' are narrow bands having respectively 450, 500 and 650 nm as centers.

Reflecting plates 246a and 246b opposed respectively to the above mentioned photosensors 245a and 245b are provided in the outer peripheral parts of the respective white color light transmitting parts 242W. As shown in FIG. 26, the above mentioned photosensors 245a and 245b are arranged so that the photosensor 245a may be outside in the radial direction with respect to the above mentioned second rotary filter 242. On the other hand, the above mentioned reflecting plates 246a and 246b are so arranged that the outside reflecting plate 246a may be displaced in the counter-clockwise rotating direction with respect to the inside reflecting plate 246b. Rotating position detecting marks 248B are formed on the inner peripheral side of the above mentioned respective filters 242a, 242b and 242c so as to be detected by the above mentioned photosensor 244B.

Figure 23:
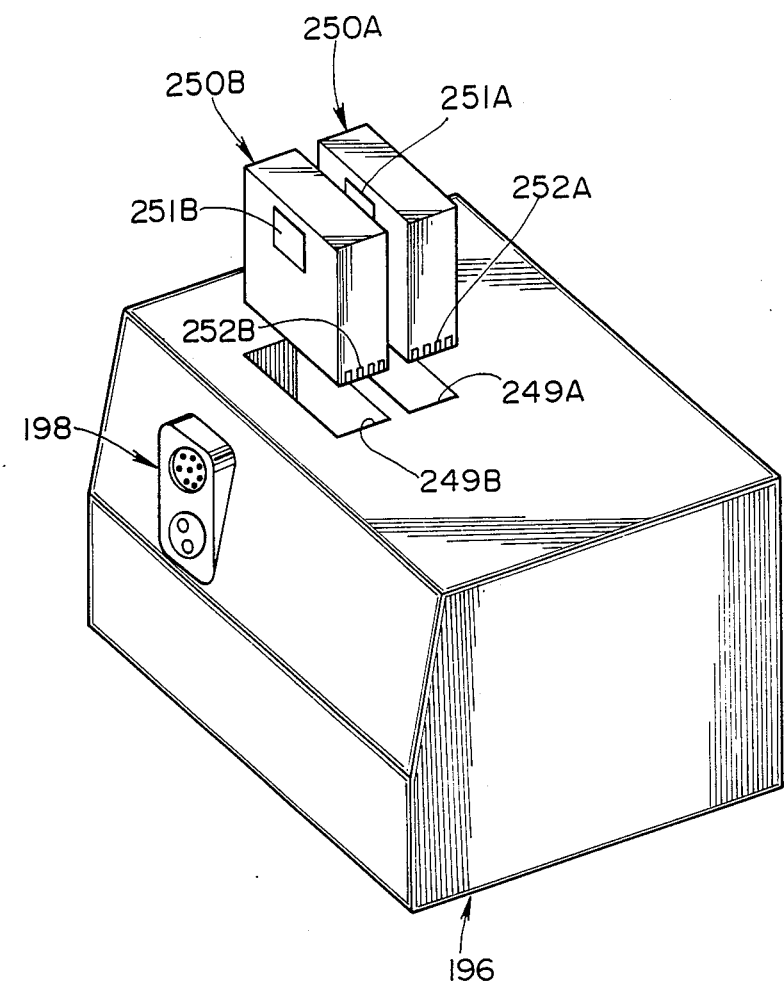

In this embodiment, the above mentioned first rotary filter 241, motor 243A and photosensor 244A are contained in the filter cassette 150A and the above mentioned second rotary filter 242, motor 243B and photosensors 244B 245a and 245b are contained in the filter cassette 250B. As shown in FIG. 23, the respective filter cassettes 250A and 250B can be removably fitted to the light source apparatus 240 within the video processor 196 through apertures 249A and 249B provided, for example, on the upper surface of the video processor 196. The above mentioned filter cassettes 250A and 250B are provided respectively with windows 251A and 251B in the positions corresponding to the illuminating light path. The packages of the above mentioned filter cassettes 250A and 250B are provided on the outer peripheries respectively with electric contacts 252A and 252B for connecting the motors 243A and 243B and photosensors 244A and 244B and 245a and 245b with the circuit within the light source apparatus 240.

As shown in FIG. 21, the above mentioned light source apparatus 240 is provided within it with a driver 253A driving the above mentioned motor 243A. The output of a phase controlling circuit 255A and the output of a speed controlling circuit 256A are added together by an adder 257A and are input to this driver 253A. A phase signal from the photosensor 244A and a vertical synchronous signal VD and subcarrier SC from the synchronous signal generating circuit 232 as reference signals are input into the above mentioned phase controlling circuit 255A whereby a phase signal from the photosensor 244A and the reference signals are compared in the phase with each other to output a signal corresponding to the phase difference. A speed signal FG from a speed sensor not illustrated provided in the above mentioned motor 243A and the subcarrier SC from the synchronous signal generating circuit 232 as a reference signal are input into the above mentioned speed controlling circuit 256A whereby a signal corresponding to the speed difference from the reference speed is output. Thus, the first rotary filter 241 is controlled and rotated by a phase synchronizing control combined with a speed control.

In the same manner, the above mentioned light source apparatus 2401 is provided within it with a driver 253B driving the above mentioned motor 243B. One side of the output of a gate circuit 258 into which the output of the adder 257B adding the output of the phase control circuit 255B and the output of the speed controlling circuit 256B together and the outputs of the photosensor 245a and 245b are input is selectively input through a switch 259. That is to say, the switch 259 of two inputs is connected at one input end 259a with a gate circuit 258, at the other input end 259b with the adder 257B and at the output end 259c with the driver 253B. The phase signal from the photosensor 244B and the phase signal from the above mentioned photosensor 244A and subcarrier SC from the synchronous signal generating circuit 232 ad reference signals are to be input into the above mentioned phase controlling circuit 255B. This phase controlling circuit 255B compares in the phase the phase signal from the photosensor 244B and the reference signal with each other and outputs a signal corresponding to the phase difference. The speed signal FG from a speed sensor not illustrated provided in the above mentioned motor 243B and subcarrier SC from the synchronous signal generating circuit 232 as a reference signal are to be input into the above mentioned speed controlling circuit 256B which is to output a signal corresponding to the speed difference from the reference speed. Therefore, in case the input end 259b side is selected by the above mentioned switch 259, the second rotary filter 242 will be rotated as synchronized in the phase with the first rotary filter. By the way, in this case, the phase will be controlled so that the respective filters 242a, 242b and 242c transmitting the R', G' and B' of the second rotary filter 242 may overlap the respective filters 241a, 241b, and 241c transmitting the R, G and B of the first rotary filter 241.

On the other hand, in case the input end 259a side is selected by the above mentioned switch 259, the above mentioned second rotary filter 242 will be stopped in the position in which the white color light transmitting part 242W is interposed in the illuminating light path.

The operation of the above mentioned gate circuit 258 shall be explained with reference to FIG. 26. In case the photosensor 245a detects the reflecting plate 246a and the photosensor 245b does not detect the reflecting plate 246b, this gate circuit 258 will output a signal clockwise rotating the rotary filter 242. In case the photosensor 245a does not detect the reflecting plate 246a and the photosensor 245b detects the reflecting plate 246b, a signal counterclockwise rotating the rotary filter 242 will be output. In case both photosensors 245a and 245b detect the reflecting plates 246a and 246b, a signal stopping the rotary filter 242 will be output. In case both photosensors 245a and 245b do not detect the reflecting plates 246a and 246b, a signal clockwise rotating the rotary filter 242 will be output. For example, in case the rotary filter 242 counterclockwise rotates, when the input end 259a side of the switch 259 is selected, first, only the photosensor 245a will detect the reflecting plate 246a and, therefore, the gate circuit 258 will output a signal clockwise rotating the rotary filter 242. In case the rotary filter 242 is thereby decelerated and both photosensors 245a and 245b stop in the position of detecting the reflecting plates 246a and 246b, the rotary filter 242 will be held in that position. In case the stopping position is passed, only the photosensor 245b will detect the reflecting plate 246b and the rotary filter 242 will be counterclockwise rotated and will be again returned to the stopping position. Thus, the rotary filter 242 will be stopped in the predetermined position, that is, the position in which the white color light transmitting part 242W is interposed in the illuminating light path.

In this embodiment formed as in the above, in the case of making an ordinary observation, when the first rotary filter 241 is rotated as controlled in the phase and the input end 259a side of the switch 259 is selected, the second rotary filter 242 will stop in the position in which the white light transmitting part 242W is interposed in the illuminating path. Therefore, the light emitted from the lamp 211 will be separated by the first rotary filter 241 into the lights of the respective wavelength regions of R, G and B in time series, will pass through the white light transmitting part 242W of the second rotary filter 242 and will enter the entrance end of the light guide 204. These lights of R, G and B will be transmitted to the tip part 299 through the light guide 204 to be radiated onto an object to be imaged. The light returning from the object by the frame sequential illuminating lights of R, G and B in this visible band will be made to form an object on the solid state imaging device 206 by the objective lens system 205 and an object image will be imaged by this solid state imaging device. Therefore, an ordinary visible picture image will be color-displayed in the monitor 197.

On the other hand, in the case of observing a special picture image by the wavelength regions of R', G' and B', when the first rotary filter 241 is rotated as controlled in the phase and the input end 259b side of the switch 259 is selected, the second rotary filter 242 will be rotated as controlled in the phase so that the respective filters 242a, 242b and 242c transmitting R', G' and B' may overlap the respective filters 241a, 241b and 241c transmitting R, G and B of the first rotary filter 241. Therefore, the light emitted from the lamp 211 will be separated in time series into the lights of the respective wavelength regions of R, G and B in the first rotary filter 241 and these lights of R, G and B will pass respectively through the filters 242a, 242b and 242c of the second rotary filter 242, will be limited to be of wavelength regions of R', G' and B' and will enter the entrance end of the light guide 204. In this case, picture images by the wavelength regions of R', G' and B' will be quasi color-displayed in the monitor 197.

Figure 29:
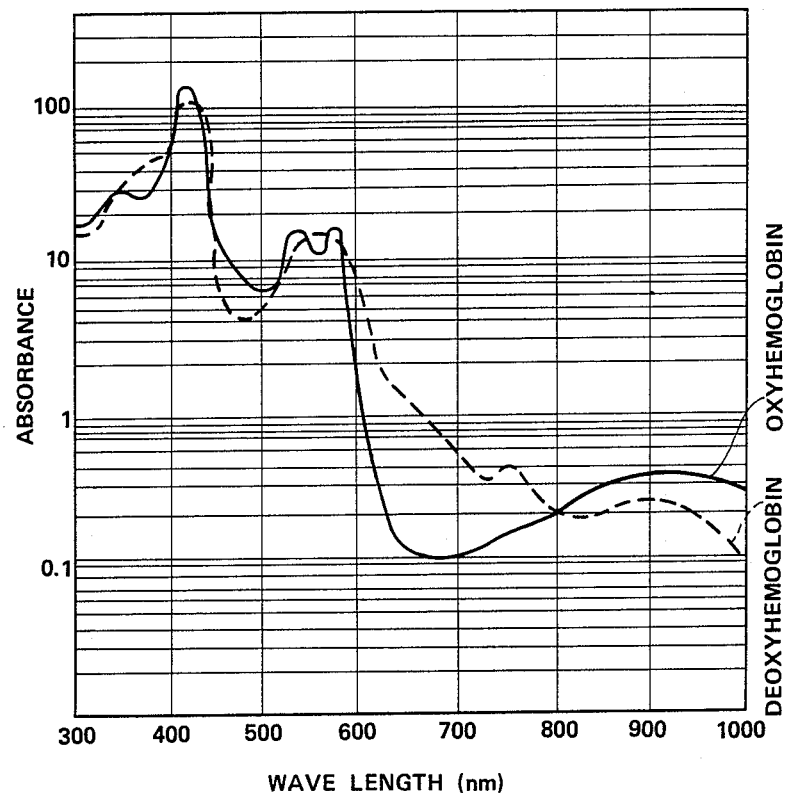

As shown in FIG. 29, the difference in the light absorbance of hemoglobin is so large between near 500 nm and near 650 nm that the variation of the amount of hemoglobin can be observed by the picture images of G' and R'.

When such region in which the light absorbance of blood varies little with the variation of the oxygen saturated degree (which shall be mentioned as $SO_2$ hereinafter) of hemoglobin as, for example, near 450 nm and such region in which the light absorbance of blood varies with the variation of $SO_2$ as, for example, near 530 nm are set as narrow band wavelength regions of the second rotary filter 242, the variation of $SO_2$ will be able to be observed by the picture images of these both wavelength regions.

By the way, the opening angle of the white color light transmitting part 242W of the above mentioned second rotary filter 242 is set to be of such size that, in case the first rotary filter 241 and second rotary filter 242 are rotated as controlled in the phase, the white color light transmitting part 242W of the second rotary filter 242 may not overlap the respective filters 241a, 241b and 241c.

Thus, according to this embodiment, when the rotation and stop of the second rotary filter 242 are switched over to each other, a frame sequential light for ordinary observations and a frame sequential light for ordinary observations and a frame sequential light for special picture images will be able to be fed as switched over to each other without replacing the rotary filters.

As both of the first rotary filter 241 and second rotary filter 242 are removably contained respectively in the filter cassettes 250A and 250B, a switchable combination can be freely selected by preparing various filter cassettes.

When both filter cassettes 250A and 250B are removed from the light source apparatus 240, a white color light will be able to be output and will be able to feed an illuminating light adapted to such endoscope with which a naked eye observation can be made and to an endoscope having a simultaneous type imaging means.

By the way, a plurality of second rotary filters 242 may be provided so that not less than three kinds of frame sequential lights may be fed. In such case, any desired rotary filter among a plurality of second rotary filters may be rotated as synchronized in the phase with the first rotary filter and the other rotary filters may be stopped in the position in which the white color light transmitting part is interposed in the illuminating light path.

By the way, the white color light transmitting part 242W of the second rotary filter 242 may be a hole.

Figure 30:
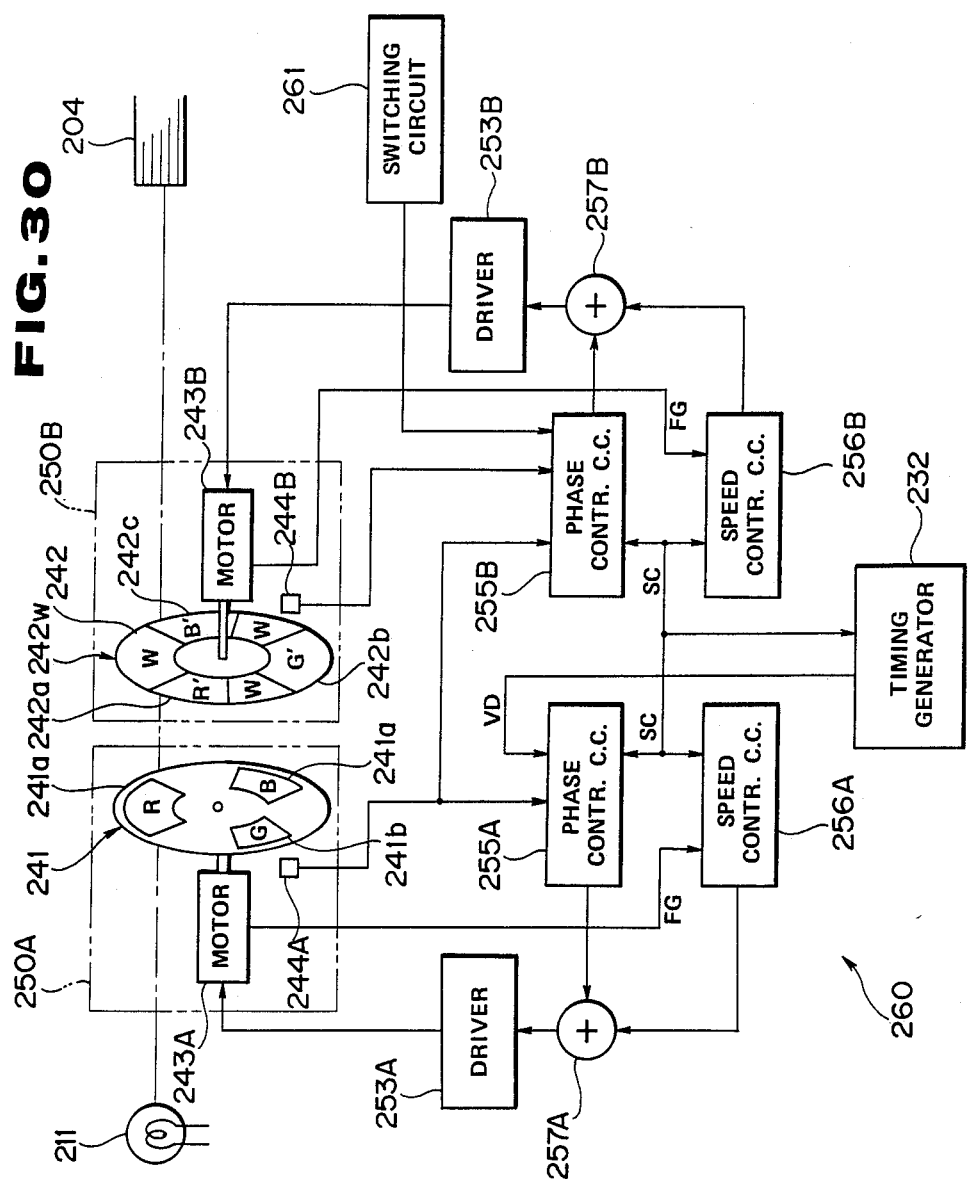
FIG. 30 is an explanatory view showing a light source apparatus of the seventh embodiment of the present invention.

FIG. 30 is an explanatory view showing a light source apparatus of the seventh embodiment of the present invention.

In the light source apparatus 260 of this embodiment, the second rotary filter 242 is not provided with the stopping position detecting reflecting plates 246a and 245b detecting these reflecting plates 246a and 246b. The gate circuit 258 and switch 259 are also not provided and the adder 257 B is connected directly to the driver 253B. A switching circuit 261 switching the phase of the second rotary filter 242 for the first rotary filter is provided for the phase controlling circuit 255B for the second rotary filter 242.

The other formations are the same as in the sixth embodiment.

In this embodiment, the second rotary filter 242 is rotated as always synchronized in the phase with the first rotary filter 241 but the phase of the second rotary filter 242 for the first rotary filter 241 can be switched. When the second rotary filter 242 is controlled in the phase so that the respective filters 242a, 242b and 242c transmitting R', G' and B' may overlap the respective filters 241a, 241b and 241c transmitting R, G and B of the first rotary filter 241, frame sequential lights of R', G' and B' will be output. On the other hand, when the second rotary filter 242 is controlled in the phase so that the three white color light transmitting parts 242W may overlap the respective filters 241a, 241b and 241c transmitting R, G and B of the first rotary filter 241, ordinary R, G and B field sequential lights will be output.

Thus, according to this embodiment, the formation is more simplified and the field sequential light for ordinary observations and the field sequential light for special picture images can be switched over to each other more quickly.

The other operations and effects are the same as in the sixth embodiment.

Figure 31:
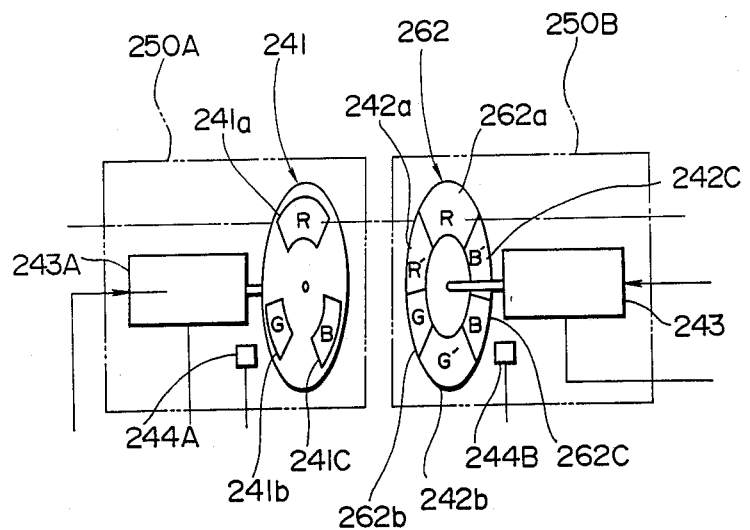
FIG. 31 is an explanatory view showing a rotary filter in a light source apparatus of the eighth embodiment of the present invention.

FIG. 31 is an explanatory view showing a rotary filter in a light source apparatus of the eighth embodiment of the present invention.

In this embodiment, in the second rotary filter 262 filters 262a, 262b and 262c transmitting respectively R, G and B are provided in the positions of three white color light transmitting parts 242W of the rotary filter 242 in the second embodiment.

In this embodiment, when the second rotary filter 262 is controlled in the phase so that the respective filters 242a, 242b and 242c transmitting respectively R', G' and B' may overlap the respective filters 241a, 241b and 241c transmitting respectively R, G and B of the first rotary filter 241, frame sequential lights of R', G' and B' will be output. On the other hand, when the second rotary filter 262 is controlled in the phase so that the respective filters 262a, 262b and 262c transmitting respectively R, G and B may overlap the respective filters 241, 241b and 241c transmitting respectively R, G and B of the first rotary filter 241, ordinary R, G and B field sequential lights will be output.

The other formations, operations and effects are the same as in the seventh embodiment.

By the way, in the sixth to eighth embodiments, for example, only the rotary filter may be contained in the filter cassette and the motor and others may be fixed within the light source apparatus. Also, the rotary filter may be fixed within the light source apparatus. This invention can be applied not only to an endoscope receiving the reflected light of the observed body but also to an endoscope for observing by receiving the light transmitted through the observed object. Further, it can be applied not only to an electronic endoscope having a solid state imaging device in the tip part of the insertable part but also to such endoscope apparatus wherein a television camera is used as connected to the eyepiece part to enable a naked observation or as replacing the above mentioned eyepiece part as a fiber scope.

FIG. 32 to 43 show the ninth embodiment of the present invention.

Figure 32:
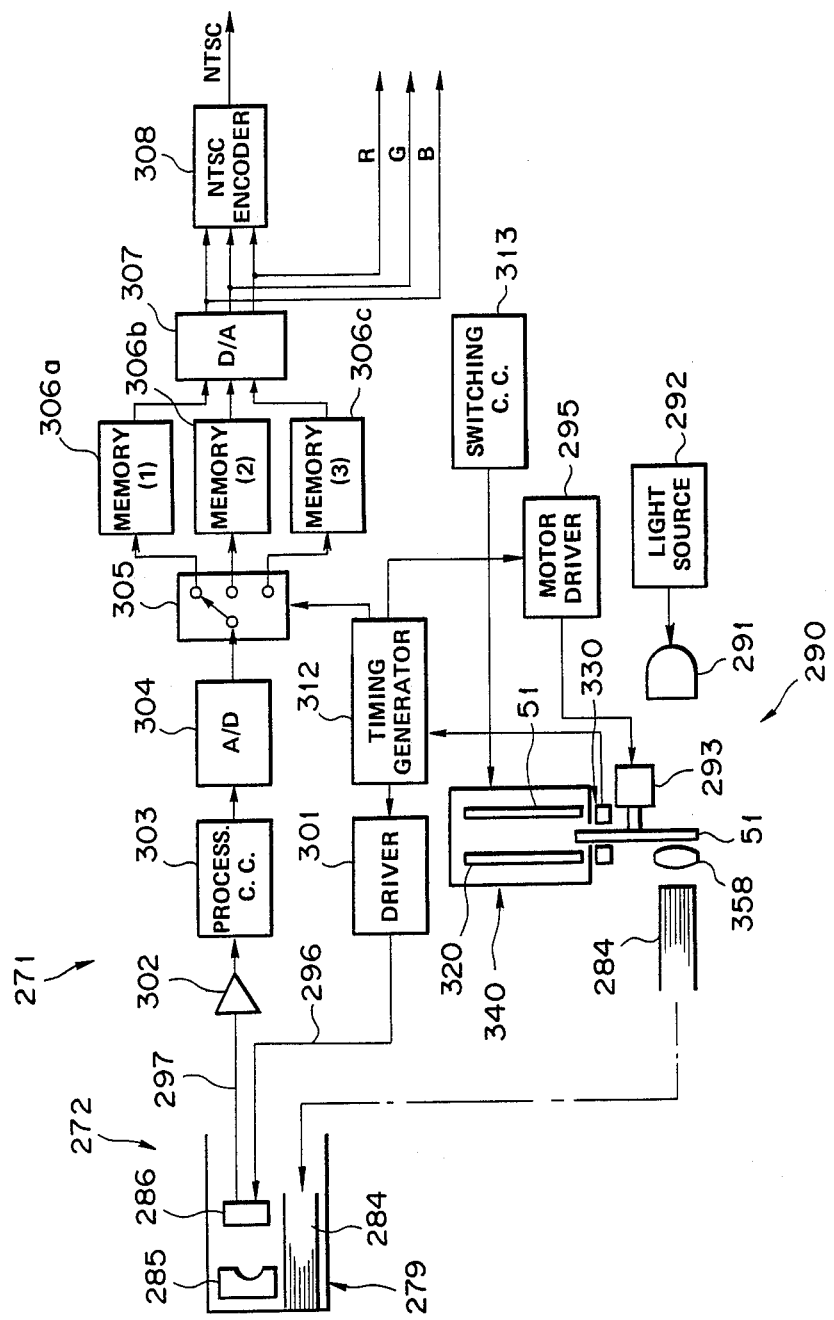

As shown in FIG. 32, a light guide 284 transmitting an illuminating light is inserted through an insertable part 272 of an electronic endoscope 271. The tip surface of this light guide 284 is arranged in the tip part 279 of the insertable part 272 so that an illuminating light may be emitted out of this tip part 279. Also, in the above mentioned tip pat 279, an objective lens system 285 is provided and a solid state imaging device 286 is arranged in the image forming position of this objective lens system. This solid state imaging device 286 has a sensitivity in a wide wavelength range from the ultraviolet region to the infrared region and including the visible region. Signal lines 296 and 297 are connected to the above mentioned solid state imaging device 286 and are connected to the respective circuits within the video processor 276. On the other hand, a light source apparatus 290 provided within the video processor 276 is provided with a lamp 291 emitting a light in a wide band from the ultraviolet light to the infrared light. This lamp 291 may be a general xenon lamp or strobo-lamp. The above mentioned xenon lamp or strobo-lamp emits a large amount of not only the visible light but also the ultraviolet light and infrared light. This lamp 291 is to be fed with an electric power by a power source part 292. A plurality (3 in the drawing) of filter cassettes 3201 are provided forward of the above mentioned lamp 291 and are to be selectively inserted in the illuminating light path by a filter cassette changer 340 which is controlled by a control signal from a switching circuit 313. Each filter cassette 320 has a rotary filter 321 so that, when it is inserted in the illuminating light path, the above mentioned rotary filter 321 will be connected to a motor 293 and will be rotated by this motor 293 which is driven as controlled in the rotation by a motor driver 295.

Figure 33:
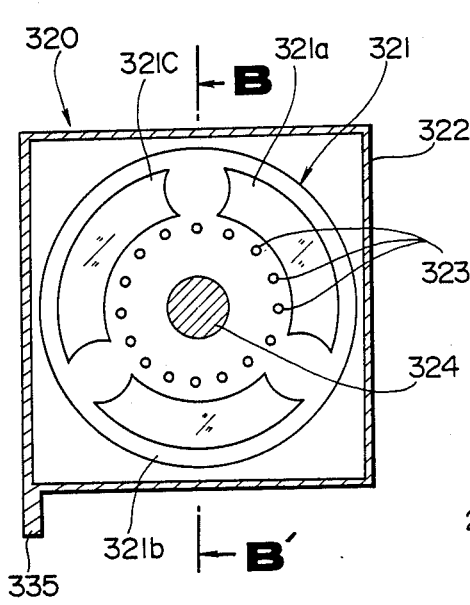
FIGS. 32 to 43 relate to the ninth embodiment of the present invention.
Figure 34:
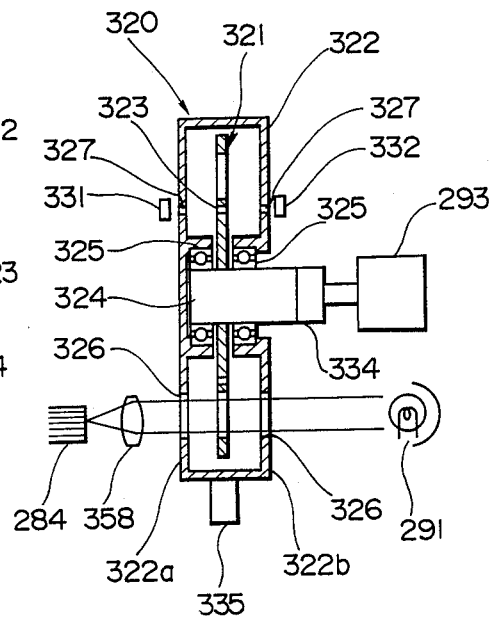

The formation of the above mentioned filter cassette 320 shall be explained by using FIGS. 33 and 34.

As shown in FIG. 33, in the rotary filter 321, three filters 321a, 321b and 321c are arranged in the peripheral direction. In the case of a rotary filter for ordinary observations, the above mentioned respective filters 321a, 321b and 321c will be such filters transmitting lights of respective wavelength regions of red (R), green (G) and blue (B) as are shown in FIG. 27 in the sixth embodiment. On the inner peripheral side of the above mentioned respective filters 321a, 321b and 321c, a plurality of holes 323 for detecting the rotating position of the rotary filter 321 are arranged in the peripheral direction. Also, as shown in FIG. 34, the above mentioned rotary filter 321 is contained within the housing 322 of the filter cassette 320. The rotary shaft 324 of the rotary filter 321 is rotatably borne by ball bearings 325 provided in the central part of the above mentioned housing 322.

On the front surface plate 322a and back surface plate 322b of the above mentioned housing 322, windows 326 are provided in the positions opposed to each other and to the respective filters 321a, 321b and 321c of the above mentioned rotary filter 321 so that the light emitted from the lamp 291 may pass through these windows 326 and respective filters 321a, 321b and 321c. Also, on the above mentioned front surface plate 322a and back surface plate 322b, windows 327 are provided in the positions opposed to each other and to the holes 323 for detecting the rotating position of the above mentioned rotary filter. A light emitting device 331 is arranged outside one window 327, a photosensor 332 is arranged outside the other window 327 and a rotary encoder 330 is formed of these light emitting device 331 and photosensor 332. That is to say, the light emitted from the light emitting device 331 and having passed through the holes 323 will be received by the photosensor 332 and the output of this photosensor 332 will be input into the timing generator 312 forming the timing of the entire system.

The rotary shaft 324 of the above mentioned rotary filter 321 is projected rearward from the back surface plate 322b side of the housing 322. On the other hand, a clutch 334 is provided at the end of the output shaft of the above mentioned motor 293 so that the rotary shaft 324 of the above mentioned rotary filter 321 and the output shaft of the motor 293 may be connected with each other through the above mentioned clutch 334.

A pawl 335 projecting below is provided at the end of the filter cassette changer 340 side in the bottom of the above mentioned housing 322.

Figure 6:
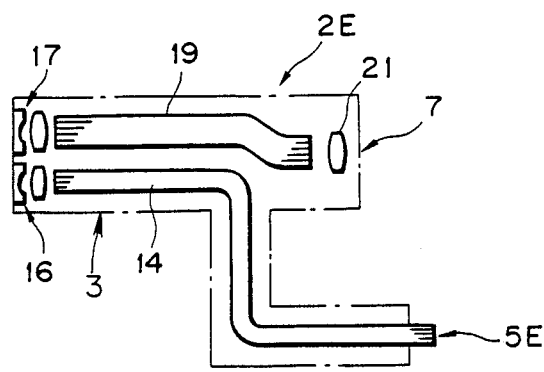

Not only a rotary filter for ordinary observations wherein filters having such transmitting characteristics as are shown in FIG. 6 in the sixth embodiment are arranged but also such rotary filters for special picture images as, for example, in the following are prepared for the above mentioned rotary filter 321.

Figure 39:
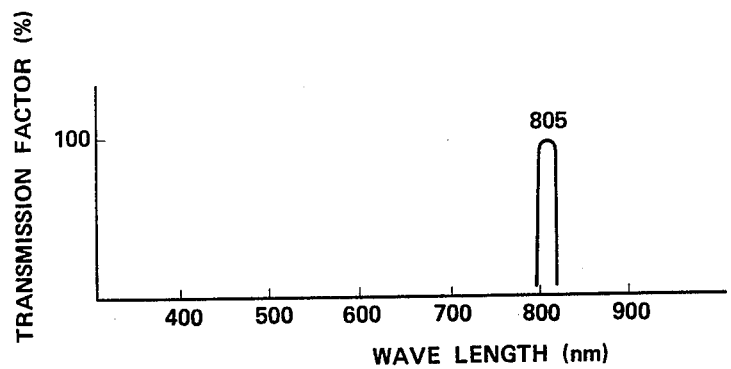

One of them is a rotary filter (which shall be called an 805 nm short wavelength type rotary filter hereinafter) wherein each of three filters 321a, 321b and 321c transmits such narrow band having 805 nm as a center as is shown in FIG. 39.

Figure 40:
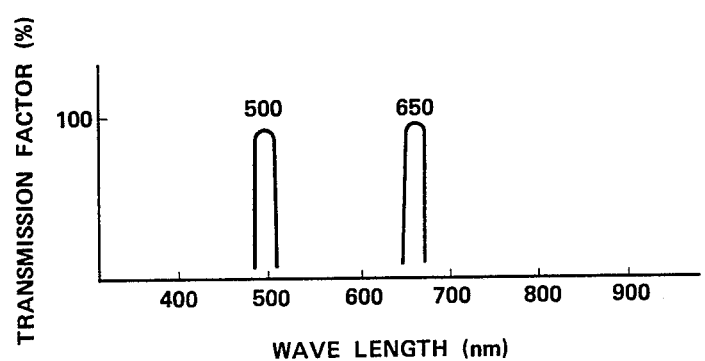

Another is a rotary filter (which shall be called a hemoglobin amount observing type rotary filter hereinafter) wherein two of the three filters 321a, 321b and 321c are a filter transmitting a narrow band having 500 nm as a center and a filter transmitting a narrow band having 650 nm as a center a shown in FIG. 40.

Figure 41:
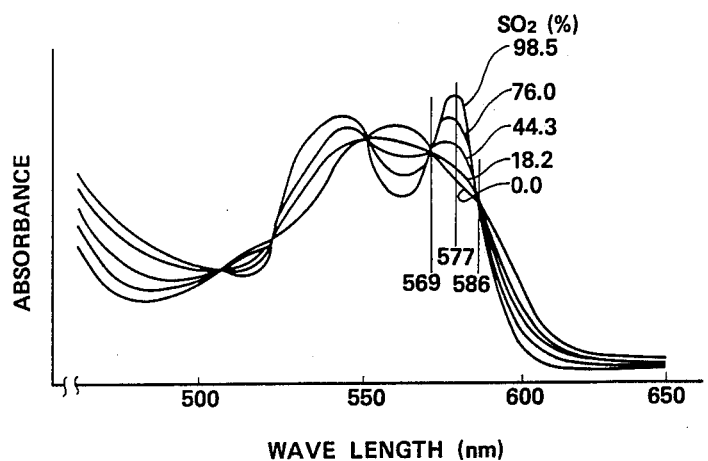

Further, another is a rotary filter (which shall be called an SO$_2$ observing type rotary filter hereinafter) wherein the wavelengths transmitted by the three filters 321a, 321b, and 321c are two of a wavelength varying the light absorbance of blood with the variation of the oxygen saturated degree (which shall be mentioned also as SO$_2$ hereinafter) of hemoglobin and a wavelength near that wavelength and little varying the light absorbance of blood with the variation of SO$_2$. FIG. 41 shows the variation of the light absorbance (dispersed reflected spectrum) of blood with the variation of SO$_2$ near 500 to 650 nm. As a transmitted wavelength range of the respective filters of the SO$_2$ observing type rotary filter in this band, there is selected, for example, a set of 569, 577 and 585 nm. By the way, the combination of the transmitted wavelength ranges of the respective filters of the SO$_2$ observing type rotary filter is not limited to the one shown in FIG. 41. FIG. 29 in the sixth embodiment shows the spectrum absorbing characteristics of oxyhemoglobin and deoxyhemoglobin. As understood from this diagram, some combinations of the transmitted wavelength ranges of the respective filters of the SO$_2$ observing type rotary filter, that is, of two wavelength ranges wherein the light absorbances of oxyhemoglobin and deoxyhemoglobin are substantially equal to each other and a wavelength range wherein the difference between the light absorbances of the oxyhemoglobin and deoxyhemoglobin is large can be selected.

Figure 42:
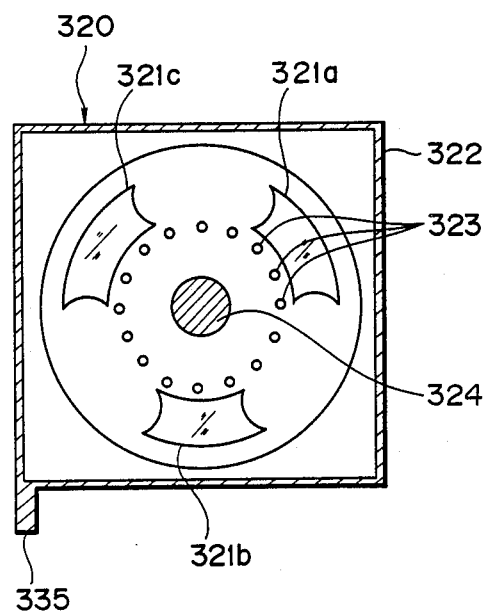

Further, as shown in FIG. 42, another is a rotary filter (which shall be called an opening angle varying type rotary filter hereinafter) which is for ordinary observations but in which the opening angles of the respective filters 321a, 321b and 321c of R, G and B are varied (an example of making the angles smaller is shown in FIG. 42).

Such various rotary filters 321 are contained respectively in the housings 322 of separate filter cassettes 320.

The formation of the above mentioned filter cassette changer 340 shall be explained in the following by using FIGS. 35 to 38.

Figure 35:
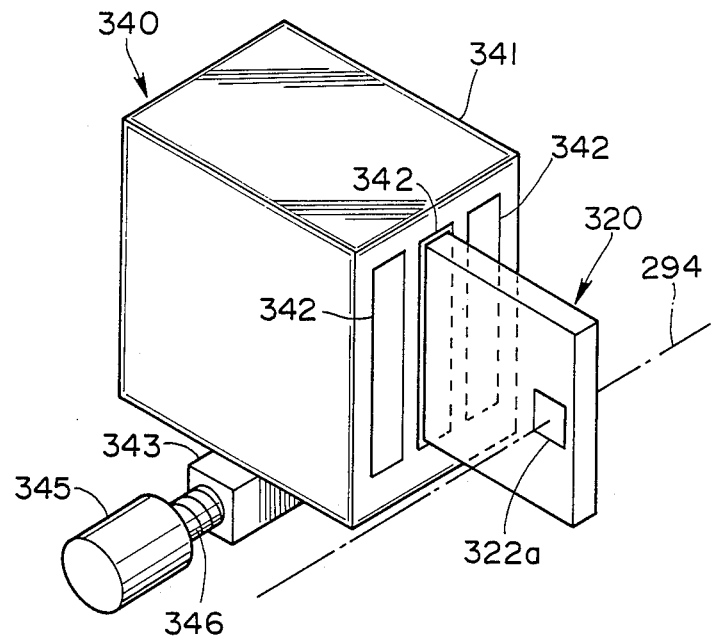
Figure 36:
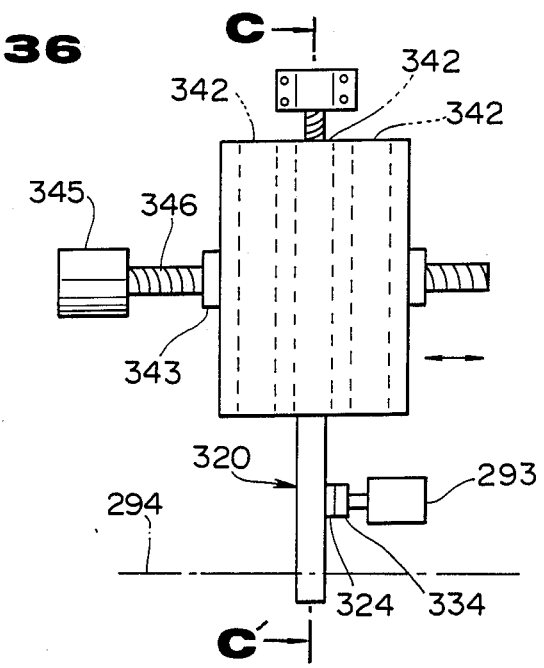
Figure 38:
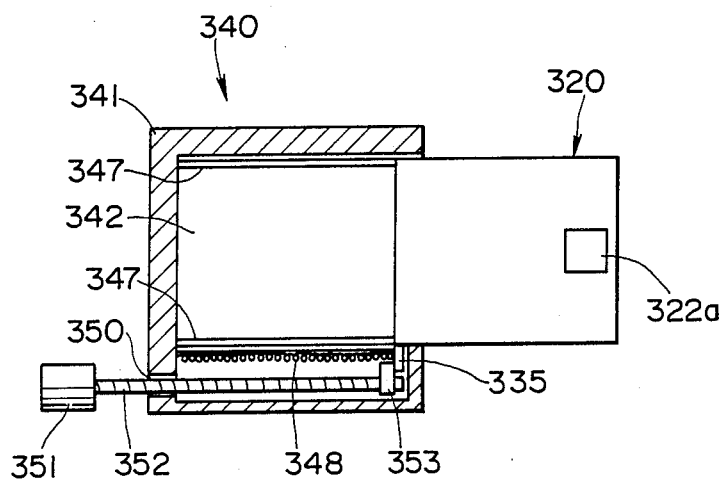

As shown in FIG. 35, the filter cassette changer 340 is provided with a cassette unit which can contain a plurality (three in the drawing) of filter cassettes 320. For example, three cassette containing parts 342 opening on the illuminating light path side shown by the optical axis 294 are formed in this cassette unit 341 and contain respectively the above described plurality of filter cassettes 320. A nut 343 arranged in parallel with the optical axis 294 of the illuminating light path is fitted to the bottom of the above mentioned cassette unit 341. A pipe screw 346 rotated by a cassette changing motor 345 is screwed into this nut 343. The above mentioned motor 345 is fixed in a predetermined position so as not to move. When the pipe screw 346 is rotated by the above mentioned motor 345, as shown in FIG. 36, the cassette unit 341 together with the nut 343 will be able to be moved forward and rearward in the direction parallel with the optical axis 294 of the illuminating light path. As shown in FIG. 38, rails 347 are provided in the upper part and lower part within each cassette containing part 342 of the above mentioned cassette unit 341 so that the above mentioned filter cassette 320 may move along these rails to be inserted in or removed from the illuminating light path. The pawl 335 of the above mentioned filter cassette 320 is projected below the lower rail 347. A tension spring 348 fixed at one end to the inner part of the cassette containing part 342 is fitted at the other end to this pawl 335 to energize the filter cassette 320 in the direction of containing it within the cassette containing part 342.

Figure 37:
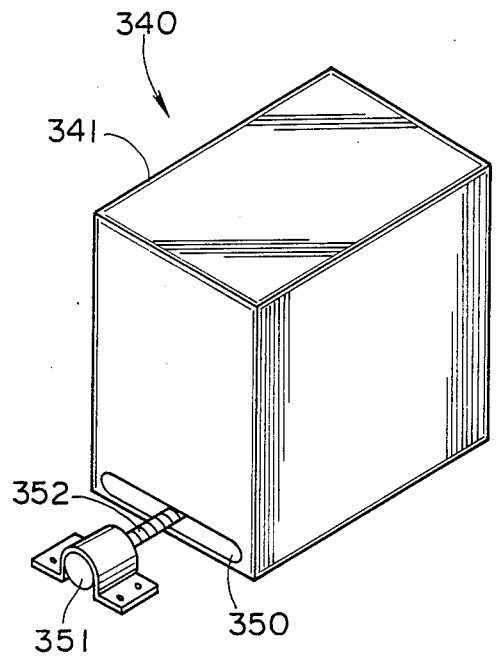

Also, as shown in FIG. 37, a slot 350 parallel with the optical axis 294 of the illuminating light path and communicating with all the cassette containing parts 342 is formed in the lower part on the opposite illuminating light path side surface of the above mentioned cassette unit 341. A pipe screw 352 arranged vertically to the above mentioned optical axis and rotated by a motor 351 is inserted in this slot 350. As shown in FIG. 38, a nut 353 is screwed to this pipe screw 352 within the cassette unit 341 and is regulated in the rotation to be moved by the rotation of the above mentioned pipe screw 352 and to contact the pawl 335 of the above mentioned filter cassette 320. The above mentioned motor 351 is fixed in a predetermined position so as not to move. When the pipe screw 352 is rotated by the above mentioned motor 351, the filter cassette 320 together with the nut 353 will be moved to be able to be inserted in or removed from the illuminating light path. By the way, in the case of moving the filter cassette 320 in the direction of retreating it from the illuminating light path, when the nut 353 is retreated, the filter cassette 320 will retreat under the tension of the spring 348.

The operation of the filter cassette changer 340 shall be explained in the following.

First of all, by rotating the motor 345, the cassette unit 341 is moved so that a desired filter cassette 320 may be brought to a movable position by the nut 353. Then, by rotating the motor 351, the nut 353 contacting the pawl 335 of the desired filter cassette 320 is advanced to the illuminating light path side and is pushed out. As a result, as shown in FIGS. 35 and 36, the filter cassette 320 will be arranged in the position in which the window 322a is interposed in the illuminating light path. In this state, the clutch 334 provided on the output shaft of the rotary filter rotating motor 293 will be connected to the rotary shaft 324 of the rotary filter 321. By the way, in the case of connecting the above mentioned clutch 334 to the rotary shaft 324, the motor 293 may be moved to the filter cassette 320 side or the clutch 334 and rotary shaft 324 may be connected with each other by utilizing a magnet.

Next, in the case of retracting the the filter cassette 320 from the illuminating light path, by rotating the motor 351, the nut 353 is retreated so that the filter cassette 3230 may be retreated by the tension of the spring 348 and may be contained in the cassette containing part 342.

As shown in FIG. 32, the light having passed through the rotary filter 321 of the filter cassette 320 selected by the above mentioned filter cassette changer 340 and interposed in the illuminating light path will be condensed by the condenser lens 358, will enter the entrance end of the light guide 284, will be led to the tip part 279 through this light guide 284 and will be emitted out of this tip part 279 to illuminate an observed position.

The light returning from the observed position by this illuminating light will be made to form an image on the solid state imaging device 286 and will be photoelectrically converted. A driving pulse from a driver circuit 301 within the above mentioned video processor 276 will be applied to this solid state imaging device 286 through the above mentioned signal line 296. Signals will be read out and transmitted by this driving pulse. The video signal read out of this solid state imaging device 286 will be input into a pre-amplifier 302 provided within the above mentioned video processor 276 or electronic endoscope 271 through the above mentioned signal line 297. The video signal amplified by this pre-amplifier 302 will be input into a process circuit 303, will be processed to be γ-corrected and white-balanced and will be converted to a digital signal by an A/D converter 304. This digital video signal will be selectively memorized by three of a memory (1) 306a, memory (2) 306b and memory (3) 306c corresponding to the respective colors, for example, of red (R), green (G) and blue (B). The above mentioned memory (1) 306a, memory (2) 306b and memory (3) 306c will be simultaneously read out, will be converted to analogue signals by a D/A converter 307, will be output as R, G and B color signals, will be separately input into an encoder 308 and will be output as an NTSC composite signal out of this encoder 308.

The above mentioned R, G and B color signals or NTSC composite signal will be input into the color monitor 277 by which the observed position will be color-displayed.

The respective circuits of the motor driver 295, driver circuit 301 and selecting circuit 305 will be synchronized by the above mentioned timing generator 312.

In this embodiment, when the filter cassette changer 340 is controlled by a switching circuit 313 and the filter cassette 320 containing the rotary filter 321 for ordinary observation is interposed in the illuminating light path, the light emitted from the above mentioned lamp 291 will sequentially pass through the filters 321a, 321b and 321c transmitting R, G and B of the rotary filter 321 for ordinary observations within this filter cassette 320 and will be divided in time series into the lights of the respective wavelength regions of R, G and B. These R, G and B lights will be transmitted to the tip part 279 through the light guide 284 and will be radiated onto the object. The light returning from the object by the frame sequential illuminating lights of R, G and B in this visible band will be made to form an image on the solid state imaging device 286 and the object will be imaged by this solid state imaging device 286. Therefore, an ordinary visible picture image will be color-displayed in the monitor 277.

On the other hand, when the filter cassette changer 340 is controlled by the above mentioned switching circuit 313 and the filter cassette 320 containing the other rotary filter 321 for special picture images is interposed in the illuminating light path, the following picture images will be obtained in response to the kinds of the rotary filter 321:

First of all, when the 805 nm single wavelength type rotary filter is selected, in all the timings of R, G and B, the light of the narrow band having 805 nm as a center will pass through this rotary filter and a picture image of the object in the narrow band having 805 nm as a center will be obtained. Now, the blood in which ICG (Indocyanine green) which is an infrared ray absorbing color is mixed has a maximum absorption at 805 nm. Therefore, when the above mentioned ICG is mixed into blood, for example, by a venous injection and the picture image of the object in the narrow band having 805 nm as a center is observe cancer of IIb and the running state of the vein below the mucous membrane will be able to be observed.

When the hemoglobin amount observing type rotary filter is selected, a picture image of the object in the narrow band having 500 nm as a center and a picture image of the object in the narrow band having 650 nm as a center will be obtained. As shown in FIG. 13, the difference in the light absorbance of blood is large between near 500 nm and near 650 nm. Therefore, the variation of the hemoglobin amount can be observed from the difference in the light absorbance between these two wavelength ranges.

In case the $SO_2$ observing type rotary filter is selected, picture images in the respective wavelength ranges of 569, 577 and 585 nm will be obtained. As shown in FIG. 41, 569 and 585 nm are wavelengths at which the light absorbance of blood will not substantially vary with the variation of $SO_2$ and 577 nm is a wavelength at which the light absorbance of blood will vary with the variation of $SO_2$. Therefore, the variation of $SO_2$ can be observed by the picture images in these three wavelength ranges.

In case the aperture angle varying type rotary filter in which the aperture angle is made smaller is selected, a picture image in which the deflection of each of R, G and B is small will be obtained. By the way, the color displacement among R, G and B can be corrected.

In case no filter cassette 3201 is interposed in the illuminating light path, a white color light will be able to be output and an illuminating light adapted to such endoscope whereby a naked eye observation can be made as a fiber scope and to an endoscope having a simultaneous type imaging means will be able to be fed.

Thus, according to this embodiment, when the filter cassette 320 to be interposed in the illuminating light path is switched by a filter cassette changer 340, a combination of frame sequential illuminating lights will be able to be selected from among a plurality of combinations. Therefore, various combinations of frame sequential illuminating lights different in the wavelength region or the like can be fed in response to the observed position and observed object. By these various combinations of frame sequential illuminating lights, there can be obtained such various picture images as an ordinary picture image, picture image showing a cancer or a vein running state, picture image showing the variation of a hemoglobin amount, picture image showing the variation of the oxygen saturated degree of hemoglobin and picture image in which the deflection of each of R, G and B is small.

Figure 43:
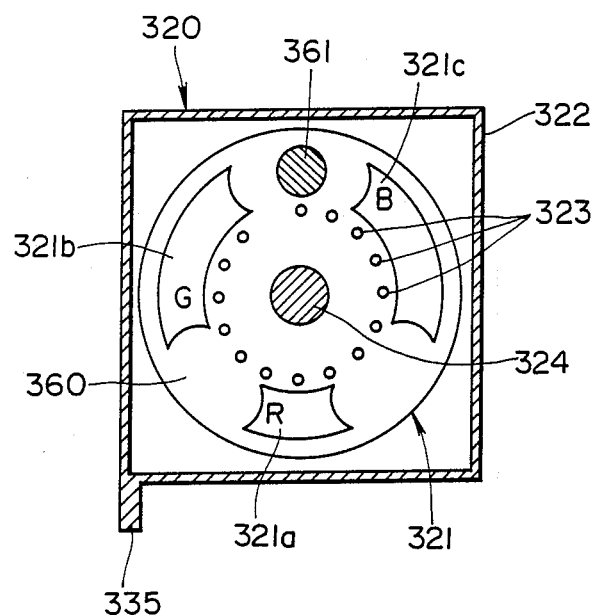

By the way, in the case of varying the aperture angles of the respective filters 321a, 321b and 321c of the rotary filter 321, in order to take the white balance or the like, the aperture angles of the respective filters of R, G and B need not be uniform and may be different, for example, as shown in FIG. 43. In the example shown in this drawing, the aperture angle of the filter 321a transmitting R is smaller than that of the other filter 321b transmitting G and filter 321c transmitting B.

Now, aluminum or the like is used for the frame 360 of the rotary filter 321 and glass or the like is used for the respective filters 321a, 321b and 321c. However, in case the specific gravities of the frame 360 and the respective filters 321a, 321b and 321c are different, when the aperture angles of the respective filters 321a, 321b and 321c are made different as shown in FIG. 43, the rotary filter 321 will be unbalanced. If such unbalanced rotary filter 321 is driven, it will be hardly stabilized and a feedback control will not operate.

Therefore, in the modification shown in FIG. 43, a balancer 361 is fitted to a part of the frame 360 of the rotary filter 321 so as to balance the rotary filter. The position and weight of the above mentioned balancer 361 are set in response to the position of the center of gravity or the like of the rotary filter 321 before fitting the balancer 361. In the example shown in FIG. 43, as the specific gravity of the frame 360 is larger than the specific gravity of the respective filters 321a, 321b and 321c, the center of gravity is deviated to the R transmitting filter 321a side from the rotation center and therefore the balancer 361 is fitted to the other side of this filter 321a. When the rotary filter 321 is thus balanced, the rotation of the rotary filter 321 will rise smoothly and will be stabilized.

By the way, the present invention is not limited to the above mentioned embodiment. For example, the rotary filter 321 may be provided with filters transmitting three different wavelength regions in the infrared band and ultraviolet band for the respective filters 321a, 321b and 321c. By such rotary filter, the object image in the infrared band and ultraviolet band can be observed. A filter cassette containing a filter always transmitting a predetermined light instead of the rotary filter may be provided.

The mechanism of replacing the filter cassette is not limited to the one shown in the embodiment. The number of replaceable filter cassettes is optional. The rotary filter may be made replaceable without being contained in the filter cassette.

The motor and rotary encoder together with the rotary filter may be provided within each filter cassette.

By the way, this embodiment can be applied not only to an endoscope wherein a reflected light of an observed object is received but also to an endoscope wherein a light having passed through the observed object is received to make an observation.

Also, this embodiment can be applied not only to an electronic endoscope having a solid state imaging device in the tip part of the insertable part but also to the eyepiece part of such endoscope whereby a naked eye observation can be made as a fiber scope or to an endoscope whereby a television camera is connected and used by replacing the above mentioned eyepiece part.

Figure 44:
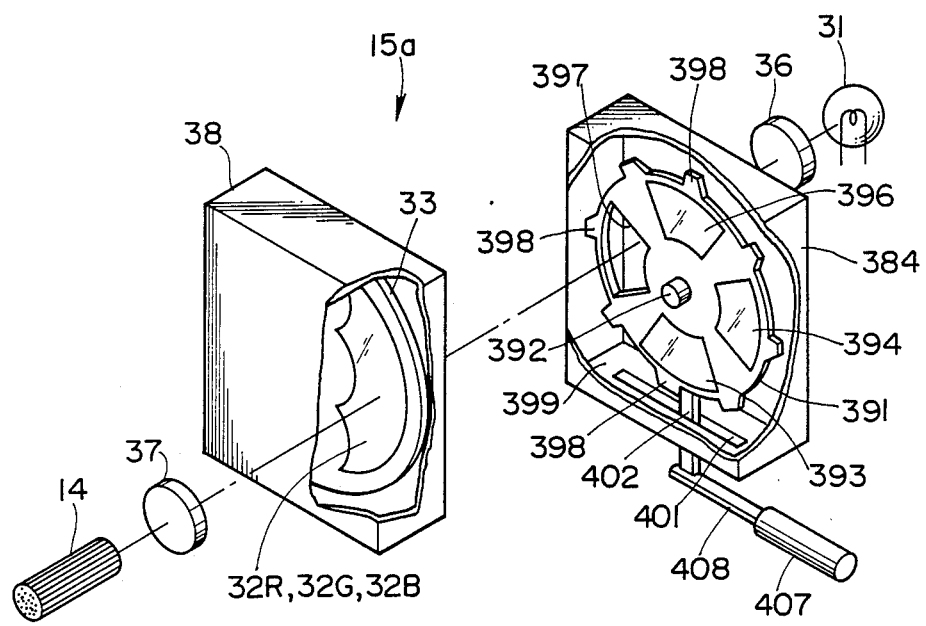
FIGS. 44 to 46 relate to the tenth embodiment.
Figure 45:
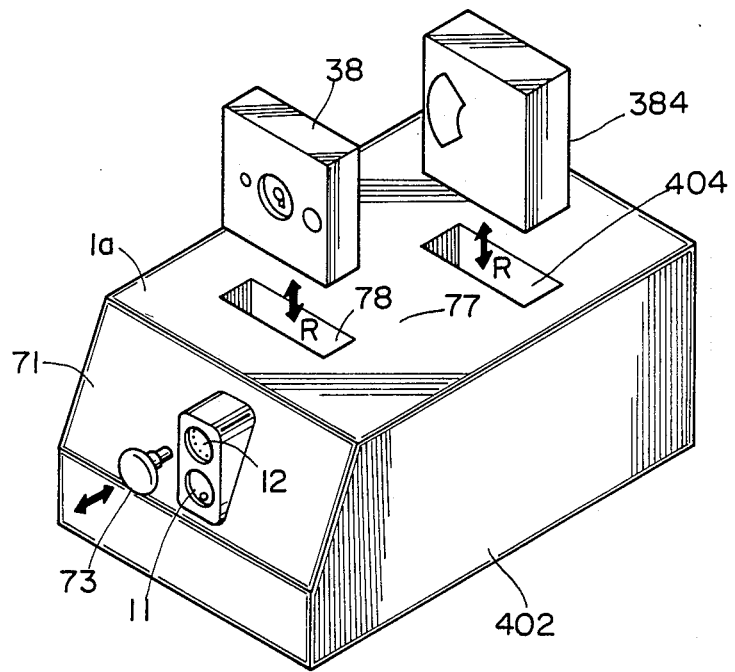
Figure 46:
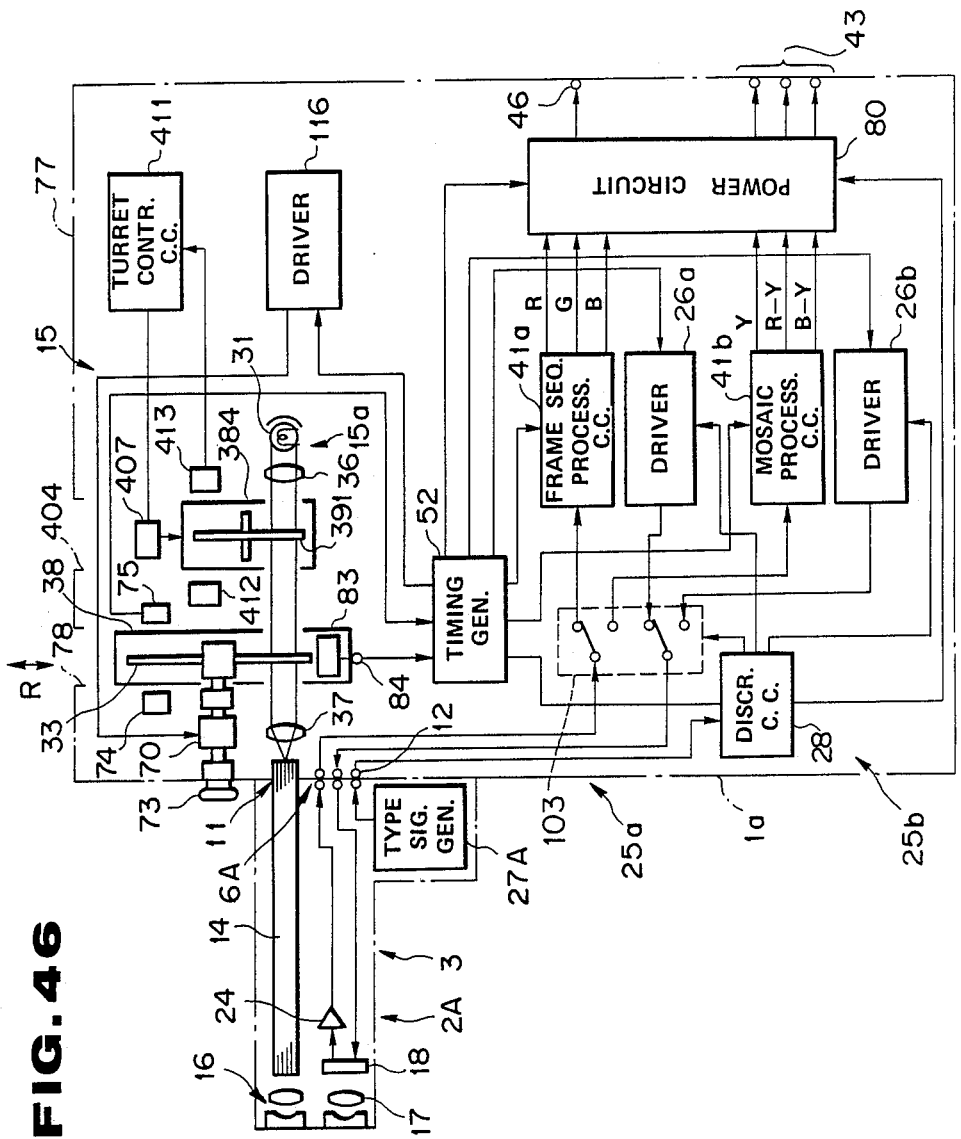
Figure 47:
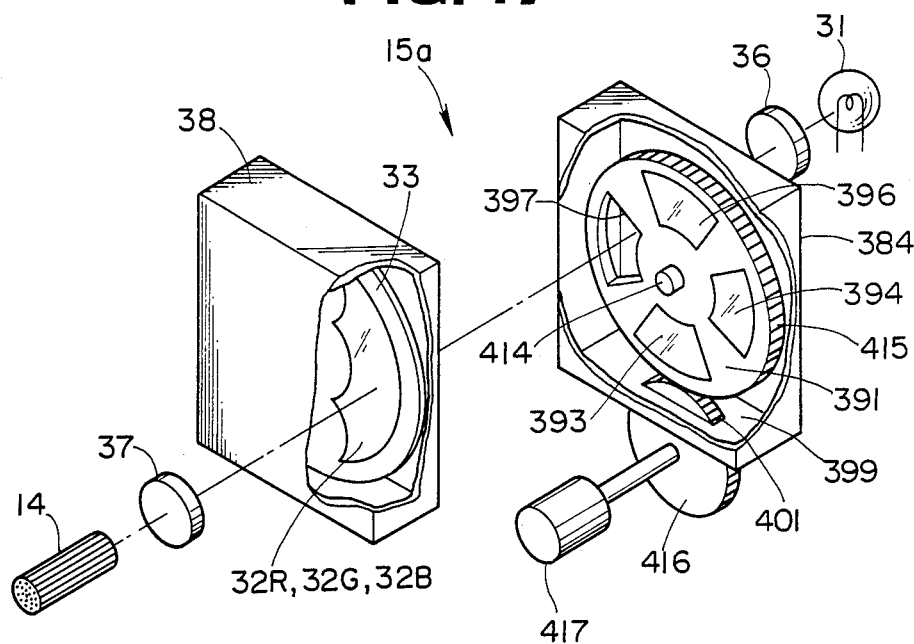
FIG. 47 relates to the 11th embodiment of the present invention and is a perspective view showing the formation of a light source part.

FIGS. 44 to 46 show the 10th embodiment of the present invention.

In a light source part 15a of a light source apparatus 15 in this embodiment, as in FIG. 44, in the light path connecting a light source lamp 31 emitting a white color light with the entrance light source lamp 31 is made a parallel light, a turret cassette 384 as a wavelength region selecting means which can select the wavelength range of this illuminating light made parallel, a filter cassette 38 as a color separating means to be inserted and fitted in case a frame sequential type electronic scope 2A and frame sequential type television camera 8C are connected to the light source apparatus 15 and a condenser lens 37 condensing the illuminating light emitted from this filter cassette 38.

A rotary filter 33 is of the same formation as in FIG. 8 in the first embodiment, is disc-like and has filters 32R, 32G and 32B transmitting three primary colors of red (R), green (G) and blue (B) in the peripheral direction on the disc surface so that a white color light emitted from a light source lamp 31 may be made illuminating lights of respective wavelengths of red, green and blue and an illuminating light adapted to the frame sequential type electronic scope 2A and frame sequential type television camera 8C may be emitted. By the way, in case the mosaic type electronic scope 2B, mosaic type television camera 8D and fiber scope 3E are connected to the light source apparatus 15, this filter cassette 38 may be pulled out so that a white color light adapted to the respective scopes may be emitted.

Within the above mentioned turret cassette 384, a disc-like filter plate 391 is provided so that a shaft 392 provided in the rotation center of this filter plate 391 may be borne.

A sector-like infrared ray cutting filter 393, neutral density filter (ND filter) 394 having a light reducing effect, special light observing filter 396 selecting the wavelength region of the illuminating light and aperture 397 are arranged in the peripheral direction on this filter plate 391.

The above mentioned infrared ray cutting filter 393 is to be used to remove the infrared component contained in the illuminating light in case the above mentioned filter cassette 38 is inserted and fitted. The special light observing filter 396 can transmit a wavelength band in which the light absorbance remarkably varies, for example, with the amount of hemoglobin and oxygen saturated degree in blood and is used in the case of making a special light observation. Further, the aperture 397 is to be used in case the filter cassette 388 is pulled out, that is, in case the color mosaic type electronic scope 2B, color mosaic type television camera 8D and fiber scope 2E are connected.

A plurality of pawls 398 are provided to project on the outer periphery of the above mentioned filter plate 391 so as to be able to contact a projection 402 inserted through a slit 401 provided in the bottom plate 399 of the turret cassette 384. As in FIG. 45, when this turret cassette 384 is inserted through an aperture 404 provided in the top plate 77 forming the housing 29, the above mentioned projection 40w will project into the turret cassette 384.

The above mentioned projection 402 is provided at the tip of a pin 408 projected and retracted by a solenoid 407 so that, when this pin 408 is projected, the projection 402 will press the pawl 398 in the tangential direction of the filter plate 391 to be able to rotate the filter plate 391.

In FIG. 46, the solenoid 407 is to be controlled by a turret controlling circuit 411. When a turret rotating switch not illustrated provided, for example, on the front surface plate is operated, the solenoid 407 will be operated by the turret controlling circuit 411. By the way, a light emitting diode 412 and photosensor 413 are provided near the turret cassette 384 so that the angle rotated by the solenoid 407 may be sensed, the sensed angle may be input in the turret controlling circuit 411 and a designated filter may be inserted in the light path.

By the way, the filter provided in the turret cassette 384 may be a filter attenuating the peak of a luminous line spectrum high in the interferability and contained in the emitted light of the light source lamp 31 or removing the luminous line spectrum.

According to this embodiment, when the filter provided in the turret cassette 34 is selectively inserted in the light path of the illuminating light, the wavelength region in which the illuminating light can be reduced and special observation can be made will be able to be transmitted. Further, when the turret cassette 384 is pulled out and a turret cassette provided with a filter which can transmit another wavelength region is inserted and fitted, rich information necessary for a diagnosis or the like will be able to be obtained.

FIG. 471 shows the 11th embodiment of the present invention.

Within the turret cassette 384, a disc-like filter plate 391 is provided so that a shaft 414 provided in the rotation center of this filter plate 391 may be borne. A gear 415 is provided on the outer peripheral surface of this filter plate and is meshed with a gear 416 inserted through a slit 401 provided in the bottom plate 399 of the turret cassette 384. This gear 416 is rotated by a motor 417 provided on the light source apparatus 15 side. This motor 417 is controlled in the rotation by a turret controlling circuit 411.

The other formations, operations and effects are the same as in the first embodiment.

By the way, in the above mentioned respective embodiments, the filter cassette and turret cassette are separately provided but may be made integrally insertable and removable.

Figure 48:
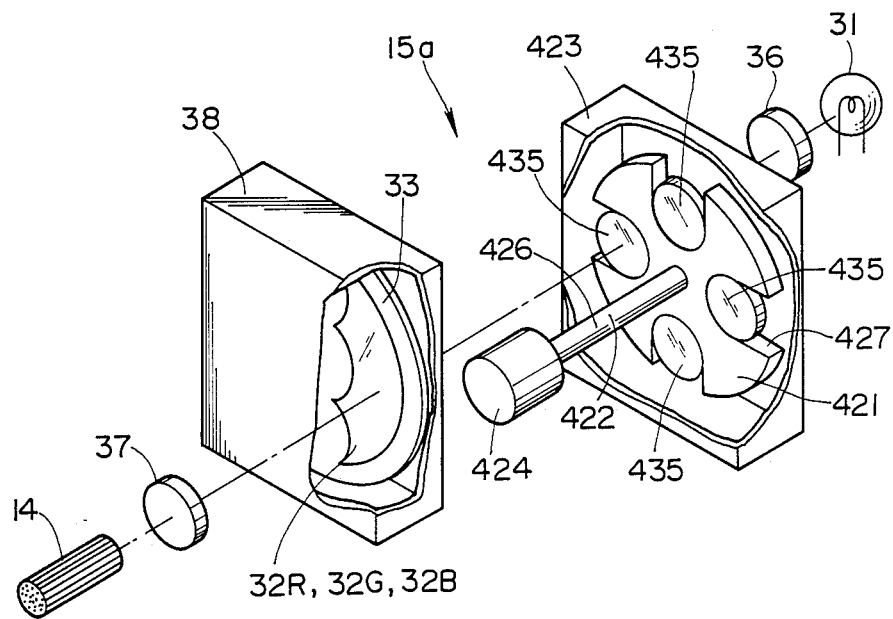

FIGS. 48 to 50 show the 12th embodiment of the present invention.

In this embodiment, the filter provided within the turret cassette of the 10th embodiment is removably fitted.

The turret plate 421 is disc-like and is provided with a rotary shaft 422 in the center. This rotary shaft 422 is rotatably borne by bearings not illustrated fixed to a housing 423 containing the turret plate 421. Further, the above mentioned rotary shaft 422 is connected at one end to a driving shaft 426 of a motor 424 so as to rotate the turret plate 421. A plurality of arcuate incisions 427 are provided at regular intervals on the peripheral edge of the turret plate 421. A fixing means, for example, a plate spring 428 is fitted at the base end to one surface of this turret plate 421. Further, this plate spring 428 is bent at the tip to form a V-shaped engaging pawl 429 opposed to the inner end of the above mentioned incision 427. A filter frame 430 is removably fitted to this incision 427 by the above mentioned plate spring 428. That is to say, the above mentioned filter frame 430 is formed to be annular and is provided on the outer peripheral surface with an engaging groove 431 engageable with the inner peripheral edge of the above mentioned incision 427. Further, on both side surfaces of the filter frame 430, annular grooves 432 are provided concentrically with the center axis 0 of the filter frame and are V-shaped in the cross-section so as to engage with the engaging pawls 429 of the plate springs 428 when the filter frame 430 is inserted into the above mentioned incision 427. A filter fitting step 433 and female screw 434 are provided on the inner peripheral surface of the filter frame 430. A filter 435 is fitted to the filter fitting step 433 and is fixed by a fastening ring 436 screwed to the above mentioned female screw 434.

In replacing the filter 435, when the filter frame 430 is pulled in the direction indicated by the arrow X in FIG. 49, the plate spring 428 engaged with the groove 432 of the filter frame 430 will be resiliently deformed, the engaging pawl 429 will be removed from the groove 432 and the filter frame 430 will be able to be removed from the turret plate 421. In the case of fitting the filter frame 4301 to the turret plate 421, when the engaging groove 431 of the filter frame 430 is opposed to the inner peripheral edge of the incision 427 and is pushed in the direction indicated by the arrow Y in FIG. 49, it will be inserted as engaged with the inner peripheral edge of the incision. When it is inserted to a predetermined position, the engaging pawl 429 of the plate spring 428 will drop into the groove 432 and will be engaged and fixed. Therefore, when a filter frame 430 fitted with a filter 435 to be used is prepared in advance, various filters 435 will be able to be selectively fitted to the turret plate 421 by the filter frame 430 and will be able to be easily replaced. As the filter frame 430 is provided with the grooves 432 on both side surfaces, even if the front and back are reversed to each other at the time of inserting the filter frame 430 into the turret plate 421, the filter frame will be able to be fitted. Also, as the grooves 432 are made annular concentrically with the center axis 0 of the filter frame 430, even if the filter frame 430 is inserted in any direction in the incision 427, it will be able to be engaged with the engaging pawls 429 of the plate springs 428.

By the way, in the above mentioned embodiment, the filter frame is provided with grooves on both side surfaces but may be provided with a groove on one side surface. The fixing means is not limited to be a plate spring but may be an engaging member resiliently removably engageable with the groove and is not limited in the structure.

As mentioned above, in this embodiment, as the filter frame fitted with the filter is provided with a groove concentrically with the center axis on at least one side surface and the turret plate is provided with a fixing means removably engaging with this groove, there are effects that the filter can be removably fitted by one touch and that, even if a vibration or shock is applied, the filter frame will not drop and will be able to be positively fitted. Further, as the above mentioned groove is provided on the entire periphery of the filter frame, the inserting direction will not be limited and the filter can be easily replaced.

Figure 51:
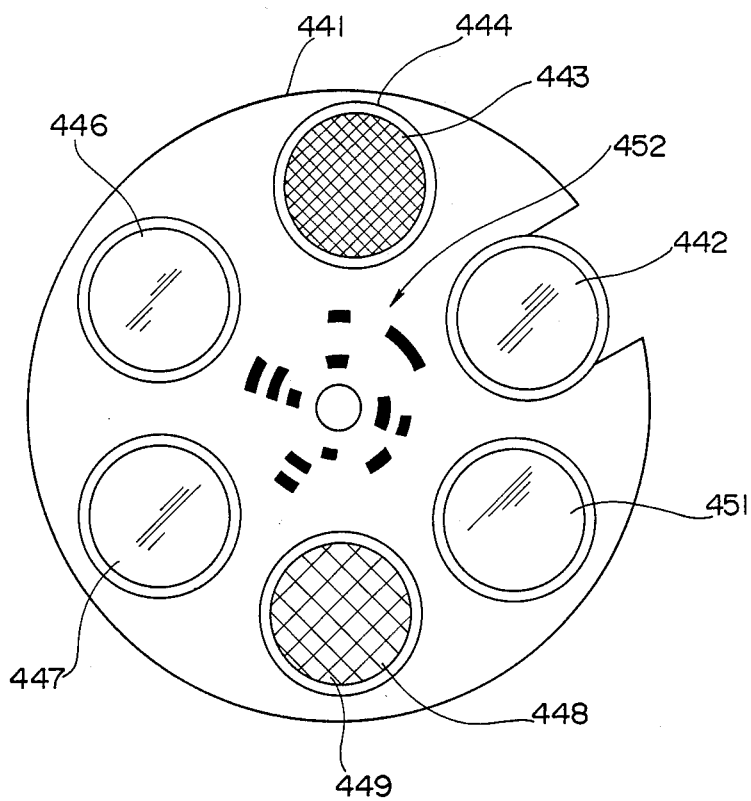
FIGS. 51 to 53 relate to the 13th embodiment of the present invention.
Figure 52:
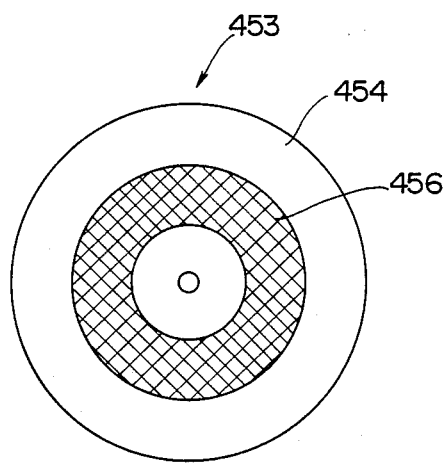
Figure 53:
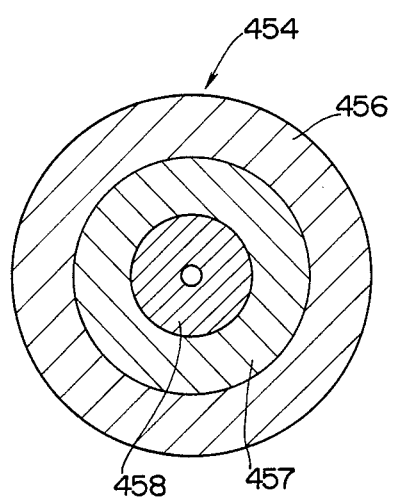

FIGS. 51 to 53 show the 13th embodiment of the present invention.

In this embodiment, not only the removably fittable filter described in the 12th embodiment but also a mesh-like filter as a light reducing filter is provided.

In FIG. 51, a filter plate 441 provided rotatably within a turret cassette not illustrated is formed to be disc-like. In the peripheral direction of this filter plate 441, by the same formation as in the 12th embodiment, a through glass 442 not limiting the wavelength region of the transmitted light is provided and a first light amount adjusting filter 444 formed of a net 443, for example, of ¼ mesh, a neutral density filter (ND filter) 446 having a light reducing effect, an infrared ray cutting filter 447, a second light amount adjusting filter 449 formed of a net 448, for example, of ½ mesh and a through glass 451 not limiting the wavelength region of the transmitted light are fixed.

On the inside diameter side of the above mentioned filters 442, 444, 446, 447, 449 and 451, further a plurality of position detecting marks 452 are concentrically provided so that, when these position detecting marks 452 are read out by a position detecting sensor not illustrated, the filter interposed in the light path of the illuminating light will be able to be detected.

Also, as in FIG. 52, a filter plate 453 is formed by concentrically arranging a through glass 454 not limiting the wavelength region of the transmitted light and a net 456, for example, of ½ mesh and may be moved in the direction vertically intersecting the light path of the illuminating light and coinciding with the rotation center of the filter plate 453, that is, in the diametral direction of the filter plate 453 to adjust the light amount of the illuminating light.

Further, as in FIG. 53, a plurality of films 456, 457 and 458 different in the transmittivity are concentrically formed on the surface of a filter plate 454 which may be moved in the diametral direction. By the way, a plurality of films different in the transmittivity are radially provided on a filter plate which may be rotated with the rotation center line as a center. Further, the filter provided within the filter cassette used together with the turret cassette may be a disc-like signal wavelength filter.

Figure 54:
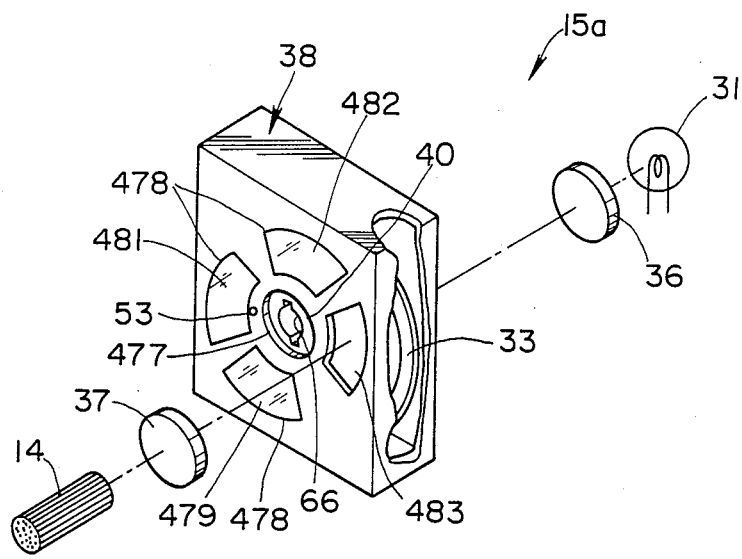
FIGS. 54 to 56 relate to the 14th embodiment of the present invention.
Figure 55:
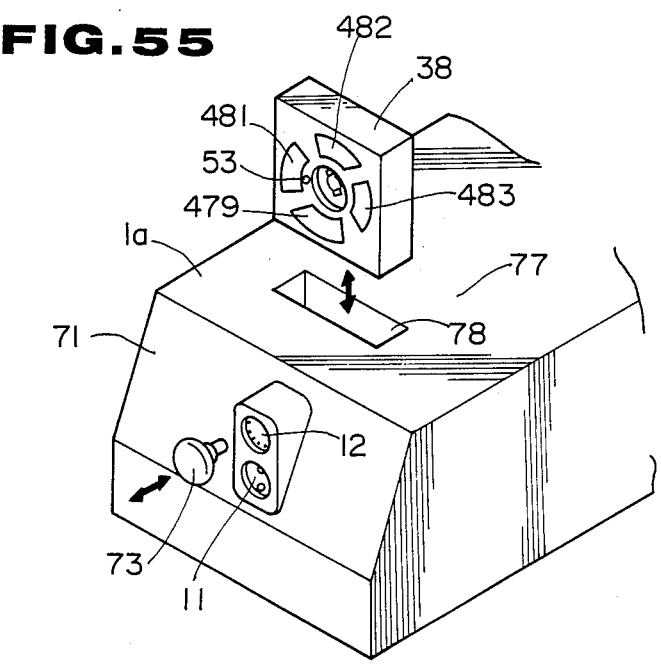
Figure 56:
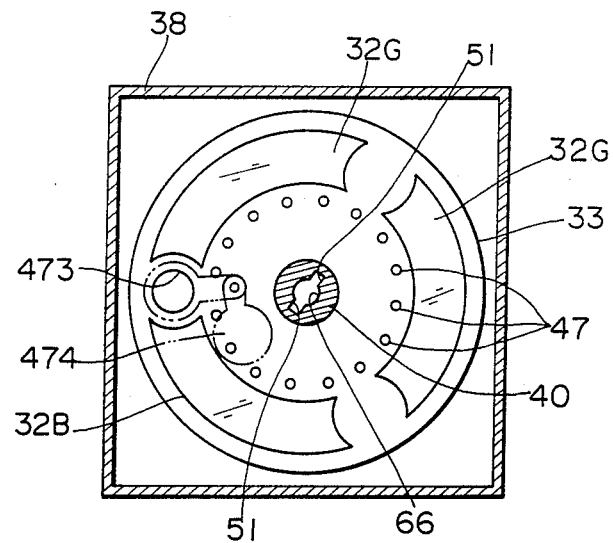
Figure 57:
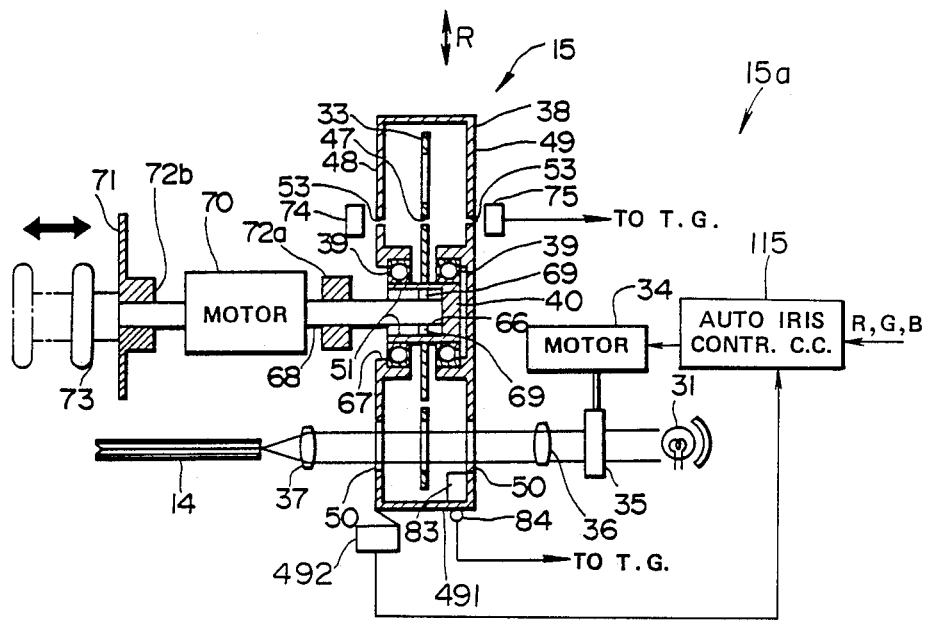
FIGS. 57 to 63 relate to the 15th embodiment.
Figure 58:
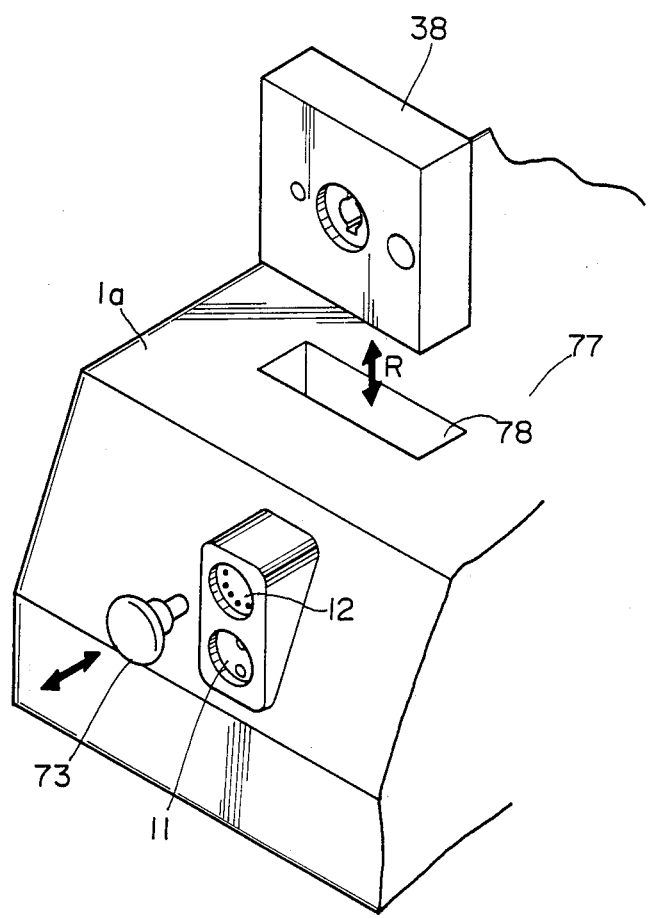
Figure 59:
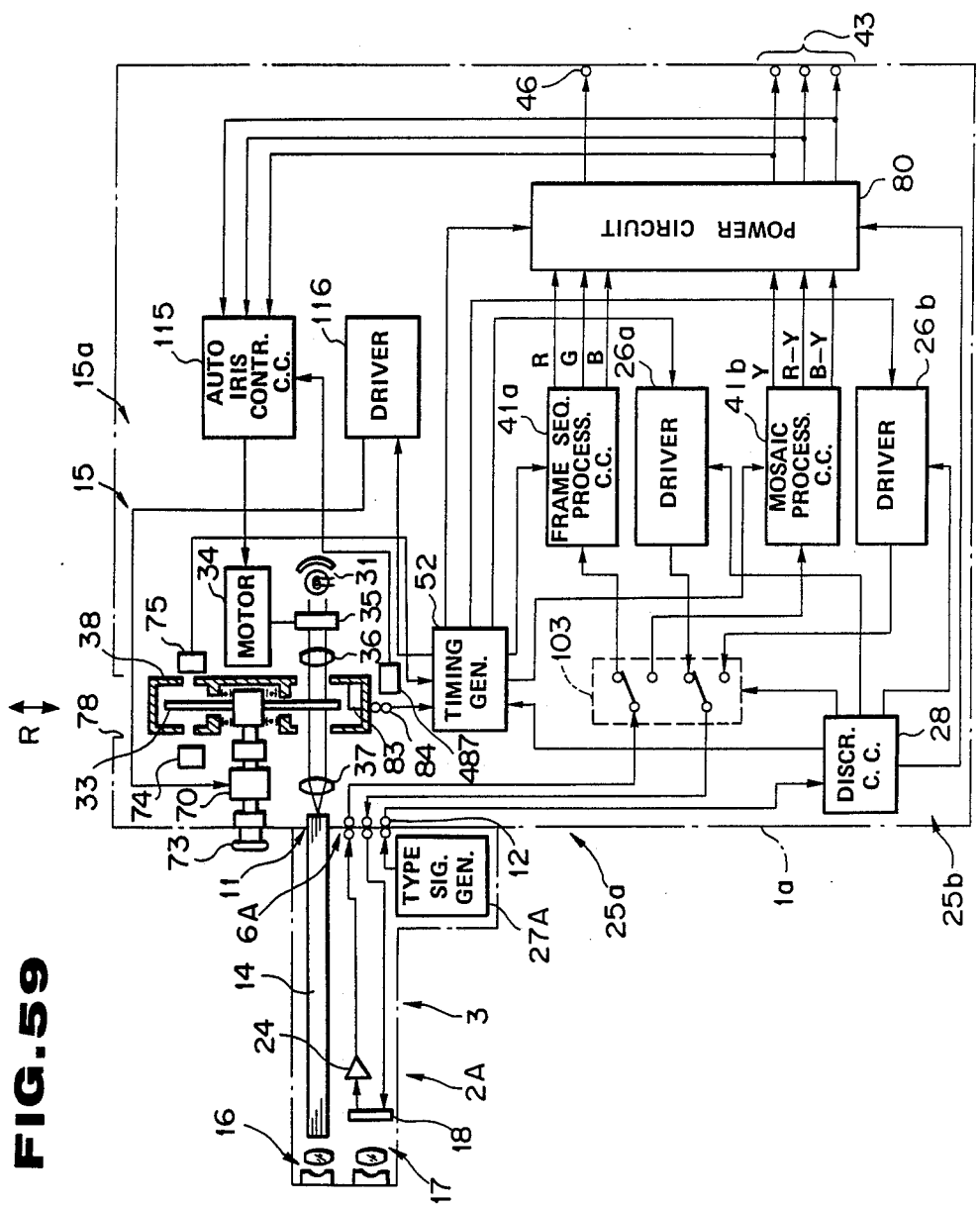

FIGS. 54 to 56 show the 14th embodiment of the present invention.

As shown in FIG. 54, in a light source part 15a of a light source apparatus 15 in this embodiment, there are arranged a light source lamp 31 emitting a white color light, a parallel light lens 36 positioned on the light path connecting this light source lamp 31 with the entrance end surface of a light guide 14 which the illuminating light enters and making the above mentioned illuminating light a parallel light, a removably insertable filter cassette 38 provided with a rotary filter 33 acting as a color separating means color-separating the illuminating light made the above mentioned parallel light when the frame sequential type electronic scope 2A or the frame sequential type television camera 8C is connected to the light source apparatus 15 and as a main filter member transmitting a white color light when the color mosaic type electronic scope 2B or the color mosaic type television camera 2D is connected and an auxiliary filter member having a wavelength selecting means which can transmit a part of the wavelength region of the illuminating light and a condenser lens 37 condensing the illuminating light having passed through this filter cassette 38.

As shown in FIG. 55, the above mentioned filter cassette 38 is formed to be removably insertable in the light path of the light source apparatus 15 which is the fitting part through an inserting part 78 provided, for example, on the top plate 77 of the control apparatus 1a.

The same as in FIGS. 7 and 8 in the first embodiment, as shown in FIG. 56, the filter cassette 38 is internally provided with the rotary filter 33 which is disc-like, has filters 32R, 32G and 32B transmitting three primary colors of red (R), green (G) and blue (B) in the peripheral direction on the disc surface, makes the white color light emitted from the light source lamp 31 illuminating lights of the respective wavelengths of red, green and blue and can emit an illuminating light adapted to the frame sequential type electronic scope 2A and frame sequential type television camera 8C. The above mentioned rotary filter 33 has a white color light transmitting window 473 transmitting a white color light as it is on the frame surface between the filters 32B and 32G transmitting, for example, blue (B) and green (G). A light interceptor 474 which is also a fly weight and rotates with the fulcrum as a center is borne adjacently to this transmitting window 473 and will rotate as indicated by the imaginary line in FIG. 56 with the fulcrum as a center under the centrifugal force when the rotary filter 33 is rotating, that is, when the illuminating light for the frame sequential type electronic scope 2A or frame sequential type television camera 8C is emitted. Under the centrifugal force, the light interceptor 474 which is also a fly weight will rotate as shown by the imaginary line in FIG. 56 with the fulcrum as a center and will close the transmitting window 473 so that the white color light may not obstruct transmitting the color lights of the respective wavelengths of red, green and blue in time series. On the other hand, when the illuminating light for the color mosaic type electronic scope 2B, color mosaic type television camera 2D or fiber scope 2E is emitted, the rotary filter 33 will stop and the transmitting window 473 will be positioned in the light path and, when the rotary filter 33 stops, the light interceptor 474 which is also a fly weight will be perpendicularly hung as shown by the solid line in FIG.

56 to open the transmitting window 473 to pass the white light.

In the example illustrated in FIG. 54, the filter cassette 38 is formed to be square on the front surface and sector-like transmitting windows 478 to be provided respectively with wavelength selecting means are provided on the surface from the boss 477 of the front surface to the respective four sides. When the filter cassette 38 is inserted through the inserting part 78, if the inserting direction of the respective sides in sequentially changed, the respective transmitting windows 478 will be sequentially positioned in the light path of the light source lamp 31. For example, an infrared ray cutting filter 479 is arranged in one of the above mentioned transmitting windows 478, a neutral density filter (ND filter) 481 having a light reducing effect is arranged in another of the transmitting windows 478, further a special light observing filter 481 transmitting a part of the wavelength region of the illuminating light is arranged in another of them and further an aperture 483 without a filter is made in another of them.

The above mentioned infrared ray cutting filter 479 is used to remove the infrared component contained in the illuminating light. The special light observing filter 482 can transmit the wavelength band wherein the light absorbance remarkably varies, for example, with the amount of hemoglobin and oxygen saturated degree in blood and is used in the case of making a special light observation. Further, the aperture 483 will be used when the rotary filter 464 is stopped and the transmitting window 473 is positioned in the light path, that is, in case the color mosaic type electronic scope 2B, color mosaic type television camera 8D or fiber scope 2E is connected.

By the way, on the back surface plate 484 of the filter cassette 466, transmitting windows of the same shapes and sizes are provided in the same positions as of the respective transmitting windows of the above mentioned front surface plate 476. By the way, in the illustrated embodiment, the filter cassette is square, four transmitting windows are formed and four kinds of wavelength limiting means are provided. However, the filter cassette can be made right pentagonal or hexagonal to increase the transmitting windows and wavelength limiting means.

By the way, the filter provided in the transmitting window 478 of the filter cassette 466 may be a filter attenuating the peak of the luminous line spectrum high in the interferability and contained in the emitted light of the light source lamp 461 and removing the luminous line spectrum.

According to this embodiment, when the filter provided in the transmitting window of the filter cassette 446 is selectively inserted in the light path of the illuminating light by changing the inserting direction of the filter cassette 466, the infrared component will be able to be removed, the illuminating light will be able to be reduced and the wavelength region wherein a special observation can be made will be able to be transmitted.

In this embodiment, if the above described filter cassette in which the rotary filter is omitted is separately prepared, the white color light transmitting window and light interceptor will be able to be omitted from the rotary filter of the illustrated example. That is to say, when the illuminating light corresponding to the color mosaic type electronic scope, externally fitted camera and fiber scope is to be obtained, a filter cassette not internally provided with this rotary filter may be inserted into the light source apparatus and, by changing the inserting direction of this filter cassette, illuminating lights adapted to various special light observations can be selectively obtained.

By the way, a filter cassette in which the white color light transmitting window and light interceptor are omitted from the illustrated rotary filter may be formed. In this case, in order to obtain the illuminating light adapted to the color mosaic type electronic scope, externally fitted camera or fiber scope, the filter cassette may be pulled out of the light source apparatus. By the way, the light interceptor operating means for intercepting the light through the white color light transmitting window is not limited to the fly weight of the illustrated example but, fro example, a spring, solenoid or the like may be used.

FIGS. 57 to 63 show the 15th embodiment of the present invention.

In this embodiment, the light source part described in the first embodiment is provided with a switch to be switched on and off by inserting and removing the filter cassette so that the automatic light adjusting circuit may be directly controlled by these on and off-signals.

The filter cassette 38 is of the same formation as is described in the first embodiment. When the filter cassette 38 is inserted through an aperture 78 provided, for example, on the top plate 77 of the control apparatus 1a as in FIG. 58 and is positioned and then a removably fitting knob 73 is pushed toward the controlling apparatus 1a, a driving shaft 68 of rotary filter driving motor 70 will be inserted into a den 66 provided in a rotary shaft 40 supporting a rotary filter 33 and will be connected so as to be able to transmit the rotation.

Further, simultaneously with this positioning, the bottom plate 48b of the filter cassette 38 will switch on a switch 487 and the on-signal of this switch 487 will be input into an automatic light adjusting circuit 115. When the on-signal is input, this automatic light adjusting circuit 115 will operate the diaphragm motor 34 to open a diaphragm 35 and increase the light amount of the illuminating light entering the color transmitting filters 32R, 32G and 32B.

In case the above mentioned filter cassette 38 is pulled out, the switch 487 will be off and the automatic light adjusting circuit 115 will operate the diaphragm 35 by the diaphragm motor 34 to squeeze the illuminating light entering the light guide entrance end surface.

Figure 60:
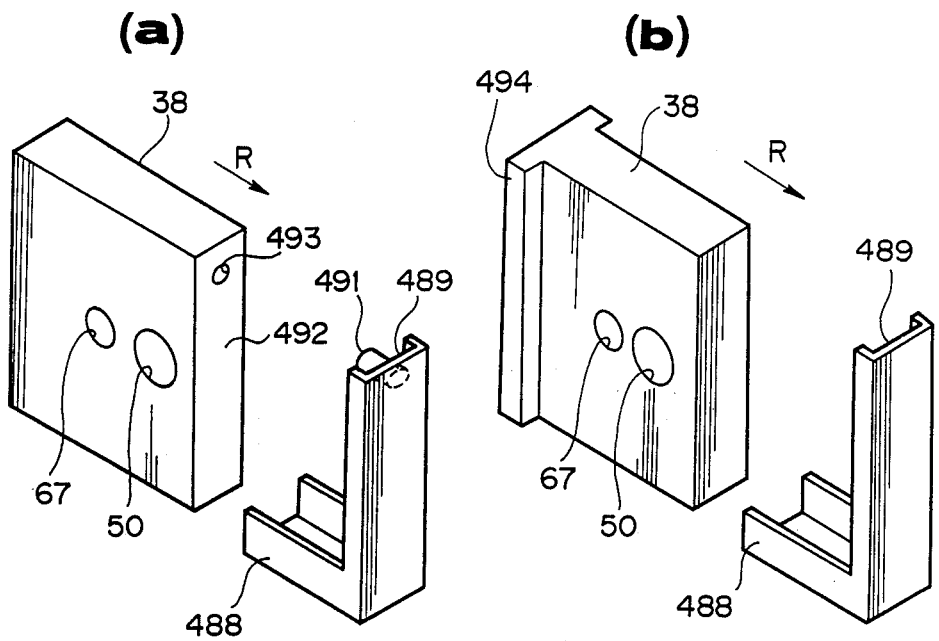

By the way, as shown in FIG. 60, the mis-insertion of the filter cassette 38 may be prevented.

In FIG. 60 (a), the filter cassette 38 is provided with a recess 489 in which a cassette holding member 488 can be inserted. A pin 491 which can be fitted in a hole 493 provided on the side plate 492 of the filter cassette 38 is provided to project in this recess 489. In FIG. 60 (b), the filter cassette 38 projects on one edge 494 in the thickness direction. If the inserting direction is wrong, this edge 494 will contact the cassette holding member 488 and the filter cassette 38 will not be able to be inserted.

Figure 61:
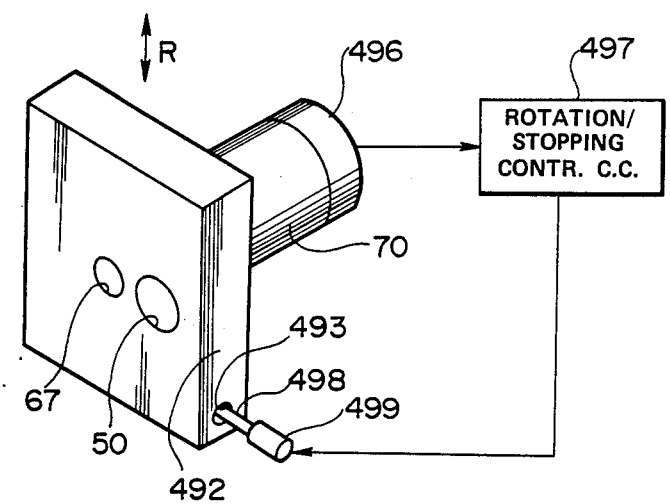

As in FIG. 61, in case the rotary filter 33 is rotating, the filter cassette 38 may be made unable to be pulled out.

A frequency generator 496 which will be able to generate such signals as, for example, pulse waves only in case a rotary filter motor 70 is being driven is provided at the rear end of the rotary filter motor 70 driving the rotary filter 33. The signal of this frequency generator 496 is input into a rotation/stop sensing circuit 497 which is to operate a solenoid 499 having a pin 498 inserted in a hole 493 of the side plate 492 of the filter cassette 38. When the pulse waves are input, this rotation/stop sensing circuit will project the pin 498 to prevent the filter cassette 38 from being pulled out by mistake. When the rotation of the rotary filter 33 stops and pulse waves are no longer input, the pin 498 will be retreated and the filter cassette 38 will be able to be pulled out.

Figure 62:
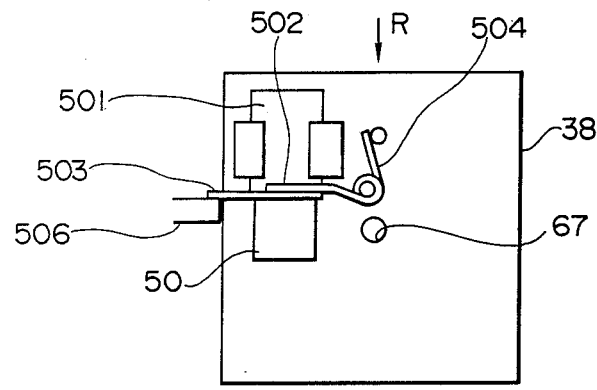
Figure 63:
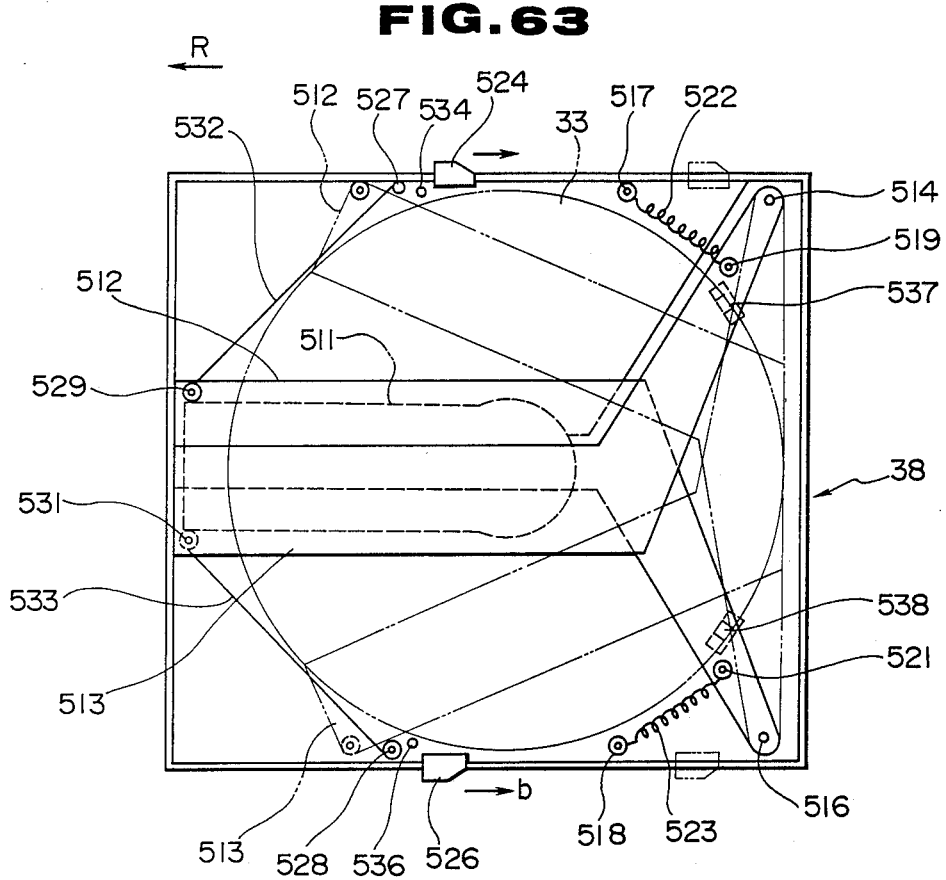

Further, as in FIGS. 62 and 63, the window 50 of the filter cassette 38 may be provided with a lid so that no dust may come in through the window 50.

In FIG. 62, the window 50 through which the illuminating light of the cassette filter 38 passes is provided with a lid 501 which can slide vertically. A flange 502 is provided in the lower part of this lid 501 and forms at the end a pawl 503 projecting sidewise of the filter cassette 38. A spring 504 supported at one end by the filter cassette 38 is engaged at the other end with this flange 502 so as to be energized when the lid 501 is opened. When the filter cassette 38 is inserted in the direction indicated by the arrow R, the above mentioned pawl 503 will contact a projection 506 provided on the light source apparatus 15 to energize the spring to open the lid 501. When the cassette filter 38 is pulled out, the lid 501 will be closed by the spring 504 prevent dust from coming in.

In FIG. 63, an aperture 511 in which the driving shaft 68 inserting part and illuminating light window are made integral is formed in the filter cassette 38. Two shutter blades 512 and 513 closing this aperture 511 are pivoted respectively to shafts 514 and 516 fixed to the filter cassette 38 and are energized by tension springs 522 and 523 respectively between cassette side fixing pins 517 and 518 and shutter blade side fixing pins 519 and 521 so as to rotate relatively with each other and close the aperture 511. The filter cassette 38 is provided on the side plate with hooks 524 and 526 sliding along the side edges so that, in case the filter cassette 38 is inserted in the direction indicated by the arrow R, the hooks 524 and 526 will engage with projections not illustrated on the light source apparatus side, will slide in the direction indicated by the arrow b and the shutter blades 512 and 513 will be opened by wires 532 and 533 fixed to swing stoppers 529 and 531 of the shutter blades 512 and 513 through guide rollers 527 and 528 from the hooks 524 and 526, respectively.

In the above mentioned embodiment, the insertion and removal of the filter cassette 38 are sensed by the on-off switch 487. However, the sensing means is not limited to this embodiment but such other sensing means as, for example, a light emitting diode and phototransistor may be used. A signal generated by a filter kind recording part 83 may be input into the automatic light adjusting circuit 115 to operate the diaphragm 35.

Further, as a means of controlling the light amount, the illuminating light entering the entrance end surface of the light guide may be defocused by moving the condenser lens 37.

Further, the color transmitting filters 32R, 32G, and 32B may be filters for such special observation as an infrared observation.

The light amount emitted by the light source lamp 31 may be reduced.

In this embodiment, by providing a switch 487 which can sense the insertion and removable of the filter cassette 38, the automatic light adjusting circuit 115 can be operated not only through the three primary color signals but also directly. Therefore, even in case the filter cassette 38 is pulled out, the illuminating light entering the entrance end surface of the light guide will be able to be quickly squeezed. The entrance end surface of the light guide will be able to be positively prevented from being burned.

Figure 64:
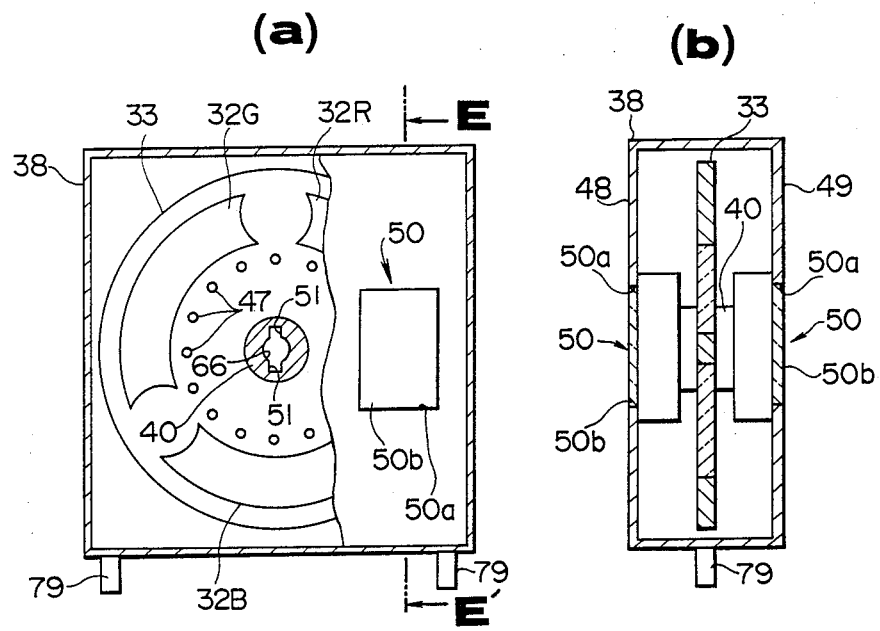
FIGS. 64 and 65 relate to the 16th embodiment.
Figure 65:
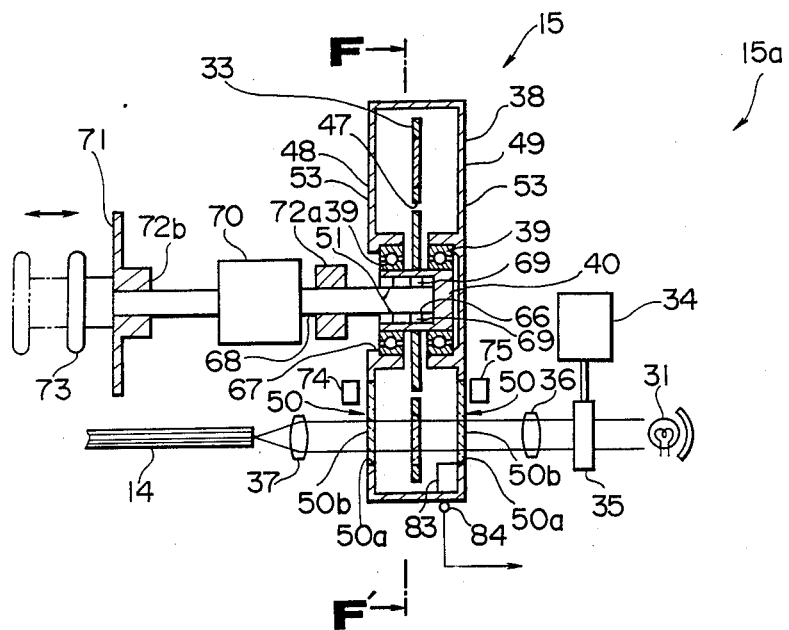

FIGS. 64 and 65 show the 16th embodiment of the present invention.

On the front surface plate 48 and back surface plate 49 of the filter cassette 38, in a position positioned in the light path of the light source lamp 31 when fitted to the light source apparatus 15, a transmitting window 50a is opened and is fitted with a glass 50b as a transparent member to form a closed transparent window 50 so that no dust may enter the filter cassette 38 and the color light having passed through the internally fitted rotary filter 33 may not be influenced. The transparent window 50 closed with the glass 50b is formed to be comparatively larger in the area and is opposed t the above described timing detecting hole 47. Further, for example, a light emitting device 74 is arranged so as to see the above mentioned timing detecting hole 47 from one transparent window 50. For example, a photosensor 75 is provided so as to see the above mentioned timing detecting hole 47 from the other transparent window 50.

By the way, the color transmitting filter may be a filter for such special observation as an infrared observation. Also, in the case of using a scope provided with a color mosaic type imaging means and a fiber scope as connected to the light source apparatus, it will not be necessary to insert a rotary filter and the white color light entering the entrance end surface of the light guide may be defocused by the condenser lens.

The transparent member of the transparent windows 50 provided on the front surface and back surface plates of the filter cassette 38 may be formed of a plastic or infrared cutting filter.

Further, all the side surface plates of the filter cassette 38 may be formed of a transparent member.

In this embodiment, the rotary filter is borne by ball bearings fitted in the central part of the filter cassette but the ball bearings may not be fixed and such resilient members as, for example, springs may be fixed to the outer races of the respective ball bearings to support the rotary filter. By thus supporting the rotary filter with the resilient members, even in case any difference is produced between the axes of the rotary filter driving motor and rotary filter, the difference will be able to be absorbed by the resilient members.

Figure 66:
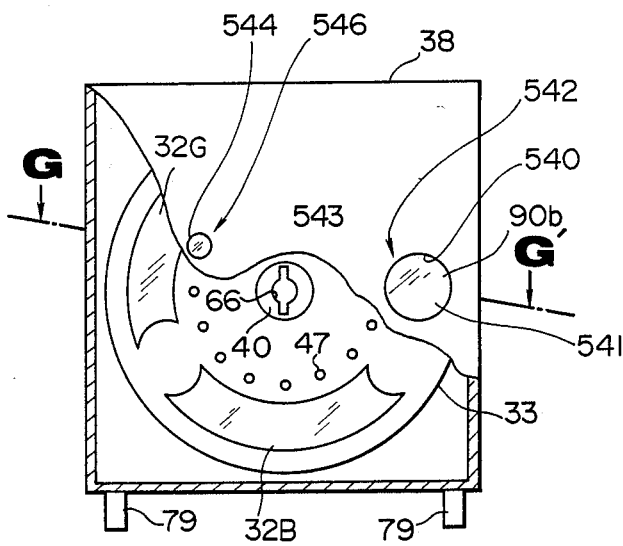
FIGS. 66 and 67 relate to the 17th embodiment of the present invention.
Figure 67:
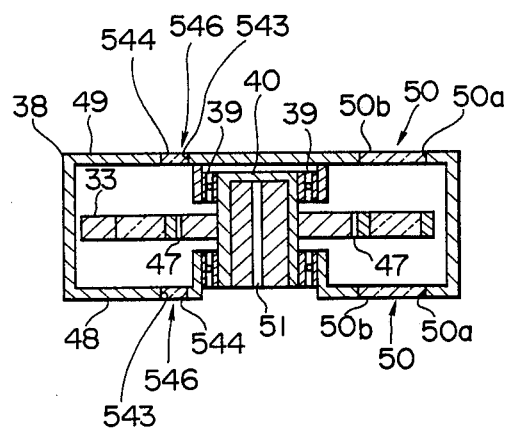

FIGS. 66 and 67 are sectioned views showing the formation of a filter cassette.

In this embodiment, a transmitting window through which a white color light is to pass and a transparent window for detecting a timing a-e provided as separated from each other.

On the front surface plate 48 and back surface plate 49 of the filter cassette 38, in a position positioned in the light path of the light source lamp 31 when fitted to the light source apparatus 15, a transmitting window 540 is opened and is fitted with a glass 541 as a transparent member to form a closed transparent window 50 so that no dust may enter the filter cassette 38 and the color light having passed through the internally fitted rotary filter 33 may not be influenced. Also, in the same manner, on the front surface plate 48 and back surface plate 49, a timing detecting transmitting window 543 is opened as faced to the timing detecting holes 47 and is fitted with a glass 544 as a transparent member to form a closed transparent window 54b so that no dust may enter the filter cassette 38. Further, for example, a light emitting device 74 is arranged so that the above mentioned timing detecting hole 47 may be seen from one timing detecting transparent window 54b and, for example, a photosensor 75 is provided so that the above mentioned timing detecting hole 47 may be seen from the other timing detecting transparent window 54b.

The other formations, operations and effects are the same as in the first embodiment.

FIGS. 68 to 72 show the 18th embodiment of the present invention.

Figure 69:
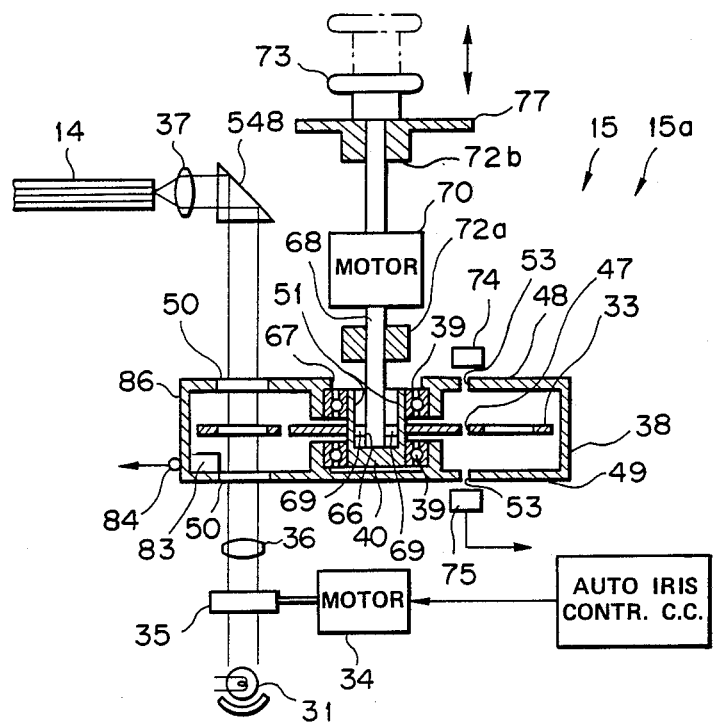
Figure 70:
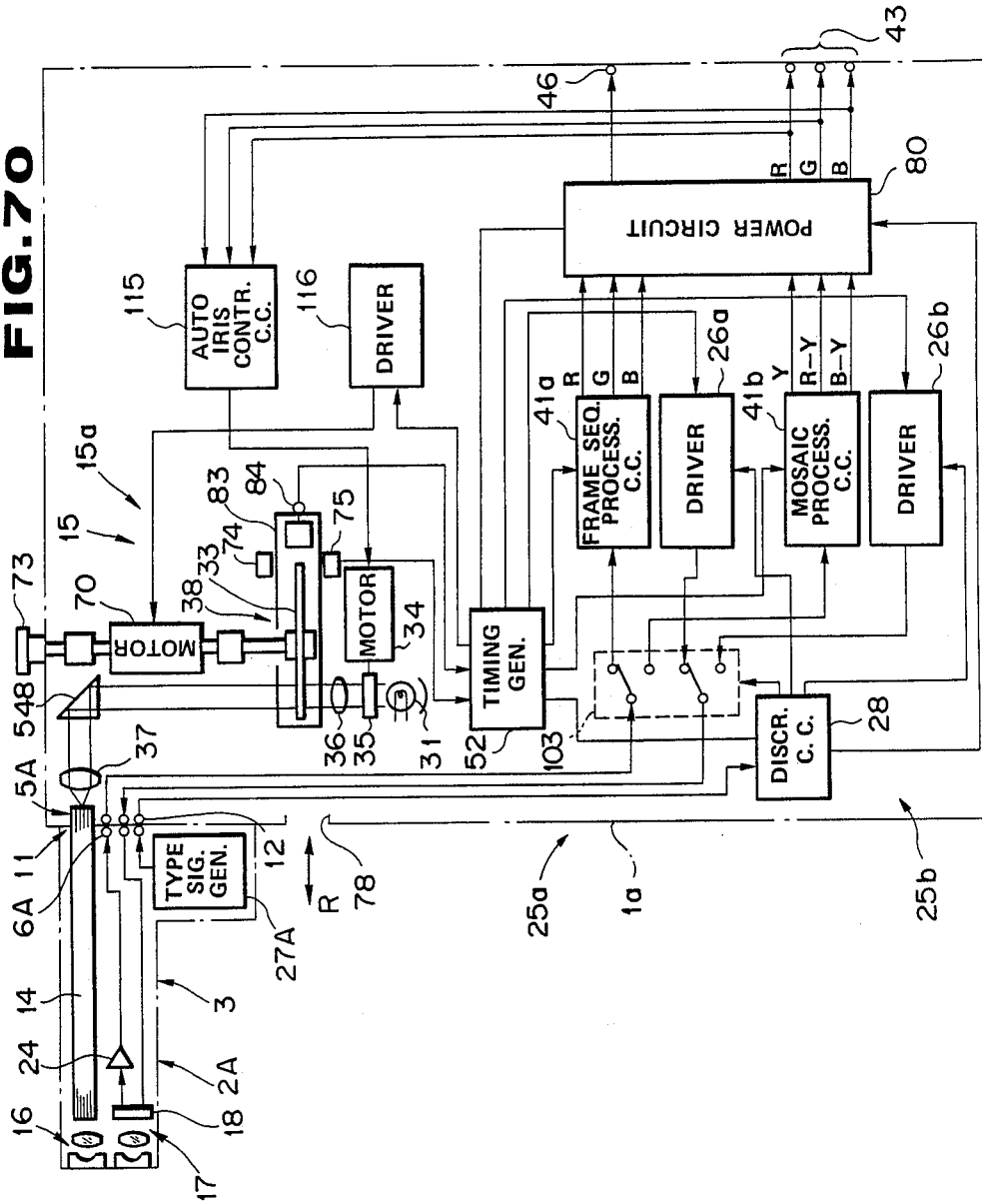

In a light source part 15a of a light source apparatus 15 of this embodiment, as shown in FIG. 69, the illuminating light of a light source lamp 31 emitting a white color light upward will have the light path bent at right angles by a prism 548 and will enter the entrance end surface of the light guide 14. In the light path connecting this light source lamp 31 with the prism 548, there are provided a light amount adjusting diaphragm 35 driven by a diaphragm motor 34, a filter cassette 38 provided with a rotary filter 33 and inserted and fitted in case the frame sequential type electronic scope 2A or a frame sequential type television camera 8C is connected to the light source apparatus 15 and a parallel light lens 36 for making the white color light entering this rotary filter a parallel light. Further, a condenser lens 37 condensing the illuminating light having passed through the rotary filter 33 and emitted from the prism 548 is arranged between the prism 548 and the entrance end surface of the light guide 14.

The above mentioned rotary filter 33 is formed to be disc-like and is provided with the rotation center in the vertical direction. This rotary filter 33 has in the peripheral direction on the surface color transmitting filters 32R, 32G and 32B for three primary colors of red (R), green (G) and blue (B) so that the white color light emitted from the light source lamp 31 may be made illuminating lights of the respective wavelengths of red, green and blue and an illuminating adapted to the frame sequential type electronic scope 2A and frame sequential type television camera 8C may be emitted. By the way, in case the mosaic type electronic scope 2B, mosaic type television camera 8D or fiber scope 2E is connected, this filter cassette 38 will be pulled out and a white color light may be emitted.

A plurality of holes 47 for detecting the timing of reading out solid state imaging device signals are provided in the peripheral direction on the inside diameter side of these color transmitting filters 32R, 32G and 32B.

The above mentioned rotary filter 33 is contained in the filter cassette 38. A rotary shaft 40 borne by ball bearings 39 and provided in the central part of the filter cassette 38 is provided in the rotation center of the above mentioned rotary filter 33.

Windows 50 are provided on the front surface plate 48 and back surface plate 49 of the above mentioned filter cassette 38 so that the white color light emitted form the light source lamp 31 may pass through the color transmitting filters 32R, 32G and 32B. Further, windows 53 are provided on the front surface plate 48 and back surface plate 49 so as to see the above mentioned timing detecting holes 47. For example, a light emitting device 74 is arranged so as to see the holes 47 from one window 53. For example, a photosensor 75 is provided so as to see the holes 47 from the other window 52.

A den 66 having grooves 51 provided in the axial direction is provided on the front surface side end surface of the above mentioned rotary shaft 40. A window 67 is provided in the central part of the front surface plate 48 so as to see the above mentioned den 66.

In the above mentioned den 66, pins 69 projected in the diametral direction are provided so as to coincide with the above mentioned grooves 51 and a driving shaft 68 of a rotary filter driving motor 70 borne by a sliding bearing 72a with the rotation center in the vertical direction is inserted.

Above the above mentioned rotary filter driving motor 70, a substantially cylindrical removably fitting knob borne by a sliding bearing 72b is provided through, for example, the top plate 77 of the control apparatus 1a.

Within the above mentioned filter cassette 38, a filter kind recording part 83 for discriminating the kind of the filter wherein such information as of the spectral intensity and blanking period of the illuminating light passing through the rotary filter 33 is memorized, for example, by a ROM (read only memory) or combination of contacts is provided and is connected to a contact 84 provided on the side surface of the filter cassette 38.

Figure 68:
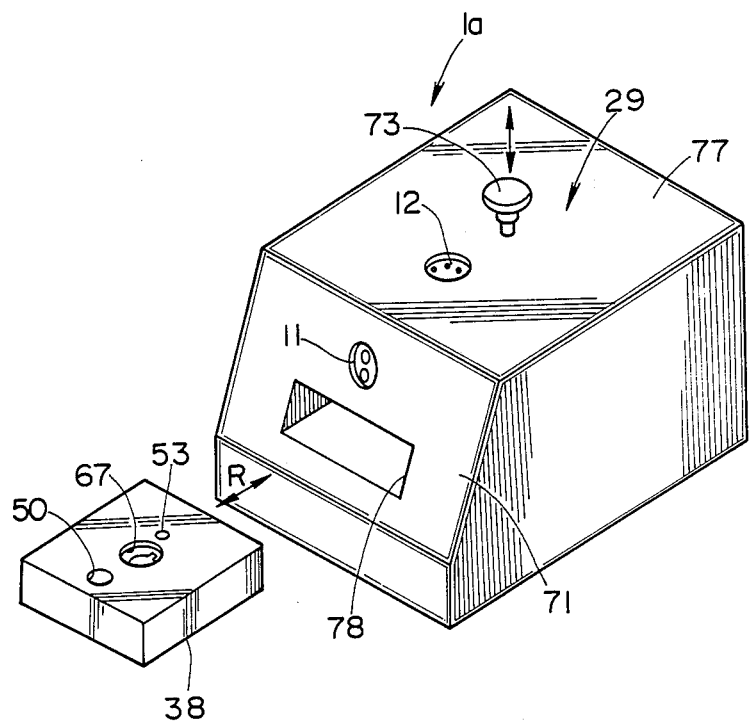
FIGS. 68 to 72 relate to the 18th embodiment.

As shown in FIG. 68, the above mentioned filter cassette 38 is inserted horizontally through an aperture 78 provided, for example, on the front surface plate 71 of the control apparatus 1a and is positioned by positioning pins 79. After the filter cassette 38 is positioned, when the removably fitting knob 73 is pushed toward the control apparatus 1a, the driving shaft 68 of the rotary filter driving motor 70 will be inserted into the den 66 provided in the rotary shaft 40 supporting the rotary filter 33 and will be connected so as to be able to transmit the rotation.

By the way, simultaneously with the positioning of the filter cassette 38, the contact 84 of the filter kind recording part 83 will be connected to a timing generator 52 within the control apparatus 1a, the kind and characteristic of the inserted rotary filter 33 will be transmitted to the timing generator 52 and signals adapted to them will be able to be output to the frame sequential type process circuit 41a, mosaic type process circuit 41b, drivers 26a and 26b, output circuit 80 and driver 116.

The above mentioned driver 116 will drive the rotary filter driving motor 70 with a synchronous signal adapted to the rotary filter 33 from the timing generator 52.

By the way, the above mentioned photosensor 75 will synchronize the timing of the clock of the timing generator 52 with the rotation of the rotary filter 33 and the output of this timing generator 52 will control the timing of the field sequential type process circuit 41.

Figure 71:
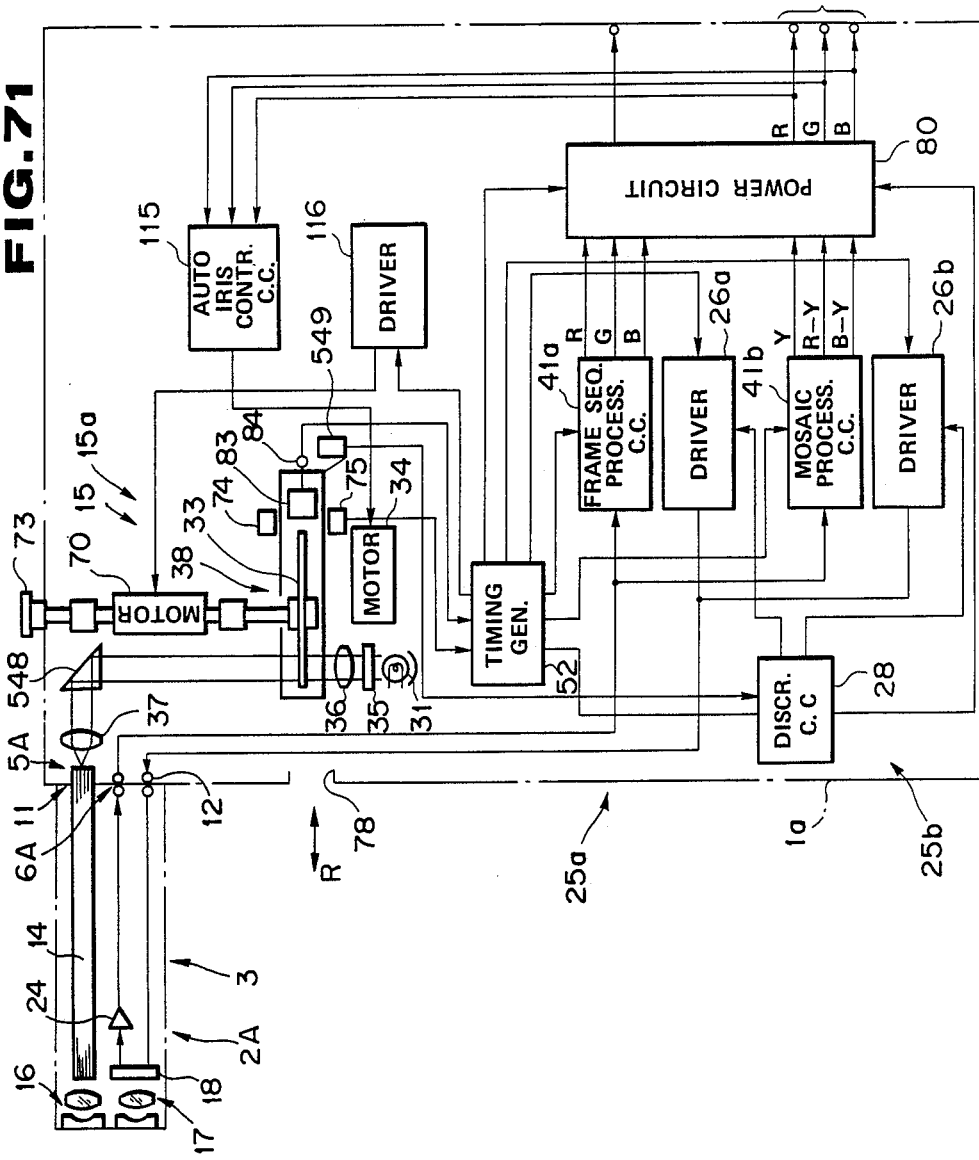

By the way, in this embodiment, in case the frame sequential type and mosaic type respective electronic scopes 2A and 2B and frame sequential type and mosaic type externally fitted television cameras 8C and 8D are connected, by the signals generated by the type signal generating circuits 27 respectively of them, the discriminating circuit 28 will discriminate the imaging systems of the connected scopes and television cameras and will switch the switching switch 103 to select the process circuit 41 and driver 26. As shown in FIG. 71, without providing the scope 2 and externally fitted television camera 8 with the type signal generating circuit 27, by inserting the filter cassette 38, the output circuit 80 may be controlled to output three primary color signals RGB converted by the frame sequential type process circuit 41a and a compound video signal of an NTSC system.

In FIG. 71, when the filter cassette 38 is inserted through the front surface plate 71 of the control apparatus 1a, the switch 549 will be on. This electric signal will be input into the discriminating circuit 28 which will switch switching switches 81 and 82 provided in the output circuit 80 so that three primary color signals RGB converted by the frame sequential type process circuit 41a and a composite may be output video signal of an NTSC system.

Figure 72:
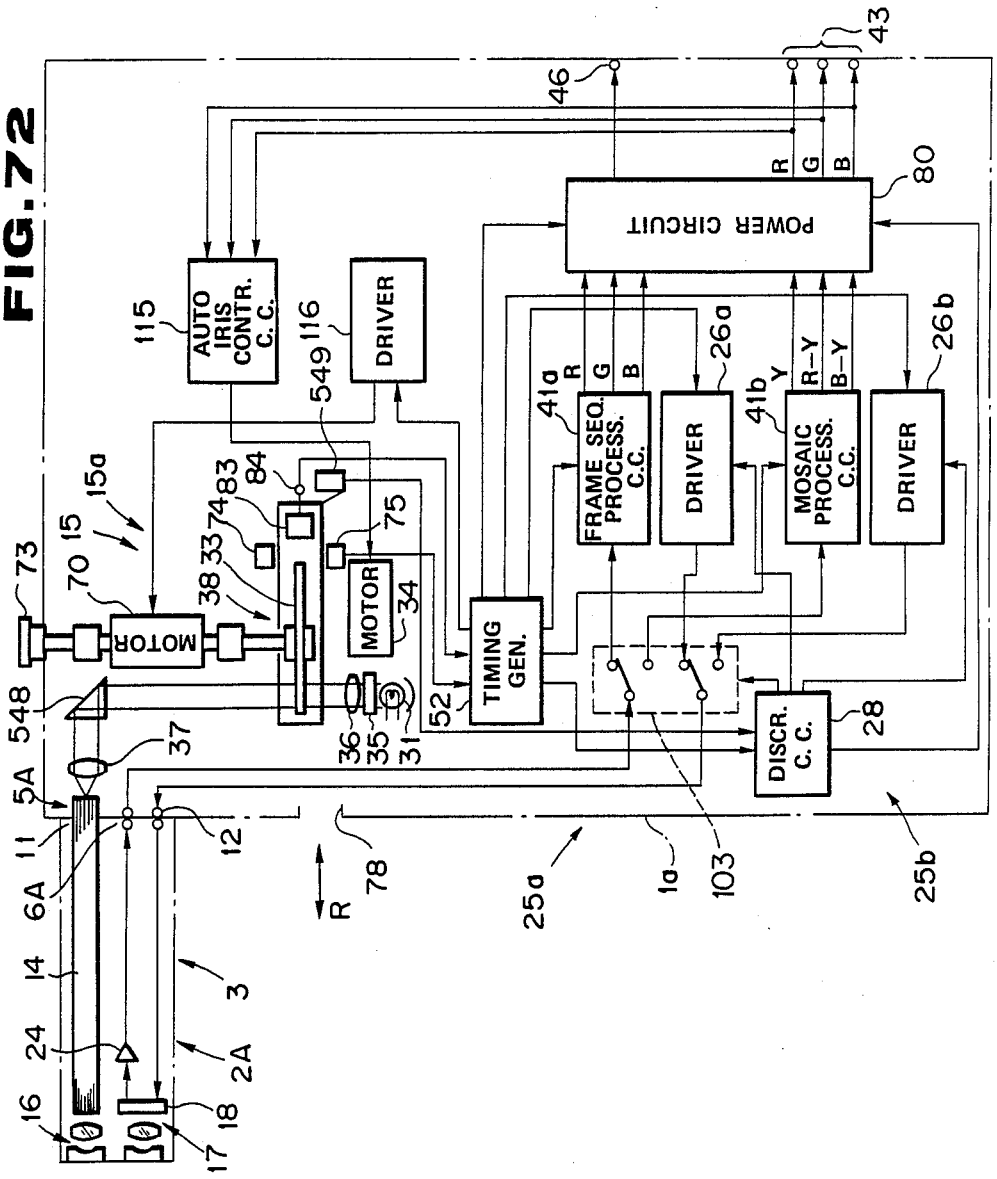

Further, as in FIG. 72, not only the switching switches 81 and 82 provided in the output circuit 80 may be switched but also an electric signal may be input into the discriminating circuit 28 from the switch 549 so that the switching switch 103 may be switched and the output of the output circuit 80 may be selected.

In FIG. 72, when the filter cassette 38 is inserted through the front surface plate 71 of the control apparatus 1a, the switch 549 will be on. This electric signal will be input into the discriminating circuit 28 which will switch a switching switch 103 and the switching switches 81 and 82 provided in the output circuit 80. By the switching switch 103, the driving pulse generated by the driver 26a may be applied to the CCD 18 and the video signal output from the CCD 18 may be input into the frame sequential type process circuit 41a.

By such formation as in FIGS. 71 and 72, no type signal generating circuit 27 is required for the scope 2 and externally fitted television camera and the electric circuit can be simplified.

As mentioned above, according to this embodiment, when the filter cassette 38 having color transmitting filters 32R, 32G and 32B which can transmit the illuminating light adaptable to the frame sequential type imaging system is made removably insertable, the illuminating light adapted to the electronic scopes 2 having the frame sequential type and color mosaic type imaging means, externally fitted television camera 8 and fiber scopes 2C, 2D and 2E will be able to be easily emitted.

Further, when the filter cassette 38 inserting position, removably fitting knob 73 operating position, light source connector receptacle 11 and signal connector receptacle 12 are concentrated in the control apparatus 1a, the operatability will be able to be improved.

FIGS. 73 to 76 show the 19th embodiment of the present invention.

In FIG. 73, in this embodiment, an aperture 78 through which the filter cassette 38 can be removably inserted from above is provided on the top plate 77 forming the upper part of the housing 29 of the control apparatus 1a.

Figure 75:
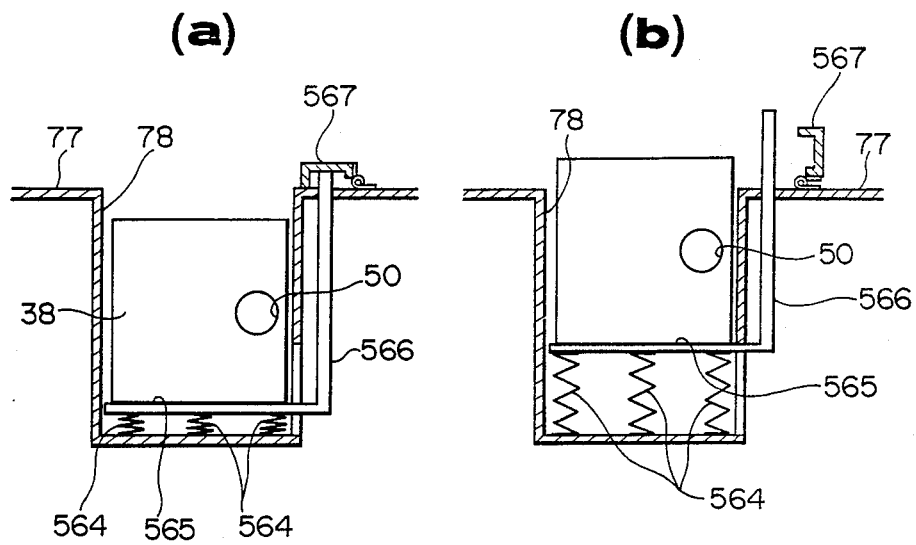
Figure 76:
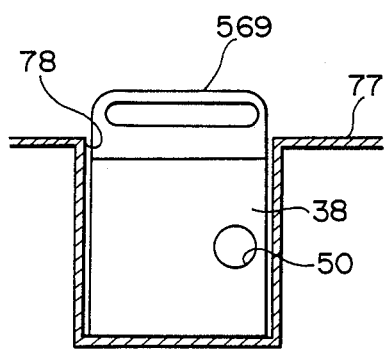

As in FIGS. 74 to 76, the operation of inserting and removing the filter cassette 38 is easy to make.

In FIGS. 74 (a) and 74 (b), the aperture 78 having a size through which the filter cassette 38 can be removably inserted is made through the top plate 77 forming the housing 29 of the control apparatus 1a and is provided with a lid 554 fitted with a handle 553 and provided to be free to open and close by hinges 556.

A plate-like elastic member 557 is pasted to the inside surface of the housing of this lid 554 and has a projection 558 formed on one end surface. An elastic member 561 having a groove-like recess 559 in which the projection 558 can be fitted is provided on the top plate 77 side corresponding to the end surface on which the projection 558 is provided. The top plate 562 of the filter cassette 38 is to contact the inside surface of the above mentioned elastic member 557. Further, the side plate 568 of the filter cassette 38 is to energize a plurality of such energizing members 564 as, for example, springs through a plate-like receptacle member 565.

The above mentioned lid 554 as closed energizes the energizing members 564 through the filter cassette 38 and is engaged by fitting the projection 558 with the recess 559. When this lid 554 is opened, the filter cassette 38 will project in the upper part out of the housing 29 and will be able to be easily pulled out by holding it in the upper part.

As in FIG. 75, the filter cassette 38 may be easily inserted and removed.

In FIG. 75, a plurality of energizing members 564 provided on the lower surface of the receptacle member 565 are energized by pressing a pressing bar 566 provided in the end part of the receptacle member 565 and projecting out of the top plate 77.

In FIG. 75 (A), the pressing bar 566 provided in the end part of the above mentioned receptacle member 565 is pressed in the upper part projecting out of the top plate 77 by a pressing member 567 to energize the energizing members 564 and the filter cassette 38 can be contained within the housing 29. By the way, the pressing member 567 can be engaged with the top plate 77 by an engaging means not illustrated so as to be able to remain pressing the pressing bar 566. In case the filter cassette 38 is to be pulled out, when the pressing member 567 is removed from the pressing bar 566 as in FIG. 75 (b), the filter cassette 38 will be projected in the upper part out of the housing 29 by the energizing members 564 and will be able to be easily pulled out.

Also, in case the filter cassette 38 is contained within the housing 29 as in FIG. 76, a handle 569 provided on the top of the filter cassette 38 may project out of the top plate 77.

By such formation as in this embodiment, the prism 548 used in the first embodiment can be omitted and the formation of the optical system of the light source apparatus 15 can be simplified.

The other formations, operations and effects are the same as in the first embodiment.

Figure 77:
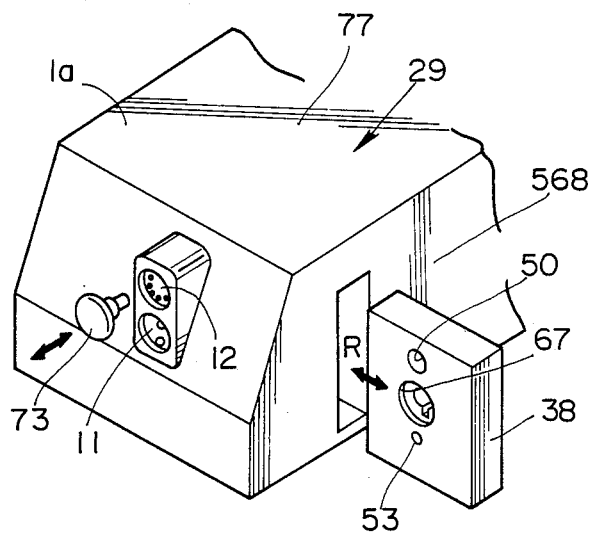
FIG. 77 is a perspective view of an endoscope controlling apparatus relating to the 20th embodiment of the present invention.

FIG. 77 shows the 20th embodiment of the present invention.

In this embodiment, the side plate 568 forming the side of the housing 29 of the control apparatus 1a is provided with an aperture 78 through which the filter cassette 38 can be inserted and removed.

The other formations, operations and effects are the same as in the first and second embodiments.

In the above mentioned respective embodiments, the color transmitting filters 32 are filters transmitting the respective colors of red (R), green (G) and blue (B) but are not limited to these and may be filters for such special observation as, for example, an infrared observation.

Figure 80:
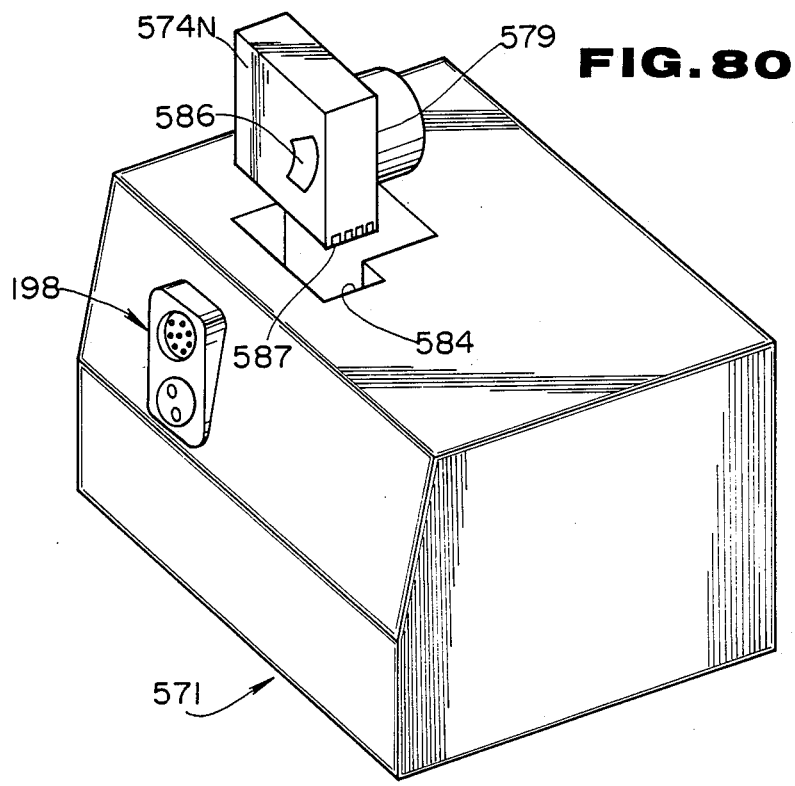

FIGS. 781 to 80 show the 21st embodiment of the present invention.

Figure 78:
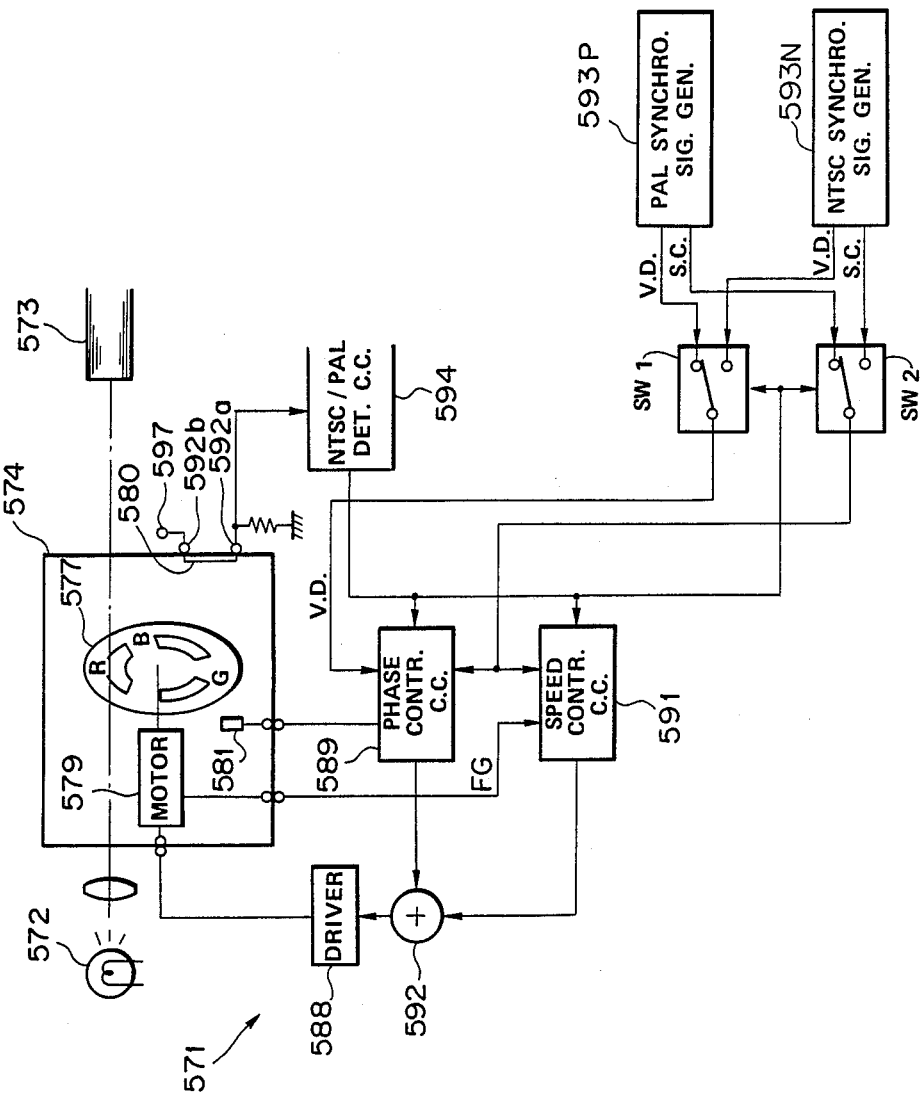
FIGS. 78 to 80 relate to the 21st embodiment of the present invention.
Figure 79:
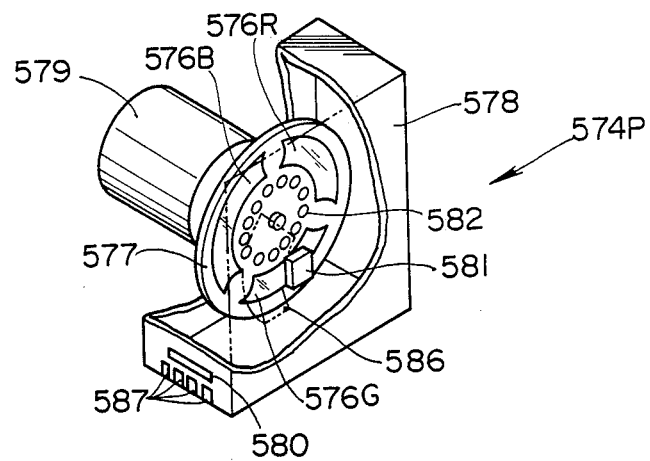

A light source apparatus 571 in this embodiment is formed as shown in FIG. 78. This light source apparatus 571 is provided with a lamp 572 emitting a white color light. A cassette fitting part is provided in the illuminating light path between this lamp 572 and the entrance end of a light guide 573 connected with this lamp so that the filter cassette 574 may be removably fitted. As shown in FIG. 79, this filter cassette 574 is internally provided within a housing 578 with a rotary filter on which filters 576R, 576G and 576B transmitting lights of respective wavelength regions, for example, of red (R), green (G) and blue (B) are arranged in the peripheral direction and has a motor 579 rotating and driving this rotary filter fitted to a housing 578. This filter cassette 574 has a plurality of kinds, for example, a PAL filter cassette 574P and NTSC filter cassette 574N prepared. One, for example, the PAL filter cassette 574P is provided with a kind detecting contact piece (point) 580 on one side surface of the housing 578. The other NTSC filter cassette 574N is not provided with this kind detecting contact piece 580. In the cassette fitting part of the above mentioned light source apparatus 571, a rotating position detecting photosensor 5811 is arranged as opposed to the rotary filter 577 of the fitted filter cassette 574. On the other hand, on the rotary filter 577 side, as shown in FIG. 79, rotating position detecting marks 582 are formed. Further, as shown in FIG. 80, for example, on the upper surface of the housing of the light source apparatus 571, a cassette removably inserting part 584 communicating with the above mentioned cassette fitting part is formed so that the filter cassette 574 may be inserted and removed through this removably inserting part 584. The above mentioned filter cassette 574 is provided with windows 586 on the front and back surfaces facing the illuminating light path. Also, on one side surface of the housing 578 of this filter cassette 574, there are provided electric contacts 587 connecting the motor 579 and photosensor 581 with a circuit within the light source apparatus 571.

As shown in FIG. 78, a driver 588 driving and controlling the above mentioned motor 579 is provided within the above mentioned light source apparatus 571. The output of a phase controlling circuit 589 and the output of a speed controlling circuit 591 are added together by an adder 592 and are input into this driver 588. A phase signal from the photosensor 581 and vertical synchronous signal VD and subcarrier SC from a synchronous signal generating circuit 593 as reference signals are input into the above mentioned phase controlling circuit 589. By this phase controlling circuit 589, the phase signal from the photosensor 581 is compared in the phase with the reference signals and a signal corresponding to the phase difference is output. A speed signal FG from a speed sensor not illustrated provided in the above mentioned motor 579 and the subcarrier SC from the synchronous signal generating circuit 593 as a reference signal are input into the above mentioned speed controlling circuit 591. This speed controlling circuit 591 outputs a signal corresponding to the speed difference from the reference speed. Thus, the rotary filter 577 internally provided in the filter cassette 574 is controlled and rotated by the phase synchronizing control using also the speed control.

Now, in this embodiment, the synchronous signal generating circuit 593 outputting the vertical synchronous signal VD and subcarrier SC as the above mentioned reference signals is provided with a PAL synchronous signal generating circuit 593P and NTSC synchronous signal generating circuit 593N so that, depending on whether the selected and fitted filter cassette 574 is 574P for PAL or 574N for NTSC, a switching switch SW1 or SW2 may be switched and, in response to the system (kind) of the fitted filter cassette 574, a PAL synchronous signal generating circuit 593P or NTSC synchronous signal generating circuit 593N may be switched. That is to say, the light source apparatus 571 has an NTSC/PAL detecting circuit 594 connected to a contact 592a provided in the cassette fitting part and is further provided in the above mentioned cassette fitting part with a contact 592b connected to a current source (for example, of 5V) so that, when the PAL filter cassette 574P is fitted, as the above mentioned PAL filter cassette 574P has a detecting contact piece 580, the above mentioned contacts 592a and 592b will conduct between them, a voltage, for example, of 5V will be applied to the NTSC/PAL detecting circuit 594 from the current source 597 and the fitted filter cassette 574 will be detected to be PAL 574P. On the other hand, when the NTSC filter cassette 574N is fitted to the fitting part, as this cassette 574N has no detecting contact piece 580, the contacts 592a and 592b will not conduct between them, therefore the voltage applied to the NTSC/PAL detecting circuit 594 will be 0 and the fitted filter cassette 574 will be detected to be an NTSC 574N. The detected output of the above mentioned detecting circuit 31 is fed to the switches SW1 and SW2. These switches SW1 and SW2 are switched in response to the kind detection and the above mentioned be on in case the cassette filter 38 is inserted and to be off in case the cassette filter 38 is pulled out. As described also in the 15th embodiment, the on-off signal of this switch 492 is input into an automatic light adjusting circuit 115 and also into an indicating circuit not illustrated connected to an indicating lamp 598a provided on the front surface plate 71 forming the housing 29 and showing that the filter cassette 38 is pulled out and to an indicating lamp 598b showing that the filter cassette 38 is inserted so as to light the indicating lamp 598b in case the signal from the switch 492 is on and to light the indicating lamp 598a in case the signal from the switch 492 is off.

By such formation as in this embodiment, a scope 2 of a different imaging system will not be connected to the light source apparatus 15 by mistake and the handlability will be able to be improved.

By the way, in this embodiment, only the insertion and removal of the filter cassette 38 are indicated but the indication is not limited to this and the intensity and blanking period of the illuminating light may be indicated. detected output is fed to the phase controlling circuit 589 and speed controlling circuit 591.

Thus, the kind of the filter cassette 574 fitted to the filter fitting part of the light source apparatus 571 is detected by the NTSC/PAL detecting circuit 594, the synchronous signal generating circuit 593 is selected and the number of revolutions of the rotary filter 577 is controlled and set in response to the kind (whether for PAL or NTSC) of the filter cassette 574.

By the way, in this embodiment, the kind of a filter cassette (rotary filter) for SECAM may be added to those mentioned above. Further, the kind of the filter cassette is not limited to the video system kind but the video processor may be controlled, for example, in response to the number of pixels of the solid state imaging device and various applications may be made.

In the above described embodiment, the rotary filter driving motor is incorporated in the filter cassette but may be provided on the light source apparatus side and only the rotary filter may be contained within the filter cassette.

Figure 81:
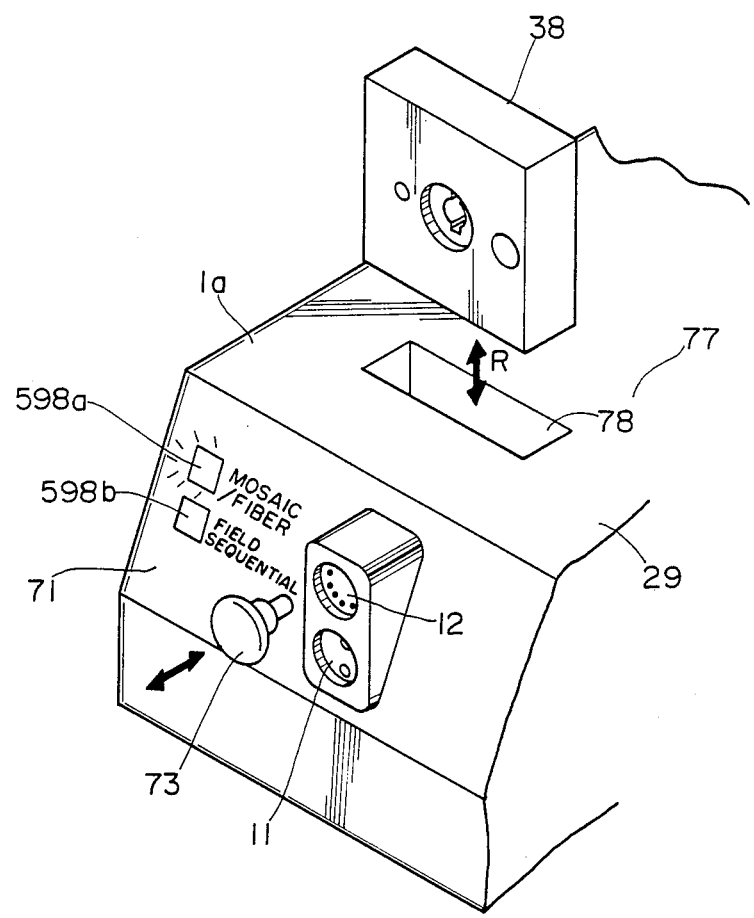
FIG. 81 relates to the 22nd embodiment of the present invention and is a perspective view explaining a panel of a light source apparatus.

FIG. 81 shows the 22nd embodiment of the present invention.

In this embodiment, an indicating lamp 598 indicating that the filter cassette 38 is inserted is provided on the light source apparatus 15 described in the 15th embodiment.

An inserting part 78 through which the filter cassette 38 can be inserted is provided on the top plate 77 forming the housing 29 containing the light source apparatus 15. A switch 492 is provided within this inserting part 78 so as to

What is claimed is:

1. An endoscope light source apparatus for transmitting an illuminating light to an endoscope comprising:
    a light source emitting the illuminating light;
    an output surface for transmitting said illuminating light to the endoscope;
    a housing for enclosing said light source and for supporting said output surface, wherein said housing includes an inserting aperture disposed in a light path between said light source and said output surface for receiving an object therein;
    a cassette having a structure cooperative with said inserting aperture such that said cassette is removably insertable in said inserting aperture and in the light path between said light source and said output surface;
    a light transmitting means, disposed within said cassette and thus in the light path between the light source and the output surface, for sequentially transforming the illuminating light in the light path into a light beam having one of a plurality of different wavelengths, said light transmitting means comprising a rotatable rotary filter having a connecting part thereon, wherein said connecting part connects with a driving means located externally of said cassette for rotating said rotary filter.

2. An endoscope light source apparatus for feeding an illuminating light to an endoscope along a light path, comprising:
    a light source filter containing container provided with the light source apparatus feeding an illuminating light to the endoscope;
    light transmitting means removably insertable in said light path for limiting the transmitted light amount at least in one specific wavelength, said light transmitting means comprising a rotatable rotary filter having a connecting part thereon;
    a cassette containing said light transmitting means;
    wherein said connecting part connects with a driving means located externally of said cassette for rotating said rotary filter.

3. An endoscope light source apparatus according to claim 1 or 2 wherein said rotary filter comprises a plurality of color separating filters for separating said illuminating light into three wavelength regions for forming color-picture images.

4. An endoscope light source apparatus according to claim 3 wherein said driving means cooperates with said cassette for rotating said rotary filter to sequentially alternate said color separating filters in time series within said light path.

5. An endoscope light source apparatus according to claim 4 further comprising transmitting means for transmitting rotational motion from said driving means to said rotary filter.

6. An endoscope light source apparatus according to claim 1 or 2 wherein said light transmitting means has at least two of a light reducing filter reducing the light amount over the entire wavelength region of said illuminating light, a transmitting part not limiting the wavelength region of the illuminating light and a wavelength limiting filter limiting the wavelength region of the illuminating light and is rotatable and said light reducing filter, transmitting part and wavelength limiting filter can stop in the light path.

7. An endoscope light source apparatus according to claim 6 wherein said light reducing filter, transmitting part and wavelength limiting filter are removably provided on a turret disc.

8. An endoscope light source apparatus according to claim 1 or 2 wherein said light transmitting means has at least two light reducing filters of different reduced light amounts.

9. An endoscope light source apparatus according to claim 1 or 2 wherein said light transmitting means has at least two wavelength limiting filters limiting the wavelength region of the illuminating light.

10. An endoscope light source apparatus according to claim 1 or 2 wherein said light transmitting means has at least two transmitting parts not limiting the wavelength region of the illuminating light.

11. An endoscope light source apparatus according to claim 1 or 2 wherein said light transmitting means is provided with a first rotary filter having color separating filters separating in time series said illuminating light into three wavelength regions capable of forming color picture images and a second rotary filter having a wavelength limiting filter limiting the transmitted wavelength region of the illuminating light passing through the color separating filters of said first rotary filter and a transmitting part not limiting the transmitted wavelength regions of the color separating filters of said first rotary filter at least at the time of stopping and rotating as synchronized with the first rotary filter at the time of rotating.

12. An endoscope light source apparatus according to claim 6 wherein said light transmitting means is further provided with a rotary filter having color separating filters separating in time series said illuminating light into three wavelength regions capable of forming color picture images.

13. An endoscope light source apparatus according to claim 1 or 2 wherein said light transmitting means comprises a plurality of rotary filters, wherein at least one of said rotary filters has a plurality of color separating filters for separating said illuminating light into three wavelength regions for forming color picture images.

14. An endoscope light source apparatus according to claim 13 wherein said light transmitting means comprises filter switching means for selectively inserting one of said plurality of rotary filters into the light path of said light source.

15. An endoscope light source apparatus according to claim 1 or 2 wherein said cassette has a plurality of windows which can transmit the transmitted light of said light transmitting means and one window selected from the plurality of windows can be interposed in the light path.

16. An endoscope light source apparatus according to claim 15 wherein said plurality of windows have at least two of a light reducing filter reducing the light amount of the entire wavelength region of the illuminating light, a transmitting part not limiting the wavelength region of the illuminating light and a wavelength limiting filter limiting the wavelength region of the illuminating light and said light reducing filter, transmitting part and wave length limiting filter can be selectively interposed in the light path.

17. An endoscope light source apparatus according to claim 1 or 2 wherein said light transmitting means has at least two light reducing filters of different reduced light amounts.

18. An endoscope light source apparatus according to claim 1 or 2 wherein said light transmitting means has at least two wavelength limiting filters limiting the wavelength region of the illuminating light.

19. An endoscope light source apparatus according to claim 1 or 2 wherein said light transmitting means has at least two transmitting parts not limiting the wavelength region of the illuminating light.

20. An endoscope light source apparatus according to claim 1 wherein said light source is provided with a light amount adjusting means whereby the light amount of the illuminating light emitted from said light source can be adjusted by sensing whether said cassette is inserted in the light path or not.

21. An endoscope light source apparatus according to claim 1 wherein said driving means has a resolution number controlling means whereby the number of revolutions driving the rotary filter is read out of a memory means provided in said cassette and said rotary filter is driven on the basis of the read out data.

22. An endoscope light source apparatus according to claim 1 wherein said light source apparatus has further an indicating means of sensing the kind of the rotary filter inserted in the light path and indicating said kind.

23. An endoscope light source apparatus according to claim 1 wherein said light source apparatus has further an indicating means which can sense and indicate the insertion and pulling of said rotary filter in and out of the light path.

24. An endoscope light source apparatus according to claim 13 wherein said rotary filters are rotatably provided within said cassette and further comprising driving means cooperating with said cassette for rotating said rotary filters to sequentially alternate said color separating filters in time series within said light path.

* * * * *

UNITED STATES PATENT AND TRADEMARK OFFICE
CERTIFICATE OF CORRECTION

PATENT NO. : 4,983,019

DATED : January 8, 1991

INVENTOR(S) : Yuji IKUNO et al

It is certified that error appears in the above-identified patent and that said Letters Patent is hereby corrected as shown below:

On the cover page, Item [75], "Yuji Ikuni" should read -- Yuji Ikuno --.

Signed and Sealed this

Fifteenth Day of September, 1992

Attest:

DOUGLAS B. COMER

*Attesting Officer*  *Acting Commissioner of Patents and Trademarks*